(12) United States Patent
Oikawa et al.

(10) Patent No.: US 11,334,998 B2
(45) Date of Patent: May 17, 2022

(54) MEDICAL IMAGE PROCESSING APPARATUS, X-RAY DIAGNOSTIC APPARATUS, AND COMPUTER-IMPLEMENTED METHOD

(71) Applicant: CANON MEDICAL SYSTEMS CORPORATION, Otawara (JP)

(72) Inventors: Hirona Oikawa, Nasushiobara (JP); Shingo Abe, Nasushiobara (JP); Kunio Shiraishi, Otawara (JP); Toshiya Waku, Yaita (JP); Shumpei Ohashi, Otawara (JP); Akihito Takahashi, Nasushiobara (JP); Saki Hashimoto, Nasushiobara (JP); Jumpei Ogasawara, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 87 days.

(21) Appl. No.: 16/853,855

(22) Filed: Apr. 21, 2020

(65) Prior Publication Data

US 2020/0334815 A1 Oct. 22, 2020

(30) Foreign Application Priority Data

Apr. 22, 2019 (JP) .............................. JP2019-080863
Apr. 20, 2020 (JP) .............................. JP2020-074676

(51) Int. Cl.
*G06K 9/00* (2022.01)
*G06T 7/00* (2017.01)
(Continued)

(52) U.S. Cl.
CPC ............ *G06T 7/0014* (2013.01); *G06T 7/215* (2017.01); *G06T 7/74* (2017.01); *G16H 30/20* (2018.01);
(Continued)

(58) Field of Classification Search
CPC ......... G06T 7/0014; G06T 7/215; G06T 7/74; G06T 2207/10116; G06T 2207/20081;
(Continued)

(56) References Cited

U.S. PATENT DOCUMENTS

2008/0205591 A1 8/2008 Ozawa
2011/0069063 A1 3/2011 Liao et al.
(Continued)

FOREIGN PATENT DOCUMENTS

| EP | 2 088 556 A1 | 8/2009 |
|---|---|---|
| JP | 2008-212241 A | 9/2008 |
| JP | 5537262 B2 | 7/2014 |

OTHER PUBLICATIONS

Extended European Search Report dated Aug. 3, 2020 in European Patent Application No. 20170648.8, 8 pages.
(Continued)

*Primary Examiner* — Atiba O Fitzpatrick
(74) *Attorney, Agent, or Firm* — Oblon, McClelland, Maier & Neustadt, L.L.P.

(57) ABSTRACT

According to one embodiment, a medical image processing apparatus includes processing circuitry. The processing circuitry specifies, before position alignment between a first X-ray image and a second X-ray image which is acquired with a device inserted, a device area candidate in the second X-ray image as a candidate of an area where the device appears. The processing circuitry performs the position alignment using first processing of removing the specified device area candidate or second processing of reducing a contribution of the specified device area candidate.

18 Claims, 44 Drawing Sheets

(51) Int. Cl.
  *G06T 7/215* (2017.01)
  *G06T 7/73* (2017.01)
  *G16H 30/20* (2018.01)
(52) U.S. Cl.
  CPC .............. *G06T 2207/10116* (2013.01); *G06T 2207/20081* (2013.01); *G06T 2207/30101* (2013.01)
(58) Field of Classification Search
  CPC ........... G06T 2207/30101; G06T 5/005; G06T 5/006; G16H 30/20
  See application file for complete search history.

(56) References Cited

U.S. PATENT DOCUMENTS

| 2011/0293164 | A1  | 12/2011 | Sato et al. |           |
|---|---|---|---|---|
| 2014/0270436 | A1* | 9/2014  | Dascal  | A61B 6/463 382/130 |
| 2016/0171716 | A1* | 6/2016  | Schafer | G06T 7/0012 382/107 |
| 2017/0148158 | A1* | 5/2017  | Najarian | A61B 5/7203 |
| 2020/0242767 | A1* | 7/2020  | Zhao    | A61B 6/50 |
| 2021/0142504 | A1* | 5/2021  | Dascal  | G06T 7/70 |

OTHER PUBLICATIONS

Vincent Bismuth, "Image processing algorithms for the visualization of interventional devices in X-ray fluoroscopy," Doctoral Thesis, Retrieved from the Internet [URL: https://tel.archives-ouvertes.fr/tel-00747682/], XP055302247, Jan. 9, 2012, 250 pages.

Maximilian Baust, et al., "Stent graft removal for improving 2D-3D registration," IEEE International Symposium on Biomedical Imaging: From Nano to Macro, ISBI 2009, XP031502269, 2009, pp. 1203-1206.

* cited by examiner

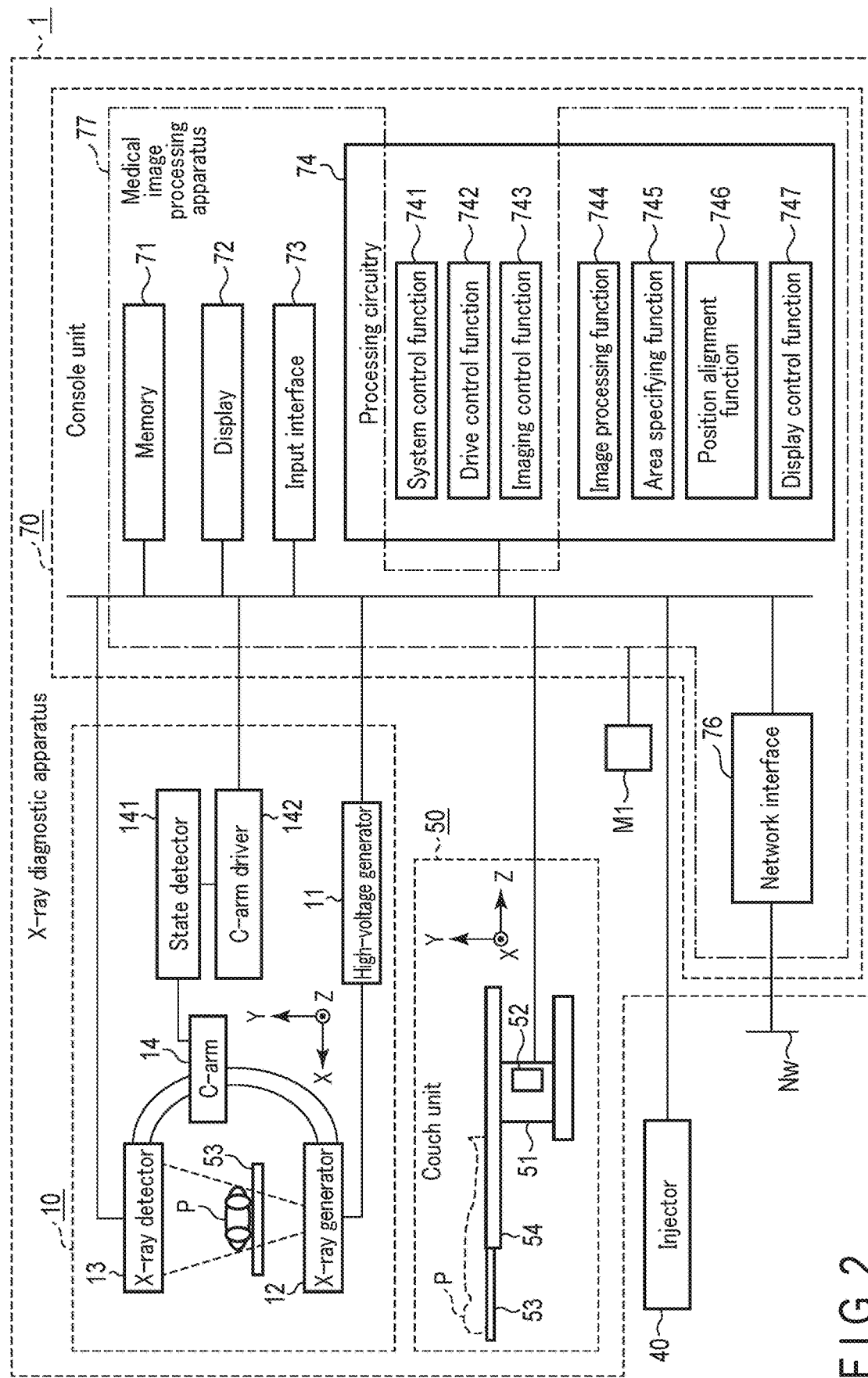
F I G. 2

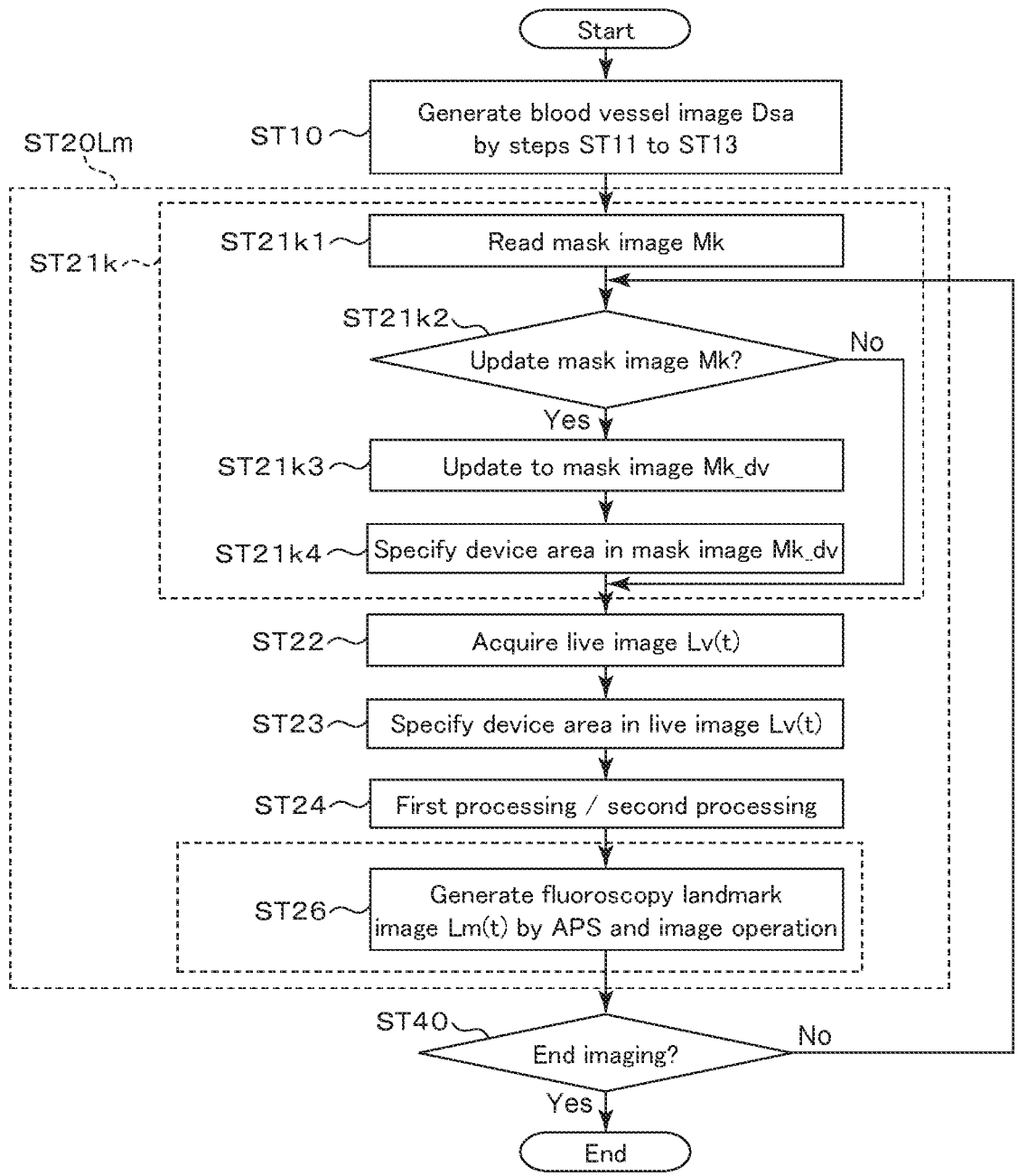
F I G. 14

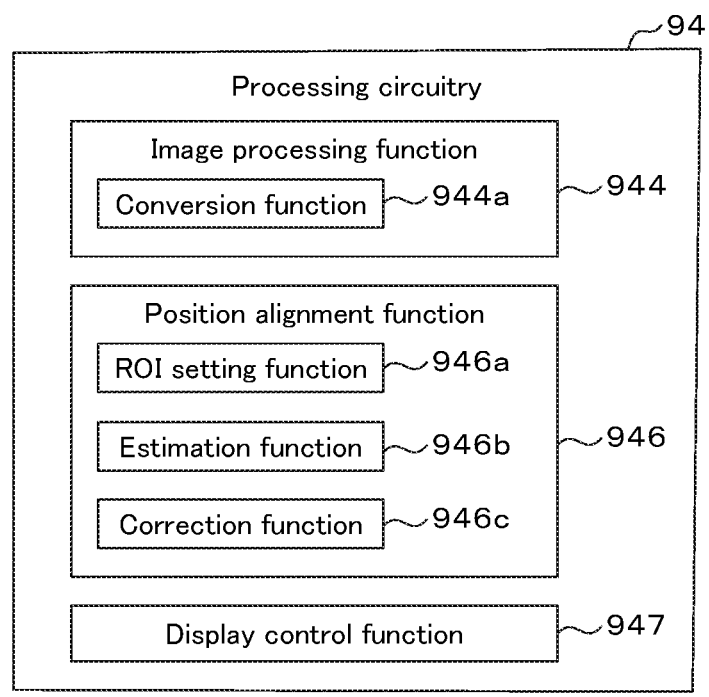
F I G. 24

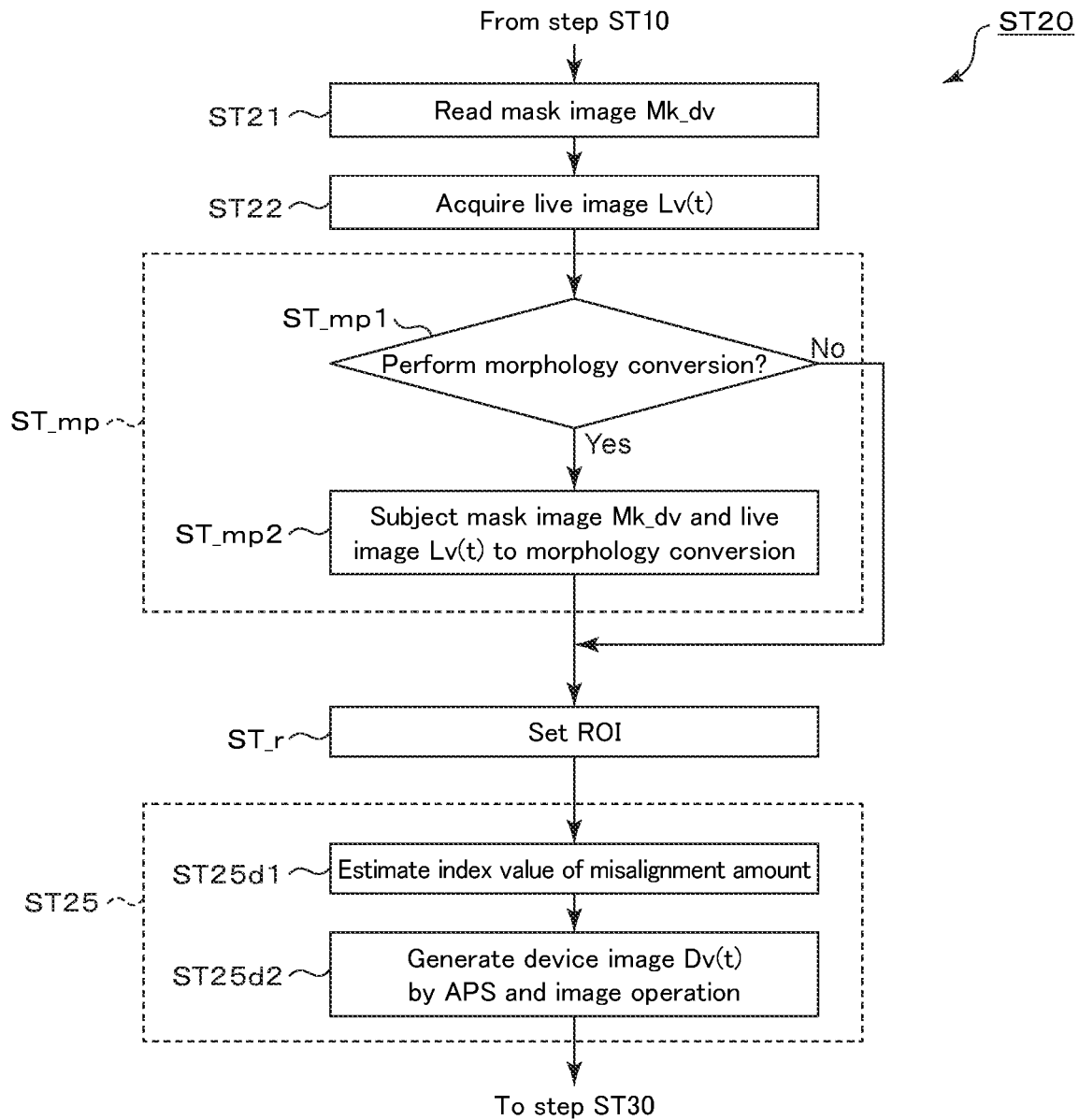
F I G. 26

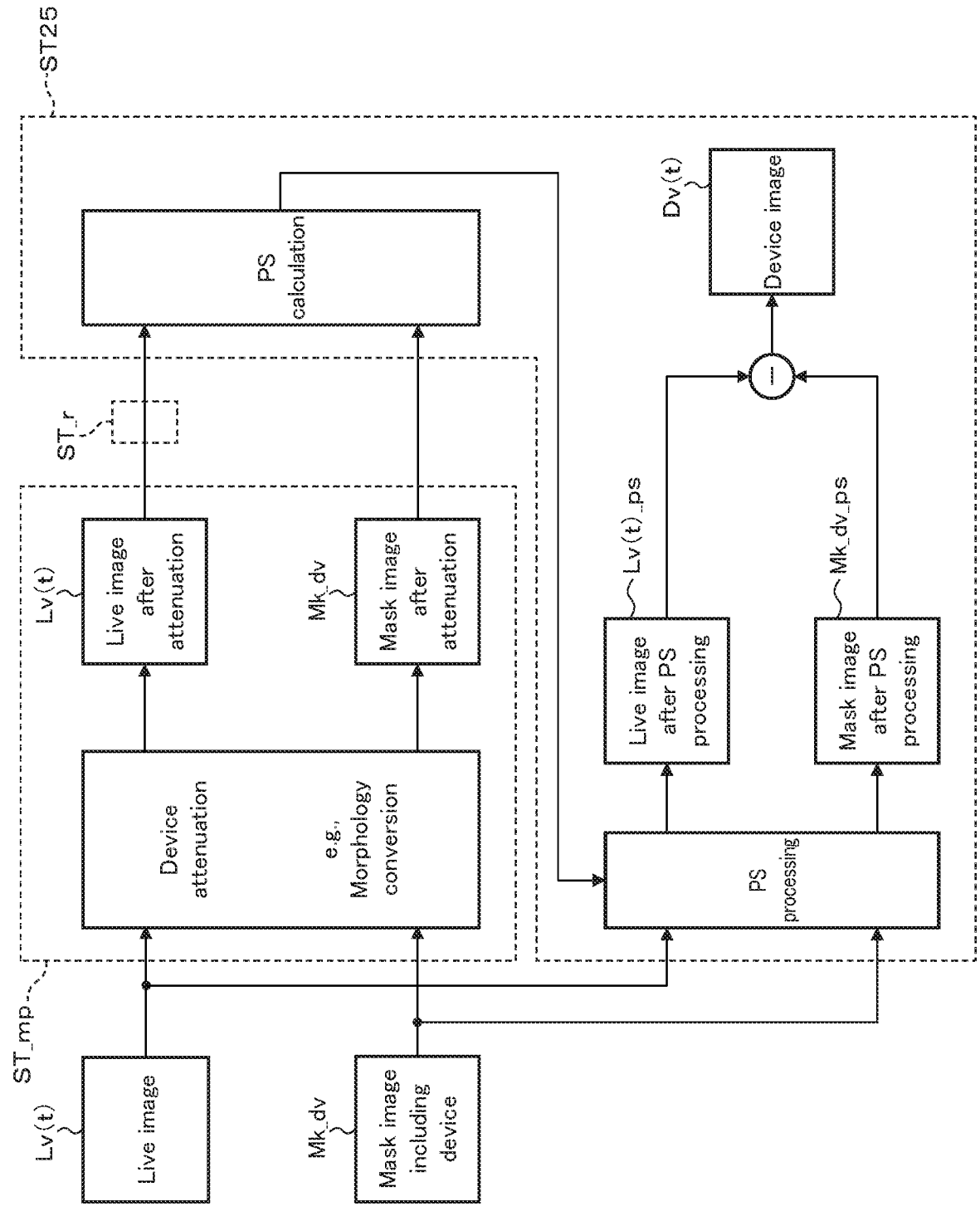
F I G. 27

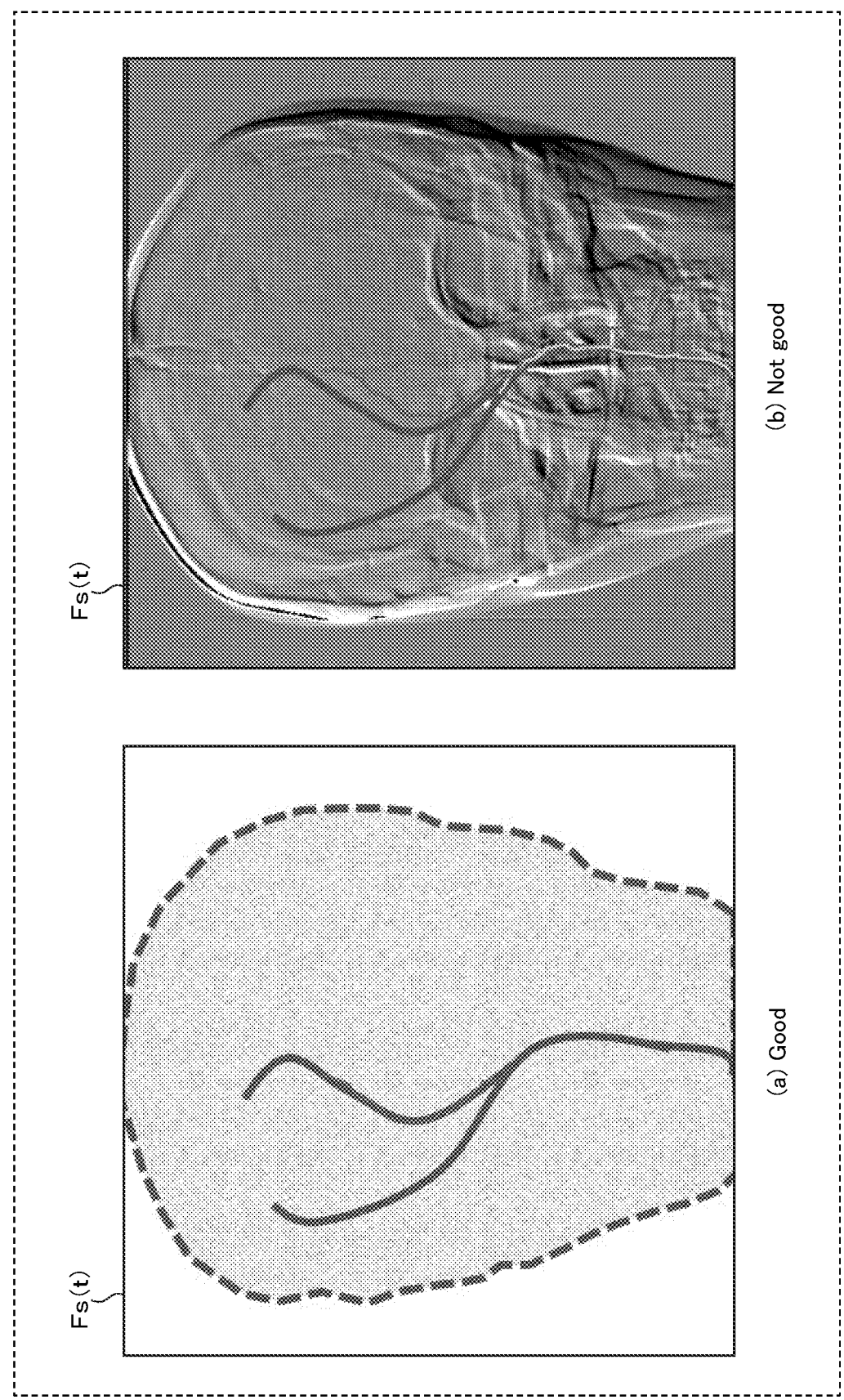
F I G. 32

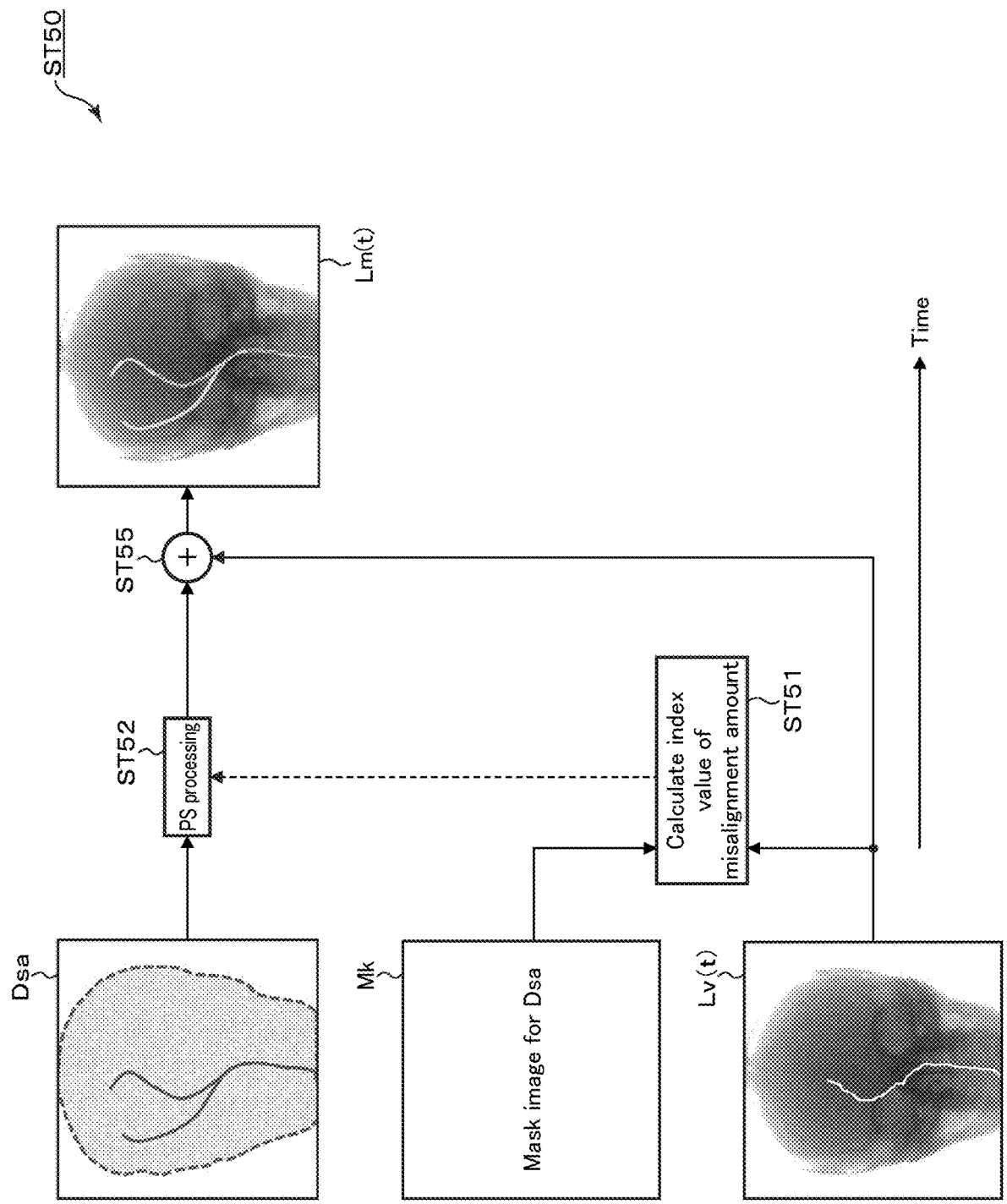
F I G. 37

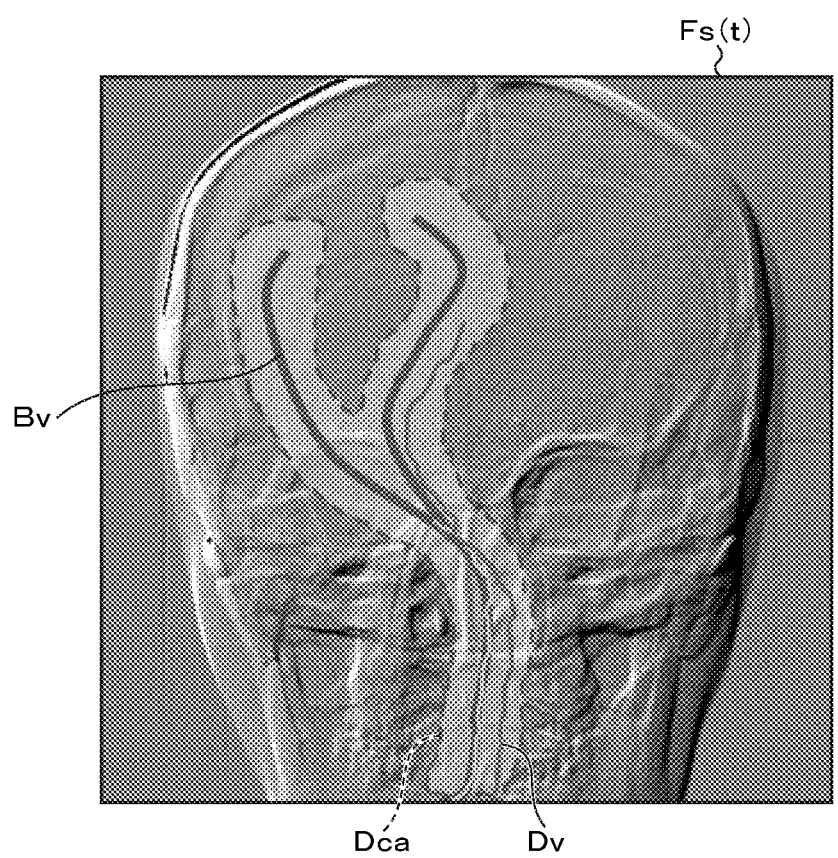
F I G. 39

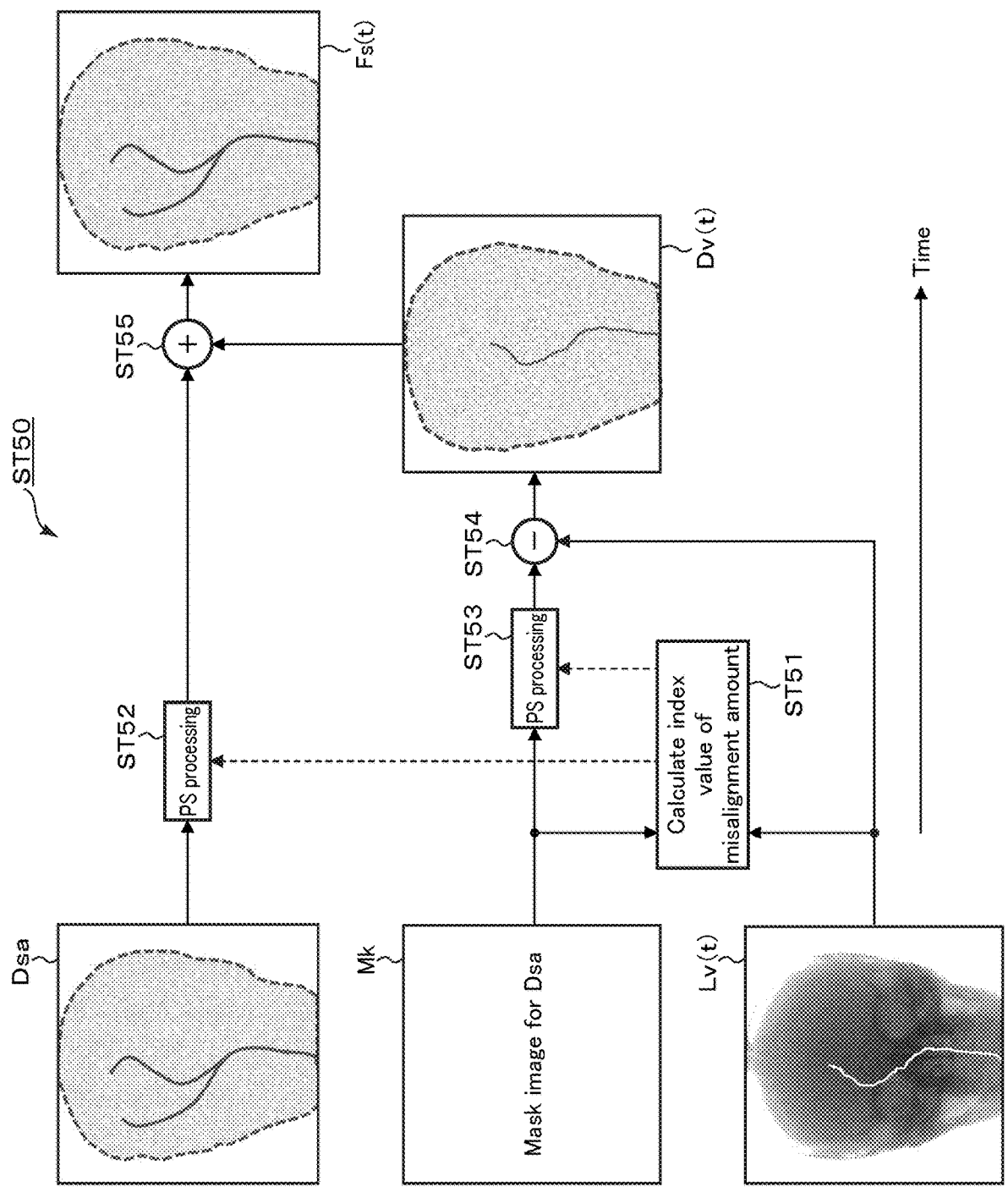
F I G. 44

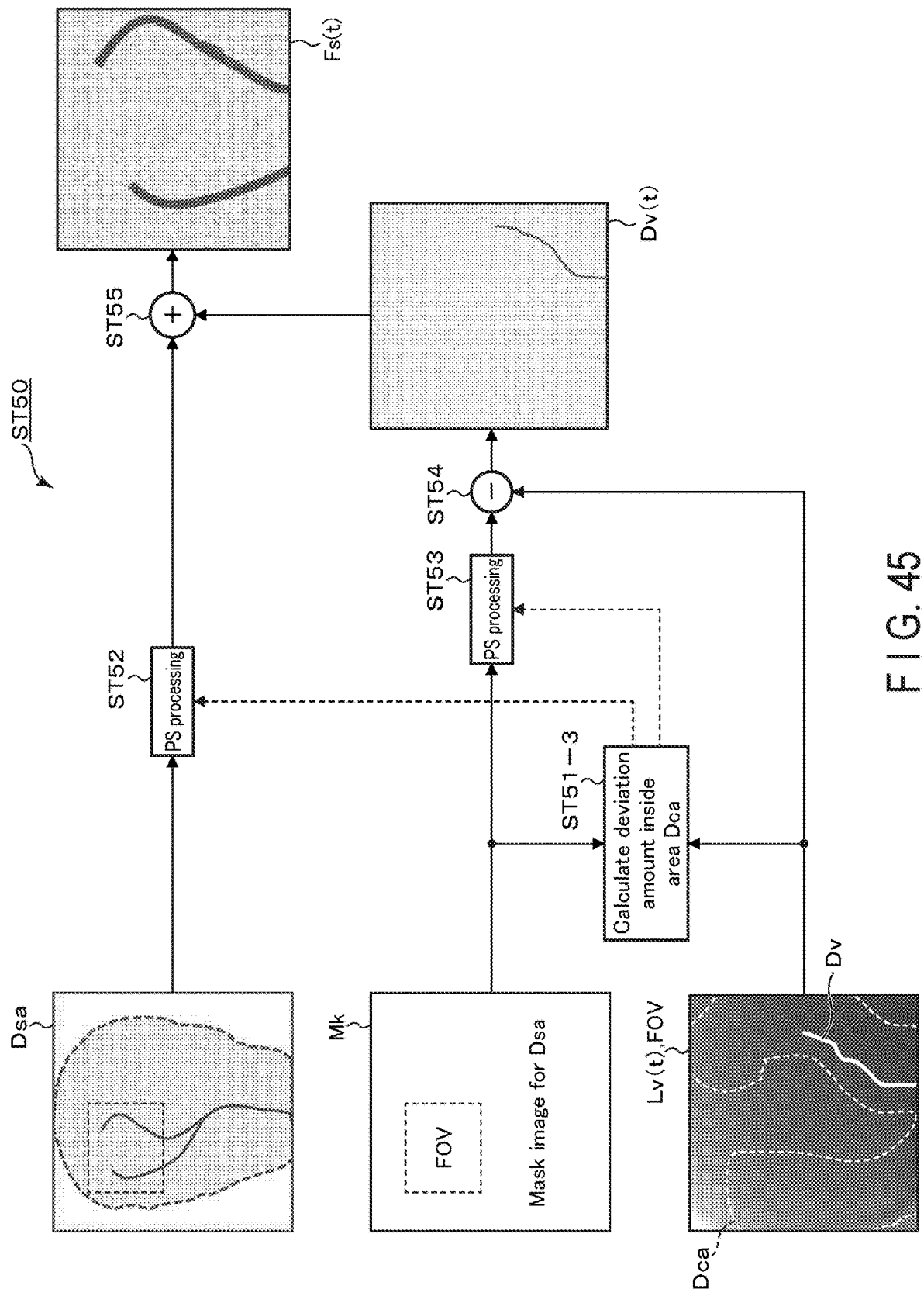
F I G. 45

MEDICAL IMAGE PROCESSING APPARATUS, X-RAY DIAGNOSTIC APPARATUS, AND COMPUTER-IMPLEMENTED METHOD

CROSS-REFERENCE TO RELATED APPLICATIONS

This application is based upon and claims the benefit of priority from prior Japanese Patent Application No. 2019-80863 filed Apr. 22, 2019, and Japanese Patent Application No. 2020-74676 filed Apr. 20, 2020, the entire contents of which are incorporated herein by reference.

FIELD

Embodiments described herein relate generally to a medical image processing apparatus, an X-ray diagnosis apparatus, and a computer-implemented method.

BACKGROUND

An X-ray diagnostic apparatus is known, which is adapted to perform processing for position alignment (registration) and subtraction between a mask image acquired before injection of a contrast medium and a contrast image acquired after injection of the contrast medium, whereby displaying a blood vessel image that corresponds to the contrast image having its background taken away and showing thus extracted blood vessels. Such blood vessel images are called DSA images and used for observing a stenosis position in blood vessels, conditions of blood vessels, and so on. Here, "DSA" stands for digital subtraction angiography. The contrast image may also be called a contrast-enhanced image.

In the course of intravascular treatment subsequent to the observation, a subject undergoes fluoroscopic imaging by the X-ray diagnostic apparatus. A doctor inserts a device such as a catheter or a guide wire into the blood vessel of the subject, and advances the device to the treatment site (e.g., aneurysm) while seeing a fluoroscopic image (live image) obtained by the fluoroscopic imaging. This work generally adopts a technique called fluoroscopy roadmap, where the X-ray diagnostic apparatus performs position alignment between the most recently-generated blood vessel image and the live image and displays these images in a superimposed manner. According to the fluoroscopy roadmap of such processing, a background in the live image, such as bone, etc., may be erased or left unerased. The fluoroscopy roadmap embraces a technique of displaying the blood vessel image, the device, etc. by erasing the background from the live image, which is called fluoroscopy subtraction, and a technique of displaying the background in addition to the blood vessel image, the device, etc., which is called fluoroscopy landmark. Also, for generating such blood vessel images and fluoroscopy roadmap images, auto pixel shift (APS) is adopted as a technique of automatically aligning the positions of two images.

This auto pixel shift technique normally serves well, but the study of the present inventor has revealed that it occasionally incurs errors in the position alignment due to the device moving during the fluoroscopic imaging, so it leaves room for improvement. For example, when the device has advanced to overlap the edge of bone or the like during the fluoroscopic imaging, the device appearing within the live image can interfere with this bone edge, etc., causing an error in the inter-image position alignment. In another occasion, when the mask image for erasing the live image's background shows a device, the device appearing in the mask image and the device appearing in the live image, which are not at corresponding positions, can interfere with each other, causing an error in the inter-image position alignment. With the error occurrence in the position alignment, backgrounds in two images cannot cancel each other out, and the blood vessel image or the fluoroscopy roadmap image generated by an image operation after such position alignment will involve an artifact.

BRIEF DESCRIPTION OF THE DRAWINGS

FIG. 2 is a block diagram showing a configuration of the X-ray diagnostic apparatus according to the first embodiment.

FIG. 14 is a flowchart for explaining operations in a modification of the second embodiment.

FIG. 24 is a block diagram showing a configuration of processing circuitry of a medical image processing apparatus according to a fourth embodiment.

FIG. 26 is a flowchart for explaining operations in the fourth embodiment.

FIG. 27 is a schematic diagram for explaining the operations in the fourth embodiment.

FIG. 32 is a schematic diagram for explaining, for the fifth embodiment, a case of good position alignment and a case of bad position alignment.

FIG. 37 is a schematic diagram for explaining a first modification of the operations in the fifth embodiment.

FIG. 39 is a schematic diagram for explaining an amount of deviation outside a device area candidate, according to a sixth embodiment.

FIG. 44 is a schematic diagram for explaining operations in the seventh embodiment.

FIG. 45 is a schematic diagram for explaining operations in the seventh embodiment.

DETAILED DESCRIPTION

According to one embodiment, a medical image processing apparatus includes processing circuitry. The processing circuitry specifies, before position alignment between a first X-ray image and a second X-ray image, a device area candidate in the second X-ray image as a candidate of an area where the device appears. The second X-ray image is acquired with a device inserted. The processing circuitry performs the position alignment using first processing of removing the specified device area candidate or second processing of reducing a contribution of the device area candidate. This can reduce errors in the position alignment (registration) between the images, which can occur due to the movement of the device during fluoroscopic imaging.

Now, the embodiments will be described with reference to the drawings.

First Embodiment

Figure 1:
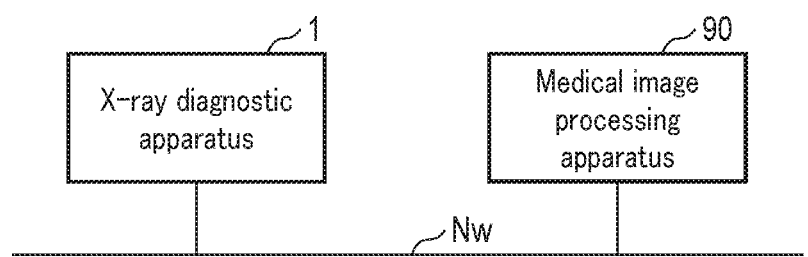
FIG. 1 is a block diagram showing a configuration of a medical image processing system according to a first embodiment, which includes an X-ray diagnostic apparatus and a medical image processing apparatus.
Figure 3:
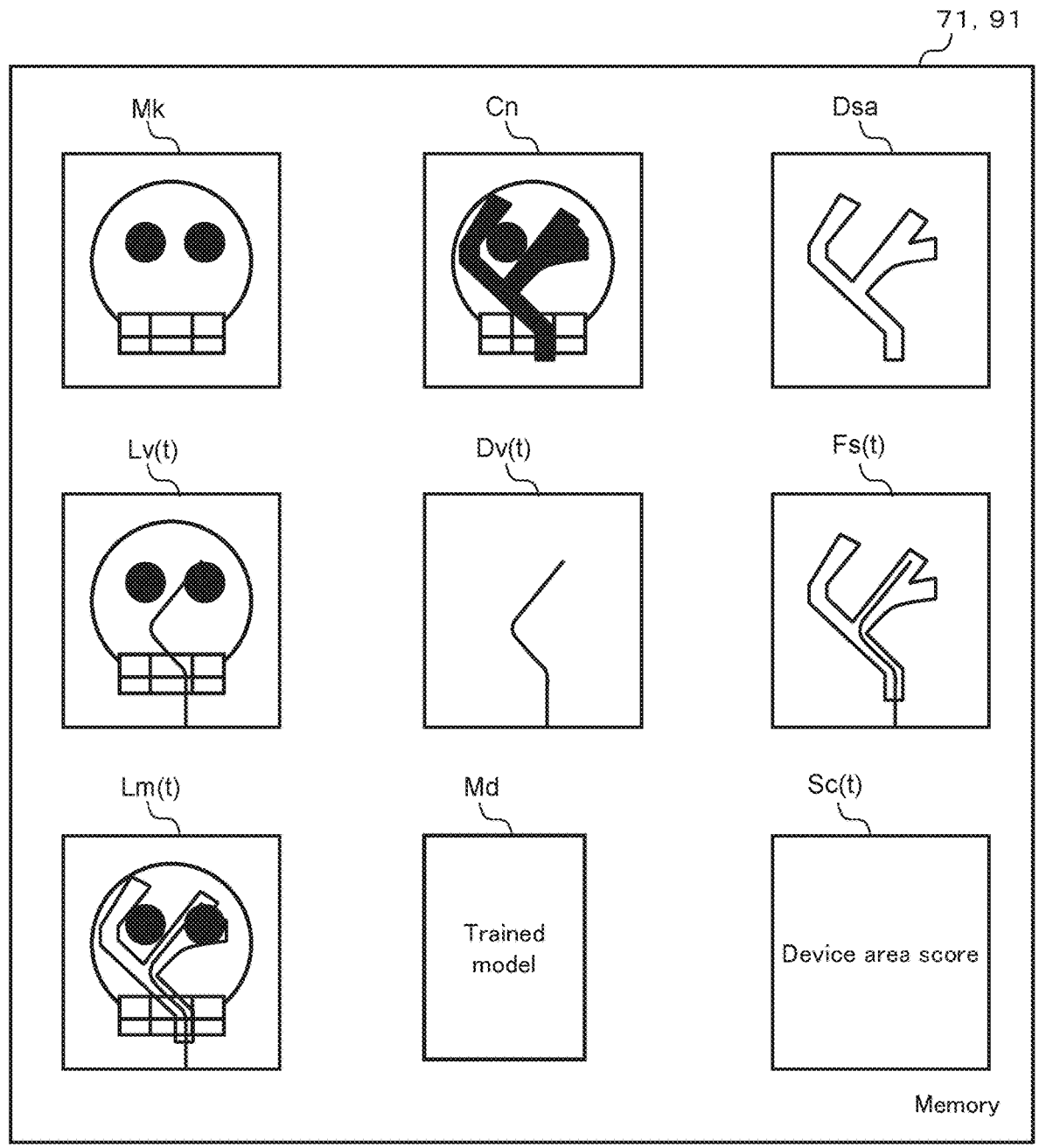
FIG. 3 is a schematic diagram for explaining one example of a memory according to the first embodiment.
Figure 4:
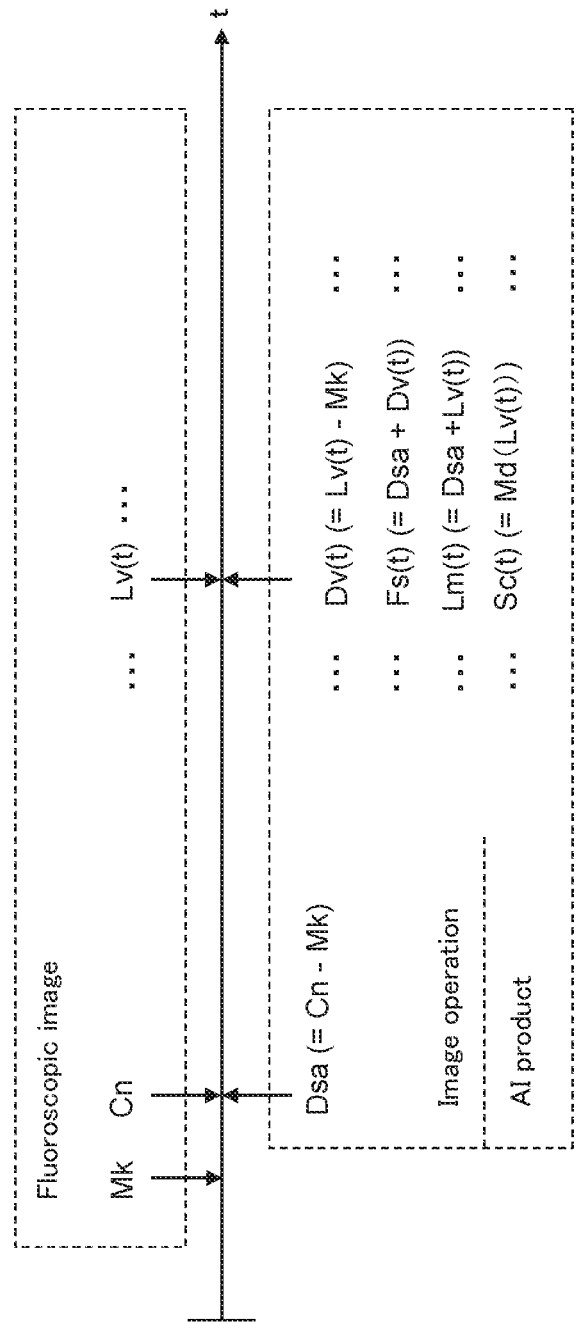
FIG. 4 is a schematic diagram for explaining each image, etc. stored in the memory according to the first embodiment.
Figure 5:
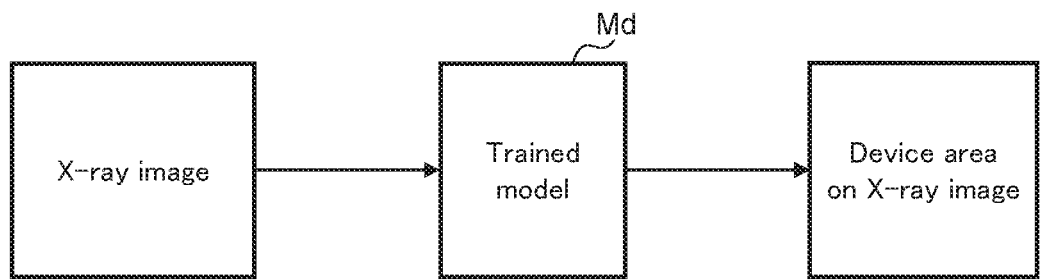
FIG. 5 is a schematic diagram for explaining a trained model according to the first embodiment.
Figure 6:
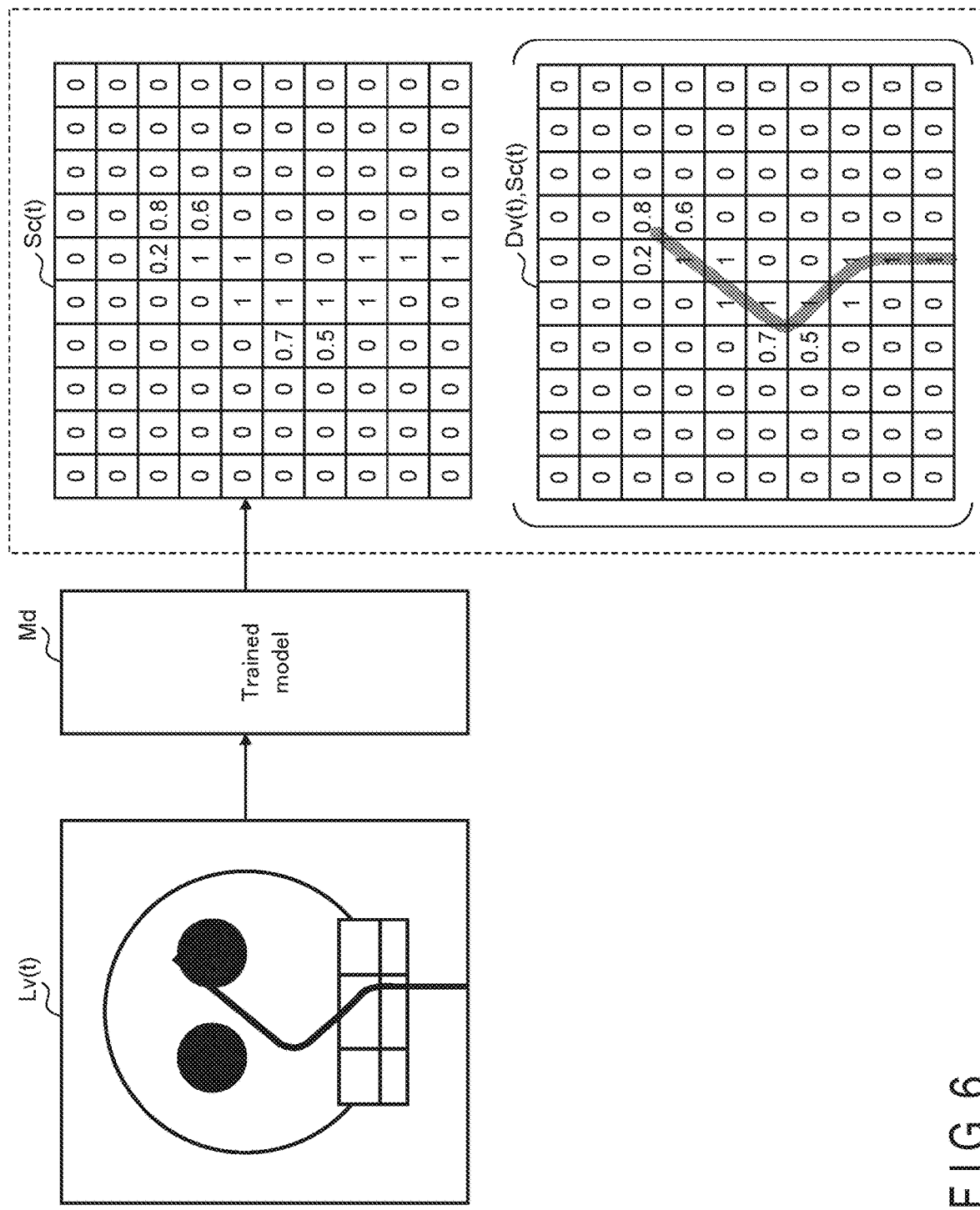
FIG. 6 is a schematic diagram for explaining an exemplary input and output of the trained model according to the first embodiment.
Figure 7:
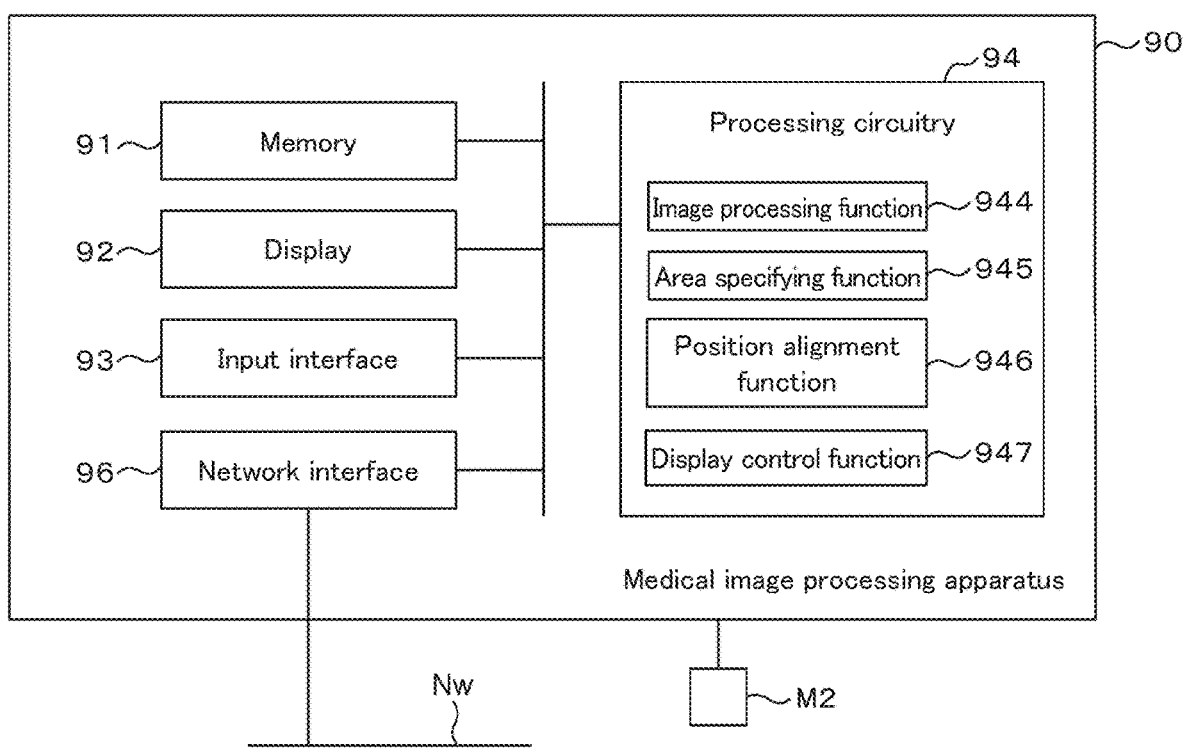
FIG. 7 is a block diagram showing a configuration of the medical image processing apparatus according to the first embodiment.

FIG. 1 is a block diagram showing a configuration of a medical image processing system according to the first embodiment, intended to include an X-ray diagnostic apparatus and a medical image processing apparatus. FIG. 2 is a block diagram showing a configuration of the X-ray diagnostic apparatus. FIGS. 3 and 4 are schematic diagrams for explaining a memory and each image. FIGS. 5 and 6 are schematic diagrams for explaining an example of a trained model and its exemplary input and output. FIG. 7 is a block diagram showing a configuration of the medical image processing apparatus. In the medical image processing system shown in FIG. 1, the X-ray diagnostic apparatus and the medical image processing apparatus, denoted respectively by 1 and 90, are provided so that they can communicate with each other via a network Nw.

The X-ray diagnostic apparatus 1 includes an imaging unit 10, an injector 40, a couch unit 50, and a console unit 70. The imaging unit 10 includes a high-voltage generator 11, an X-ray generator 12, an X-ray detector 13, a C-arm 14, a state detector 141, and a C-arm driver 142.

The high-voltage generator 11 is adapted to generate and output high voltages to an X-ray tube so that the high voltages are applied between an anode and a cathode of the X-ray tube in order to accelerate thermal electrons produced from the cathode.

The X-ray generator 12 is provided with this X-ray tube for radiating X-rays toward a subject P, and also an X-ray diaphragm having functions of delimiting the irradiation field of the X-rays, attenuating the X-rays for a portion of the irradiation fields, and so on.

The X-ray tube is adapted to generate X-rays. More specifically, the X-ray tube is a vacuum tube having a cathode for producing thermal electrons and an anode for receiving the thermal electrons flying from the cathode to generate X-rays. Examples of the X-ray tube include an X-ray tube of a rotating anode type, which generates X-rays by emitting thermal electrons to a rotating anode. The X-ray tube is connected to the high-voltage generator 11 through a high-voltage cable. The high-voltage generator 11 applies a tube voltage between the cathode and the anode. Upon this tube voltage application, thermal electrons depart from the cathode toward the anode. As the thermal electrons fly from the cathode toward the anode, a tube current flows. Thus, with the application of high voltage and the supply of filament current from the high-voltage generator 11, thermal electrons fly from the cathode to anode and collide with the cathode, whereby generating X-rays.

The X-ray diaphragm is arranged between the X-ray tube and the X-ray detector 13. The X-ray diaphragm typically employs diaphragm blades, as well as an added filter and a compensating filter. The X-ray diaphragm is adapted to limit the X-rays generated by the X-ray tube by blocking the X-ray paths except the area of opening so that the X-rays will be applied to only the region of interest of the subject P. For example, the X-ray diaphragm includes four diaphragm blades each constituted by a lead plate, and slide these diaphragm blades to adjust the X-ray shield area into a desired size. The diaphragm blades of the X-ray diaphragm may be driven by a driver (not illustrated) according to the region of interest input by an operator via a later-described input interface 73. The X-ray diaphragm also has a slit that can receive insertion of an added filter for adjusting the total filtration of X-rays. The X-ray diaphragm further has an accessory slot that can receive insertion of a lead mask or a compensating filter for use during X-ray inspection operations. The compensating filter may include a ROT (region of interest) filter having a function of attenuating or reducing the amount of X-ray radiation.

The X-ray detector 13 is adapted to detect X-rays transmitted through the subject P. This X-ray detector 13 may be a type that converts X-rays directly into electric charges, or a type that first converts X-rays into light and then converts the light into electric charges. The description will assume the former type, but the X-ray detector 13 may also be the latter type. Specifically, and for example, the X-ray detector 13 includes a planar, flat panel detector (FPD) for converting the X-rays transmitted through the subject P into electric charges to accumulate, and a gate driver for generating drive pulses for reading the electric charges accumulated in the FPD. The FPD includes micro sensor elements arranged two-dimensionally in the column direction and the line direction. The sensor elements each include a photoelectric film, a charge accumulation capacitor, and a thin film transistor (TFT). The photoelectric film senses X-rays and generates electric charges according to the amount of incident X-rays. The charge accumulation capacitor accumulates the electric charges generated at the photoelectric film. The TFT outputs, at predetermined timings, the electric charges accumulated at the charge accumulation capacitor. The accumulated electric charges are sequentially read with the drive pulses supplied from the gate driver.

While not illustrated, there are projection data generation circuitry and projection data storage circuitry arranged near or in the back part of the X-ray detector 13. The projection data generation circuitry includes a charge-voltage converter, an analog-digital (A/D) converter, and a parallel-serial converter. The charge-voltage converter converts the electric charges, read in units of rows or columns in a parallel manner from the FPD, into voltages. The A/D converter converts the output of this charge-voltage converter into digital signals. The parallel-serial converter converts the digitally-converted parallel signals into time-series serial signals. The projection data generation circuitry supplies these serial signals to the projection data storage circuitry as time-series projection data. The projection data storage circuitry sequentially stores the time-series projection data supplied from the projection data generation circuitry so that two-dimensional projection data is generated. The two-dimensional projection data is then stored in a memory 71.

The C-arm 14 is adapted to hold the X-ray generator 12 and the X-ray detector 13 in such a manner that they face each other with the subject P and a couch top 53 arranged therebetween, so that X-ray imaging of the subject P placed on the couch top 53 is enabled. By way of example, the following description will assume the C-arm 14 to be a type that is suspended from the ceiling, but this is not a limitation. The C-arm 14 may be, for example, a floor-mounted type.

As a more specific configuration, the C-arm 14 is adapted to be movable along the directions of the long axis and the short axis of the couch top 53. The C-arm 14 is supported by a support arm via a holding portion. The support arm is of a substantially arc shape and has a proximal end attached to a movement mechanism for a rail installation on the ceiling.

The C-arm 14 is held by the holding portion so that, in a certain state, it is rotatable about an axis extending in an X direction orthogonal to both a Y direction perpendicular to the couch top 53 and a Z direction along the long axis of the couch top 53. The C-arm 14 is of a substantially arc shape, which is concentric on the Z-direction axis, and held by the holding portion so that it is further slidable along the substantially arc shape. That is, the C-arm 14 is also capable of the sliding movement about the Z-direction axis. The C-arm 14, with the capability of said rotational movement about the X-direction axis through the holding portion ("main rotational movement") in combination with this sliding movement, can enable X-ray image observations at various angles and from various directions. The C-arm 14 may further be rotatable about the Y-direction axis whereby the center of the sliding movement coincides with, for example, the X-direction axis. Note that the focal point of the X-rays from the X-ray generator 12 and the imaging axis extending through the center of the X-ray detector 13's detection plane are designed to intersect each other at a single point that is on the axis as the center of the sliding movement and also on the axis as the center of the main rotational movement. Such a point of intersection is generally called an "isocenter". The isocenter is not displaced with the sliding movement or the main rotational movement of the C-arm 14. As such, once a concerned site is positioned at the isocenter, observation of the site through the moving medical images acquired from the C-arm 14's slicing movement or main rotational movement will be facilitated.

For the C-arm 14 of this configuration, multiple power sources are provided at suitable, applicable locations in order to realize the operations of the support arm under the rail installation, or the operations in the X-direction axis, the Y-direction axis, and the Z-direction axis. These power sources constitute the C-arm driver 142. The C-arm driver 142 reads drive signals from a later-described drive control function 742 to cause the C-arm 14 to perform sliding movement, rotational movement, linear movement, etc. The C-arm 14 is also provided with the state detector 141 for detecting each information about the angle or orientation, position, etc. of the C-arm 14. The state detector 141 includes, for example, a potentiometer for detecting a rotation angle, a movement amount, etc., an encoder as a position sensor, and so on. Examples of the available encoder includes a so-called absolute encoder of a magnetic type, a brush type, a photoelectric type, or the like. As the state detector 141, various position detecting mechanisms may also be discretionarily adopted, such as a rotary encoder outputting rotational displacement in the form of digital signals, or a linear encoder outputting linear displacement in the form of digital signals.

The injector 40 is adapted to inject a contrast medium to the subject P according to the injection amount and the injection rate communicated from a later-described imaging control function 743, at the time of taking a contrast-enhanced blood vessel X-ray image of the subject P.

The couch unit 50 is a unit adapted to movably carry the subject P, and includes a base 51, a couch driver 52, the aforementioned couch top 53, and a support frame 54.

The base 51 is a housing on the floor, and adapted to support the support frame 54 in such a manner that the support frame 54 can move vertically (in the Y direction).

The couch driver 52 may be disposed in the housing of the couch unit 50, and includes a motor or an actuator adapted to move the top 53, on which the subject P is placed, in the longitudinal direction of the couch top 53 (in the Z direction). The couch driver 52 reads drive signals from the drive control function 742 to cause the couch top 53 to move horizontally or vertically with respect to the floor face.

The couch top 53 is provided on the upper side of the support frame 54, and may be a plate adapted for placement of the subject P.

The support frame 54 is adapted to support the couch top 53 so that the couch top 53, on which the subject P is placed, can move. More specifically, the support frame 54 is provided at the upper portion of the base 51, and supports the couch top 53 so that the couch top 53 can slide in its longitudinal direction.

The console unit 70 includes the aforementioned memory 71 and input interface 73, as well as a display 72, processing circuitry 74, and a network interface 76.

The memory 71 includes a memory main component for storing electric information, such as a read only memory (ROM), a random access memory (RAM), a hard disk drive (HDD), an image memory, etc. The memory 71 also includes peripheral circuitry pertaining to the memory main component, such as a memory controller, a memory interface, etc. The memory 71 stores, for example, programs for execution by the processing circuitry 74, detection data (projection data) received from the X-ray detector 13, medical images generated by the processing circuitry 74, data for use in processing by the processing circuitry 74, various tables, data under processing, data after processing, and so on. For example, such medical images include, as shown in FIGS. 3 and 4, a mask image Mk, a contrast image Cn, a blood vessel image Dsa, a live image Lv(t), a device image Dv(t), a fluoroscopy subtraction image Fs(t), a fluoroscopy landmark image Lm(t), etc. Note that the symbol "(t)" indicates that the associated image is a frame image at respective time t, namely, the image constitutes time-series images having been taken in chronological order. The medical images are not limited to medical images for a head portion as illustrated in the figures, but may be medical images for any site that involves blood vessels for insertion of a device. By way of example, the description will assume the cases with medical images for a head portion.

The mask image Mk is a non-contrast X-ray image of a subject's treatment site before treatment procedures, and it is acquired by imaging the site without a contrast medium or after the injected contrast medium having flowed away. In this mask image Mk, a background such as bone of the subject appears.

The contrast image Cn is an X-ray image of a subject's treatment site before treatment procedures, and it is acquired by imaging the site with a contrast medium injected. The X-rays radiated from the X-ray tube largely change their intensity in the course of passing through the contrast medium present in the subject's blood vessels, and then enter the X-ray detector 13. In the contrast image Cn, accordingly, the subject's blood vessels appear together with a background such as the subject's bone.

The blood vessel image Dsa is an X-ray image obtained by performing position alignment (registration) and subtraction between the contrast image Cn and the mask image Mk. Upon the processing circuitry 74 performing the processing for subtraction (image operation) using the contrast image Cn and the mask image Mk, the background that equally appears in both the contrast image Cn and the mask image Mk, such as bone, disappears, while the blood vessels appearing only in the contrast image Cn stand out. Thus, only the blood vessels in the contrast image Cn are extracted and appear in the blood vessel image Dsa obtained after the subtraction. This blood vessel image Dsa may also be called a DSA image. As mentioned previously, "DSA" stands for digital subtraction angiography.

The live image Lv(t) is an X-ray image of a subject's treatment site under treatment procedures, and it is acquired by performing fluoroscopic imaging of the site with one or more treatment or inspection devices (e.g., catheter, coil, guide wire, etc.) in their inserted state. The X-rays radiated from the X-ray tube largely change their intensity in the course of passing through the devices, and then enter the X-ray detector 13. In the live image Lv(t), accordingly, the devices inserted into the subject appear together with a background such as the subject's bone. Such a live image Lv(t) is generated and displayed in real time. The term "real time" here does not indicate the processing of generating and displaying an image strictly at the moment of the imaging operation, but it is indicative of sequentially generating and displaying the live images Lv(t)'s by the processing circuitry 74 and the display 72.

The device image Dv(t) is an X-ray image obtained by performing position alignment and subtraction between the live image Lv(t) and the mask image Mk. Upon the processing circuitry 74 performing the processing for subtraction (image operation) using the live image Lv(t) and the mask image Mk, the background that equally appears in both the live image Lv(t) and the mask image Mk, such as bone, disappears, while the devices appearing only in the live image Lv(t) stand out. Thus, only the devices in the live image Lv(t) are extracted and appear in the device image Dv(t) obtained after the subtraction. Such a device image Dv(t) is generated in real time. The term "real time" here does not indicate the processing of image generation, etc. strictly at the moment of the imaging operation, but it is indicative of sequentially generating the device images Dv(t)'s subsequent to generating the respective live images Lv(t)'s.

The fluoroscopy subtraction image Fs(t) is an X-ray image obtained by performing position alignment and addition between the blood vessel image Dsa and the device image Dv(t). Upon the processing circuitry 74 performing the processing for addition (image operation) using the blood vessel image Dsa and the device image Dv(t), a superimposed image is produced, where the blood vessels having been extracted in the blood vessel image Dsa and the devices having been extracted in the device image Dv(t) are shown. The doctor proceeds with the intended treatment procedures while checking the positional relationship between the applicable blood vessel and device through the fluoroscopy subtraction images Fs(t)'s as a moving image generated and displayed in real time. The term "real time" here does not indicate the processing of generating and displaying an image strictly at the moment of the imaging operation, but it is indicative of sequentially generating and displaying the fluoroscopy subtraction images Fs(t)'s subsequent to generating the respective device images Dv(t)'s. Note that the foregoing description does not pose a limitation to the fluoroscopy subtraction image Fs(t), but the fluoroscopy subtraction image Fs(t) may be generated in real time by performing subtraction using the contrast image Cn and the live image Lv(t). Again, the term "real time" here is indicative of the processing of sequentially generating and displaying the fluoroscopy subtraction images Fs(t)'s subsequent to generating the respective live images Lv(t)'s.

The fluoroscopy landmark image Lm(t) is an X-ray image obtained by performing position alignment and addition between the blood vessel image Dsa and the live image Lv(t). Upon the processing circuitry 74 performing the processing for addition (image operation) using the blood vessel image Dsa and the live image Lv(t), a superimposed image is produced, where the blood vessels having been extracted in the blood vessel image Dsa and the background and devices appearing in the live image Lv(t) are shown. The doctor proceeds with the intended treatment procedures while checking the positional relationship between the applicable blood vessel and device in the background through the fluoroscopy landmark images Lm(t)'s as a moving image generated and displayed in real time. The term "real time" here does not indicate the processing of generating and displaying an image strictly at the moment of the imaging operation, but it is indicative of sequentially generating and displaying the fluoroscopy landmark images Lm(t)'s subsequent to generating the respective live images Lv(t)'s.

The memory 71 may additionally store a trained model Md, a device area score Sc(t), etc. For example, the memory 71 may already store the trained model Md before shipment of the X-ray diagnostic apparatus 1, or may acquire and store the trained model Md from a server device or the like (not illustrated) after the shipment of the X-ray diagnostic apparatus 1. This applies to all the following embodiments. The trained model Md has been trained to have a function of specifying, based on an X-ray image acquired with a device inserted into the subject, a device area on this X-ray image and outputting the specifying result. As the specifying result, the device area score Sc(t) may be adopted, which is indicative of an index value of the device area (may also be called "score") for each pixel in the live image Lv(t) aligned with the mask image Mk or other image as shown in, for one example, FIGS. 4 to 6. Note that the mask image Mk or other image here is a first X-ray image, and the live image Lv(t) here is a second X-ray image. This score may be a value for expressing the degree of likelihood of being a device (shape, X-ray absorbing capacity, etc.) in the range of from 0 to 1. The device area may be determined to be an area having a score of other than 0, or an area having a score equal to or greater than a reference value. The reference value may be any value discretionarily selected from the range of, for example, from 0.1 to 1. According to another exemplary implementation, the score may be two-valued, i.e., 0 or 1, so that the specified device area is expressed using 1 or 0. Note that, in FIG. 6, the superimposed image on the lower-right portion, which is based on the device area score Sc(t) and the device image Dv(t), is a schematic illustration for facilitating the understanding of the specifying result, and does not correspond to the pixel size of the live image Lv(t). Also, the specifying result for the device area is not limited to the foregoing description, but it may adopt a list of coordinate values indicating the device area or images indicating the device area.

Such a trained model Md may be a learned machine learning model that has been obtained by subjecting a machine learning model to a machine learning process using training data. The training data here includes a set of input data and output data, where the input data is X-ray images acquired with a device in its inserted state, and the output data is the specifying results for the device area on the respective X-ray images. The machine learning model is a parameterized composite function in which multiple functions are synthesized, and it is adapted to use, as an input, an X-ray image acquired with a device in the inserted state to output a specifying result for the device area on this X-ray image. The parameterized composite function is defined by the combination of multiple adjustable functions and parameters. The machine learning model according to this embodiment may adopt any parameterized composite functions as long as the above role is served, but the description will assume that the machine learning model here is a multi-layered network model (hereinafter, "multi-layered network"). The trained model Md adopting a multi-layered network includes an input layer for inputting an X-ray image, an output layer for outputting the result of specifying the device area on the X-ray image, and at least one middle layer provided between the input layer and the output layer. This trained model Md is expected to be utilized as a program module constituting part of artificial intelligence software. As the multi-layered network, for example, a deep neural network (DNN) which is a multi-layered neural network intended for deep learning is used. As the DNN, for example, a recurrent neural network (RNN) may be used for moving images, and a convolutional neural network (CNN) may be used for still images. The RNN may include a long short-term memory (LSTM). These explanation of the multi-layered network will likewise apply to all the machine learning models and trained models in the following description.

The program to store in the memory 71 include a program which, for example, causes a computer to realize an area specifying function of specifying, before position alignment between a first X-ray image and a second X-ray image which is acquired with a device inserted, a device area in the second X-ray image where the device is included, and a position alignment function of performing the position alignment using first processing of removing the specified device area or second processing of reducing a contribution of the device area. Note that such a program may be installed in advance in the computer from, for example, a network or a non-transitory computer-readable storage medium M1, so that the computer realizes each function of an internal medical image processing apparatus 77. Also, the functions of the medical image processing apparatus 77 disclosed herein may be realized as a computer-implemented method. The memory 71 is one example of a storage.

The display 72 includes a display main part for displaying various information including the medical images, etc., internal circuitry for supplying signals for display to the display main part, and peripheral circuitry including connectors, cables, or the like for connection between the display main part and the internal circuitry. The internal circuitry is adapted to generate display data by superimposing supplemental information, such as subject information and projection data generation conditions, on the image data given from the processing circuitry 74, and to subject the display data to D/A conversion and TV format conversion for display through the display main part. For example, the display 72 outputs medical images generated by the processing circuitry 74, graphical user interfaces (GUI's) for accepting various operations from an operator, and so on. For example, the display 72 may be a liquid crystal display or a cathode ray tube (CRT) display. Also, the display 72 may be a desktop type, or implemented as a tablet terminal, etc. capable of wireless communications with the main part of the console unit 70. The display 72 is one example of a display.

The input interface 73 enables input of subject information, setting of X-ray conditions, input of various command signals, and so on. The subject information includes, for example, a subject ID as well as a subject's name, date of birth, age, weight, gender, site for inspection, etc. The subject information may also include a subject's height. The input interface 73 is realized by components for providing, for example, instructions for movement of the C-arm 14, setting of a region of interest (ROI), etc., and such components include a trackball, switch buttons, a mouse, a keyboard, a touch pad which allows an input operation through contacting the operation screen, and a touch panel display which integrates a display screen and a touch pad. The input interface 73 is connected to the processing circuitry 74. The input interface 73 converts input operations received from operators into electric signals, and outputs the electric signals to the processing circuitry 74. The input interface 73 may instead be implemented as a tablet terminal, etc., capable of wireless communications with the main part of the console unit 70. In the present disclosure, the input interface 73 is not limited to physical operating components such as a mouse and a keyboard. That is, the examples of the input interface 73 also include processing circuitry for electrical signals that is adapted to receive an electrical signal corresponding to an input operation from an external input device separate from the apparatus, and to output this electrical signal to the processing circuitry 74.

The processing circuitry 74 is a processor adapted to read and execute programs in the memory 71 for realizing functions corresponding to the programs, including a system control function 741, the aforementioned drive control function 742, the aforementioned imaging control function 743, an image processing function 744, an area specifying function 745, a position alignment function 746, and a display control function 747. While FIG. 2 assumes that the processing circuitry 74 is a single circuitry element for realizing the system control function 741, the drive control function 742, the imaging control function 743, the image processing function 744, the area specifying function 745, the position alignment function 746, and the display control function 747, the processing circuitry may be constituted by a combination of multiple independent processors each running a program to realize the respective function. Also, the system control function 741, the drive control function 742, the imaging control function 743, the image processing function 744, the area specifying function 745, the position alignment function 746, and the display control function 747 may be called a system control circuit, a drive control circuit, an imaging control circuit, an image processing circuit, an area specifying circuit, a position alignment circuit, and a display control circuit, respectively, and they may be implemented as individual hardware circuits.

The system control function 741, for example, handles information, such as command signals or various initial setting and conditions input via the input interface 73 by an operator, in such a manner that it temporarily holds the information and then sends the information to respective, corresponding processing function of the processing circuitry 74.

The drive control function 742, for example, controls the C-arm driver 142 and the couch driver 52 using information input via the input interface 73 in relation to driving of the C-arm 14 and the couch top 53. For example, the drive control function 742 controls the movement and rotation in the imaging unit 10, the movement and tilt in the couch unit 50, etc.

The imaging control function 743, for example, controls X-ray conditions including a tube voltage from the high-voltage generator 11, a tube current, an irradiation time, etc., upon reading the information from the system control function 741. The X-ray conditions may include a product (mAS) of the tube current and the irradiation time.

The image processing function 744, for example, generates X-ray image data by subjecting projection data in the memory 71 to image processing such as filtering, and stores the X-ray image data in the memory 71. Examples of the X-ray image data generated from the projection data include medical image data such as the mask image Mk, the contrast image Cn, and the live image Lv(t). Further, the image processing function 744 performs processing for position alignment (e.g., APS), image operations (e.g., addition and subtraction processing), etc. between a multiple of the obtained X-ray image data, and stores the resultant X-ray image data in the memory 71. The position alignment may adopt APS, i.e., auto pixel shift, which is a technique of adjusting at least one of two images through rotation, distortion, shift, etc., so that the overlap between the two images is maximized (or the difference therebetween is minimized). Calculating the direction and distance in the auto pixel shift can be implemented in the manner as, for example, the following processing. Supposing that there are one mask image Mk and one live image Lv(t), the square value or the absolute value of the difference between corresponding pixels is calculated for each pixel unit, and the sum of such square values, etc. is used as an index value. The mask image Mk is then subjected to a predetermined degree of pixel shift processing, and the index value is calculated again using the mask image Mk after the pixel shift processing and the live image Lv(t). The calculation of the index value is repeated while changing the pixel-shifting direction and distance to various values, and the direction and distance that yield the minimum index value are obtained. The position with this minimum index value can be regarded as the position where the mask image Mk and the live image Lv(t) show the maximum overlap. Note that, for the present embodiment, the description will assume the instances of using such an index value for calculating the direction and distance in the pixel shift processing, but the method of calculating the direction and distance in the pixel shift processing is not limited to this. For example, the direction and distance in the pixel shift processing may be calculated by detecting a feature point appearing in both the mask image Mk and the live image Lv(t), and then obtaining a positional relationship between the feature point in one image and the feature point in the other image. The feature point in this method, however, should not adopt an inserted device. Examples of the X-ray image data generated by the position alignment and the image operations, etc. include medical image data such as the blood vessel image Dsa, the device image Dv(t), the fluoroscopy subtraction image Fs(t), and the fluoroscopy landmark image Lm(t). That is, the image processing function 744 may generate a fluoroscopy roadmap image based on the second X-ray image, i.e., the live image Lv(t), by performing the image operations after the position alignment. The position alignment here is performed in cooperation with the position alignment function 746. As the fluoroscopy roadmap image, for example, the fluoroscopy subtraction image Fs(t) or the fluoroscopy landmark image Lm(t) as discussed above may be adopted as appropriate. The image processing function 744 is one example of an image generator.

The area specifying function 745 specifies, before the position alignment between the first X-ray image and the second X-ray image acquired with a device inserted, a device area in the second X-ray image where the device is included. Here, the first X-ray image is, for example, the mask image Mk, and the second X-ray image is, for example, the live image Lv(t). The specified device area embraces the portions in the second X-ray image where the device appears, and it is an area smaller than the entire X-ray image. The specified device area may instead be called a specific area, a partial area, a sub-area, a concerned area, or the like. For specifying the device area, the area specifying function 745 may employ any technique including, for example, (i) a technique of using the trained model Md, (ii) a technique of using the blood vessel image Dsa, and (iii) a technique of using a threshold. These techniques (i) to (iii) are given only as examples, and the technique that can be employed by the area specifying function 745 is not limited to any of the techniques (i) to (iii). The techniques (i) to (iii), when employed, may be implemented independently or in any combination.

For the technique (i) of using the trained model Md, the X-ray diagnostic apparatus 1 includes the memory 71 storing the trained model Md having been trained to have a function of specifying, based on an X-ray image acquired with a device inserted, a device area on this X-ray image where the device is included, and outputting the specifying result. The area specifying function 745 specifies, based on the latest X-ray image out of the first X-ray image and the second X-ray image and using the trained model Md, a device area in the latest X-ray image. Note that, in the disclosure herein, the term "latest X-ray image" may be replaced with "just updated X-ray image" as appropriate, and more specifically, the expression "latest" may also be interpreted as "just updated". In the present embodiment, the latest live image Lv(t) corresponds to the latest X-ray image. Also, in the second embodiment as will be discussed, a just updated mask image Mk_dv and a latest live image Lv(t) each correspond to the latest X-ray image.

For the technique (ii) of using the blood vessel image Dsa, the X-ray diagnostic apparatus 1 includes the memory 71 storing the blood vessel image Dsa that can be superimposed on each of the first X-ray image and the second X-ray image. The area specifying function 745 according to this technique may realize any of the following functions (ii-a) to (ii-d).

(ii-a) A function of specifying the device area by detecting a device from the latest X-ray image out of the first X-ray image and the second X-ray image, based on a dilated blood vessel region in the blood vessel image Dsa, where the blood vessel region is expanded in its width direction. For example, the processing for this device detection may be performed by inputting the dilated blood vessel region and the latest X-ray image to the trained model Md according to the above technique (i). In this case, the techniques (i) and (ii) are combined for use.

(ii-b) A function of specifying the device area by detecting a device from the latest X-ray image out of the first X-ray image and the second X-ray image, based on a blood vessel region wider than a reference width among blood vessel regions or widthwise-expanded blood vessel regions in the blood vessel image Dsa. For example, the processing for this device detection may be performed by inputting the blood vessel region wider than the reference width and the latest X-ray image to the trained model Md according to the above technique (i). In this case, the techniques (i) and (ii) are combined for use.

(ii-c) A function similar to the function (ii-b) but using, in lieu of the blood vessel region wider than a reference width, a blood vessel region of a designated range.

(ii-d) A function similar to the function (ii-b) but using, in lieu of the blood vessel region wider than a reference width, a blood vessel region as a route to a treatment site.

For the technique (iii) of using a threshold, an area having a given value equal to or below the threshold in the latest X-ray image out of the first X-ray image and the second X-ray image is specified as the device area.

Note that, in addition to specifying the device area in the second X-ray image as discussed, the area specifying function 745 may specify the device area where a device is included, in also the first X-ray image acquired with this device inserted. The foregoing explanations of the device area likewise apply to the device area in the first X-ray image. For specifying the device area in the first X-ray image, the area specifying function 745 may likewise employ any technique including the technique (i) of using the trained model Md, the technique (ii) of using the blood vessel image Dsa, and the technique (iii) of using a threshold. Also, similarly, the technique that can be employed by the area specifying function 745 is not limited to any of the techniques (i) to (iii). The area specifying function 745 is one example of an area specifier.

The position alignment function 746 performs position alignment in cooperation with the image processing function 744, by using first processing of removing the device area specified by the area specifying function 745 or by using second processing of reducing a contribution of the device area.

Processing for the position alignment here may employ, for example, a first scheme or a second scheme. The first scheme includes performing the first processing or the second processing on an X-ray image in which a device area has been specified, calculating an index value of the amount of misalignment between the first X-ray image and the second X-ray image based on the X-ray image having been subjected to the first processing or the second processing, and shifting the first X-ray image or the second X-ray image based on the calculated index value.

The second scheme includes calculating an index value of the amount of misalignment between the first X-ray image and the second X-ray image using the first processing or the second processing, and shifting the first X-ray image or the second X-ray image based on the calculated index value.

The first processing and the second processing are for use in the preceding processing stage (e.g., processing of the input image according to the first scheme, or the calculation of the index value according to the second scheme) in the position alignment, and they are not used in the subsequent image shifting processing or the image operations after the position alignment. That is, the image shifting as the subsequent processing stage in the position alignment, as well as the image operations after the position alignment, will use a mask image, a live image, etc., which have not undergone either of the first processing and the second processing.

The first processing and the second processing each are a type of processing which may appropriately be (A) a processing type of modifying an input image that includes the device area, or (B) a processing type of altering the calculation of an index value of the misalignment amount for pixel values of the device area. In the processing type (A) of modifying an input image, the calculation of an index value of the misalignment amount is not altered. That is, according to the processing type (A), the existing APS technique may be adopted for calculating an index value of the amount of misalignment between images, and shifting the image or images based on the calculated index value. The input image may appropriately be an image in which a device area has been specified, among the mask images and the live images. In the processing type (B) of altering the calculation of an index value of the misalignment amount, the input images are not modified.

In the case of the type (A), the first processing may be erasing a device from the input image (e.g., processing of converting the device area into the background). More specifically, the first processing when being the type (A) is image processing to erase, from the X-ray image including a specified device area out of the first X-ray image and the second X-ray image, the device that appears in this device area. The first processing in this case (type (A)) may appropriately adopt, for example, (a11) replacing the pixel values of the device area in the input image with the pixel values of the peripheral pixels around the device area, or (a12) replacing the pixel values of the device area in the input image with the pixel values of the corresponding area in the mask image.

Also, in the case of the type (A), the second processing may be blurring a device in the input image. More specifically, the second processing when being the type (A) is image processing to blur, in the X-ray image including a specified device area out of the first X-ray image and the second X-ray image, the device that appears in this device area. The second processing in this case (type (A)) may appropriately adopt, for example, (a21) approximating the pixel values of the device area in the input image to the pixel values of the peripheral pixels around the device area at a certain rate, or (a22) approximating the pixel values of the device area in the input image to the pixel values of the corresponding area in the mask image at a certain rate.

On the other hand, in the case of the type (B), the first processing may be not using, or forgoing the use of, the pixel values of the specified device area, for the calculation of the index value of the amount of misalignment between two images. More specifically, the first processing when being the type (B) is processing to exclude the pixel values of the specified device area from the materials for calculating the index value of the amount of misalignment between the first X-ray image and the second X-ray image. On a note, the calculation of the index value may be such that the square value of the difference between corresponding pixels in two images is calculated for each pixel unit, and the sum of such square values is used as an index value. Here, the calculation may include, or omit, multiplying the square value of each pixel difference by a coefficient. In either way, the first processing in this case (type (B)) does not use the pixel values of the device area for the calculation of the misalignment amount, and therefore, the device area can be excluded.

The second processing when being the type (B) is processing to reduce a contribution of the pixel values of the specified device area in the calculation of the index value of the amount of misalignment between the first X-ray image and the second X-ray image. The second processing in the case of the type (B) may be, for example, in calculating the index value (that is, when the difference between corresponding pixels in two images is squared for each pixel unit, and the sum of such square values is used as the index value), setting a coefficient k for the square value of each pixel difference corresponding to the device area to be in the range of 0<k<1. If the sum of absolute values of the differences is adopted as the index value, a coefficient k for each of the absolute values corresponding to the device area may be set to the range of 0<k<1. The coefficient k may be a single value, or may be varied according to the device area scores Sc(t)'s corresponding to the respective pixels. The term "coefficient" is interchangeable with, for example, "weight" or "weight value". The term "second processing" is thus interchangeable with, for example, "weighting" or "weighting processing". Note that, if this second processing of the type (B) is modified to use the coefficient k=0, i.e., to minimize the contribution of the device area, the resultant effect will be equivalent to that obtained from the first processing of the type (B) where the device area is excluded from the calculation materials. That is, the second processing of the type (B) may be modified to cover the first processing of the type (B) above. The position alignment function 746 is one example of a position alignment processor.

The display control function 747, for example, performs control for causing the display 72 to present display data such as the medical image data stored in the memory 71. For example, the control, etc. performed by the display control function 747 include reading signals from the system control function 741, acquiring desired medical image data from the memory 71, and displaying the medical image data through the display 72. The display control function 747 is one example of a display controller.

The network interface 76 is circuitry for connecting the console unit 70 to the network Nw for communications with other entities or apparatuses such as the medical image processing apparatus 90. As the network interface 76, for example, a network interface card (NIC) may be adopted. In the following disclosure, such a description as the network interface 76 being involved in the communications with other entities or apparatuses will be omitted.

The memory 71, the display 72, the interface 73, and the processing circuitry 74 with the image processing function 744, the area specifying function 745, the position alignment function 746, and the display control function 747 as described above together constitute the medical image processing apparatus 77. Accordingly, the explanations of the memory 71, the display 72, and the interface 73, as well as the image processing function 744, the area specifying function 745, the position alignment function 746, and the display control function 747 of the processing circuitry 74 should be understood as explanations of the respective features in the X-ray diagnostic apparatus 1 and the medical image processing apparatus 77. The medical image processing apparatus 77 may be provided within the X-ray diagnostic apparatus 1, or may be provided as a discrete apparatus outside the X-ray diagnostic apparatus 1.

On the other hand, the medical image processing apparatus 90, which may be externally provided, includes a memory 91, a display 92, an input interface 93, processing circuitry 94, and a network interface 96, as shown in FIG. 7.

The memory 91 includes a memory main component for storing electric information, such as a ROM, a RAM, an HDD, an image memory, etc. The memory 71 also includes peripheral circuitry pertaining to the memory main component, such as a memory controller, a memory interface, etc. The memory 91 stores, for example, programs for execution by the processing circuitry 94, medical images generated by the processing circuitry 94, data for use in processing by the processing circuitry 94, various tables, data under processing, data after processing, and so on. For example, the medical images include the mask image Mk, the contrast image Cn, the blood vessel image Dsa, the live image Lv(t), the device image Dv(t), the fluoroscopy subtraction image Fs(t), the fluoroscopy landmark image Lm(t), etc., as shown in FIGS. 3 and 4. These images are each as described above.

The memory 91 may additionally store its trained model Md, device area score Sc(t), etc. The trained model Md and the device area score Sc(t) are each as described above. For example, the trained model Md has been trained to have a function of specifying, based on an X-ray image acquired with a device inserted into a subject, a device area on this X-ray image and outputting the specifying result. As the specifying result, the device area score Sc(t) may be adopted, which is indicative of an index value of the device area (score) for each pixel in the live image Lv(t) as the second X-ray image, as shown in FIGS. 4 to 6, for example. The program to store in the memory 91 include a program which, for example, causes a computer to realize the area specifying function of specifying, before position alignment between a first X-ray image and a second X-ray image which is acquired with a device inserted, a device area in the second X-ray image where the device is included, and the position alignment function of performing the position alignment using first processing of removing the specified device area or second processing of reducing a contribution of the device area. Note that such a program may be installed in advance in the computer from, for example, a network or a non-transitory computer-readable storage medium M2, so that the computer realizes each function of the medical image processing apparatus 90. Also, the functions of the medical image processing apparatus 90 disclosed herein may be realized as a computer-implemented method. The memory 91 is another example of the storage.

The display 92 includes a display main part for displaying various information including the medical images, etc., internal circuitry for supplying signals for display to the display main part, and peripheral circuitry including connectors, cables, or the like for connection between the display main part and the internal circuitry. The internal circuitry is adapted to generate display data by superimposing supplemental information, such as subject information and projection data generation conditions, on the image data given from the processing circuitry 94, and to subject the display data to D/A conversion and TV format conversion for display through the display main part. For example, the display 92 outputs medical images having undergone emphasis-adding processing by the processing circuitry 94, GUI's for accepting various operations from an operator, and so on. The display 92 may be a liquid crystal display or a CRT display, for example. Also, the display 92 may be a desktop type, or implemented as a tablet terminal, etc. capable of wireless communications with the main part of the medical image processing apparatus 90. The display 92 is another example of the display.

The input interface 93 enables, for example, input of subject information, various command signals, etc. For example, the subject information includes a subject ID, as well as a subject's name, date of birth, age, weight, gender, site for inspection, etc. The subject information may also include a subject's height. The input interface 93 is realized by elements for receiving, for example, instructions for medical image processing associated with machine learning, image processing, etc., setting of a region of interest (ROI), and so on, and examples of such elements include a trackball, switch buttons, a mouse, a keyboard, a touch pad which allows an input operation through contacting the operation screen, and a touch panel display which integrates a display screen and a touch pad. The input interface 93 is connected to the processing circuitry 94. The input interface 93 converts input operations received from operators into electric signals, and outputs the electric signals to the processing circuitry 94. The input interface 93 may instead be implemented as a tablet terminal, etc., capable of wireless communications with the main part of the medical image processing apparatus 90. In the present disclosure, the input interface 93 is not limited to physical operating components such as a mouse and a keyboard. That is, the examples of the input interface 93 also include processing circuitry for electrical signals that is adapted to receive an electrical signal corresponding to an input operation from an external input device separate from the apparatus, and to output this electrical signal to the processing circuitry 94.

The processing circuitry 94 is a processor adapted to read and execute programs in the memory 91 for realizing functions corresponding to the programs, including an image processing function 944, an area specifying function 945, a position alignment function 946, and a display control function 947. While FIG. 7 assumes that the processing circuitry 94 is a single circuitry element for realizing the image processing function 944, the area specifying function 945, the position alignment function 946, and the display control function 947, the processing circuitry may be constituted by a combination of multiple independent processors each running a program to realize the respective function. Also, the image processing function 944, the area specifying function 945, the position alignment function 946, and the display control function 947 may be called an image processing circuit, an area specifying circuit, a position alignment circuit, and a display control circuit, respectively, and they may be implemented as individual hardware circuits. Note that the image processing function 944, the area specifying function 945, the position alignment function 946, and the display control function 947 in the medical image processing apparatus 90 are functions equivalent to the image processing function 744, the area specifying function 745, the position alignment function 746, and the display control function 747 in the X-ray diagnostic apparatus 1. Therefore, the following description of the image processing function 944, the area specifying function 945, the position alignment function 946, and the display control function 947 will omit redundant explanatory portions, etc. as appropriate.

The image processing function 944, for example, stores X-ray image data received from the X-ray diagnostic apparatus 1, in the memory 91. Examples of the received X-ray image data include medical image data such as the mask image Mk, the contrast image Cn, and the live image Lv(t). Further, the image processing function 944 performs processing for position alignment (e.g., APS), image operations (e.g., addition and subtraction processing), etc. between a multiple of the X-ray image data in the memory 91, and stores the resultant X-ray image data in the memory 91. The position alignment may adopt the above-described auto pixel shift (APS). Calculating the direction and distance in the auto pixel shift can be implemented, for example, in the manner as described above. Similar to the above, also, examples of the X-ray image data generated by the position alignment and the image operations, etc. include medical image data such as the blood vessel image Dsa, the device image Dv(t), the fluoroscopy subtraction image Fs(t), and the fluoroscopy landmark image Lm(t). That is, the image processing function 944 may generate a fluoroscopy roadmap image based on the second X-ray image, i.e., the live image Lv(t), by performing the image operations after performing the position alignment in cooperation with the position alignment function 946. As the fluoroscopy roadmap image, for example, the fluoroscopy subtraction image Fs(t) or the fluoroscopy landmark image Lm(t) as discussed above may be adopted as appropriate. The image processing function 944 is another example of the image generator.

The area specifying function 945 specifies, before the position alignment between the first X-ray image and the second X-ray image acquired with a device inserted, a device area in the second X-ray image where the device is included. Here, the first X-ray image is, for example, the mask image Mk, and the second X-ray image is, for example, the live image Lv(t). The specified device area is as described above. For specifying the device area, the area specifying function 945 may employ any technique including, for example and as described above, (i) a technique of using the trained model Md, (ii) a technique of using the blood vessel image Dsa, and (iii) a technique of using a threshold. The technique that can be employed by the area specifying function 945 is not limited to any of the techniques (i) to (iii).

For the technique (i) of using the trained model Md, the medical image processing apparatus 90 includes the memory 91 storing the trained model Md having been trained to have a function of specifying, based on an X-ray image acquired with a device inserted, a device area on this X-ray image where the device is included, and outputting the specifying result. The area specifying function 945 specifies, based on the latest X-ray image out of the first X-ray image and the second X-ray image and using the trained model Md, a device area in the latest X-ray image.

For the technique (ii) of using the blood vessel image Dsa, the medical image processing apparatus 90 includes the memory 91 storing the blood vessel image Dsa that can be superimposed on each of the first X-ray image and the second X-ray image. The area specifying function 945 according to this technique may realize any of the following functions (ii-a) to (ii-d).

(ii-a) A function of specifying the device area by detecting a device from the latest X-ray image out of the first X-ray image and the second X-ray image, based on a dilated blood vessel region in the blood vessel image Dsa, where the blood vessel region is expanded in its width direction.

(ii-b) A function of specifying the device area by detecting a device from the latest X-ray image out of the first X-ray image and the second X-ray image, based on a blood vessel region wider than a reference width among blood vessel regions or widthwise-expanded blood vessel regions in the blood vessel image Dsa.

(ii-c) A function similar to the function (ii-b) but using, in lieu of the blood vessel region wider than a reference width, a blood vessel region of a designated range.

(ii-d) A function similar to the function (ii-b) but using, in lieu of the blood vessel region wider than a reference width, a blood vessel region as a route to a treatment site.

For the technique (iii) of using a threshold, an area having a given value equal to or below the threshold in the latest X-ray image out of the first X-ray image and the second X-ray image is specified as the device area.

In addition to specifying the device area in the second X-ray image as discussed, the area specifying function 945 may specify the device area where a device is included, in also the first X-ray image acquired with this device inserted. The above explanations of the device area likewise apply to the device area in the first X-ray image. Also, for specifying the device area in the first X-ray image, the area specifying function 945 may likewise employ any technique including the technique (i) of using the trained model Md, the technique (ii) of using the blood vessel image Dsa, and the technique (iii) of using a threshold. Similarly, the technique that can be employed here by the area specifying function 945 is not limited to any of the techniques (i) to (iii). The area specifying function 945 is another example of the area specifier.

The position alignment function 946 performs position alignment in cooperation with the image processing function 944, by using first processing of removing the device area specified by the area specifying function 945 or by using second processing of reducing a contribution of the device area.

Processing for the position alignment here may employ, for example and as described above, a first scheme or a second scheme. The first scheme includes performing the first processing or the second processing on an X-ray image in which a device area has been specified, calculating an index value of the amount of misalignment between the first X-ray image and the second X-ray image based on the X-ray image having been subjected to the first processing or the second processing, and shifting the first X-ray image or the second X-ray image based on the calculated index value.

The second scheme includes calculating an index value of the amount of misalignment between the first X-ray image and the second X-ray image using the first processing or the second processing, and shifting the first X-ray image or the second X-ray image based on the calculated index value.

The first processing and the second processing are for use in the preceding processing stage (e.g., processing of the input image according to the first scheme, or the calculation of the index value according to the second scheme) in the position alignment, and they are not used in the subsequent image shifting processing or the image operations after the position alignment. That is, the image shifting as the subsequent processing stage in the position alignment, as well as the image operations after the position alignment, will use a mask image, a live image, etc., which have not undergone either of the first processing and the second processing.

The first processing and the second processing each are a type of processing which may appropriately be (A) a processing type of modifying an input image that includes the device area, or (B) a processing type of altering the calculation of an index value of the misalignment amount for pixel values of the device area. In the processing type (A) of modifying an input image, the calculation of an index value of the misalignment amount is not altered. That is, according to the processing type (A), the existing APS technique may be adopted for calculating an index value of the amount of misalignment between images, and shifting the image or images based on the calculated index value. The input image may appropriately be an image in which a device area has been specified, among the mask images and the live images. In the processing type (B) of altering the calculation of an index value of the misalignment amount, the input images are not modified.

In the case of the type (A), the first processing may be erasing a device from the input image (e.g., processing of converting the device area into the background). More specifically, the first processing when being the type (A) is image processing to erase, from the X-ray image including a specified device area out of the first X-ray image and the second X-ray image, the device that appears in this device area. The first processing in this case (type (A)) may appropriately adopt, for example, (a11) replacing the pixel values of the device area in the input image with the pixel values of the peripheral pixels around the device area, or (a12) replacing the pixel values of the device area in the input image with the pixel values of the corresponding area in the mask image.

Also, in the case of the type (A), the second processing may be blurring a device in the input image (e.g., processing of lightening the device area, or making the device area semitransparent). More specifically, the second processing when being the type (A) is image processing to blur, in the X-ray image including a specified device area out of the first X-ray image and the second X-ray image, the device that appears in this device area. The second processing in this case (type (A)) may appropriately adopt, for example, (a21) approximating the pixel values of the device area in the input image to the pixel values of the peripheral pixels around the device area at a certain rate, or (a22) approximating the pixel values of the device area in the input image to the pixel values of the corresponding area in the mask image at a certain rate.

On the other hand, in the case of the type (B), the first processing may be not using, or forgoing the use of, the pixel values of the specified device area, for the calculation of the index value of the amount of misalignment between two images. More specifically, the first processing when being the type (B) is processing to exclude the pixel values of the specified device area from the materials for calculating the index value of the amount of misalignment between the first X-ray image and the second X-ray image. On a note, the calculation of the index value may be such that the square value of the difference between corresponding pixels in two images is calculated for each pixel unit, and the sum of such square values is used as an index value. Here, the calculation may include, or omit, multiplying the square value of each pixel difference by a coefficient. In either way, the first processing in this case (type (B)) does not use the pixel values of the device area for the calculation of the misalignment amount, and therefore, the device area can be excluded.

The second processing when being the type (B) is processing to reduce a contribution of the pixel values of the specified device area in the calculation of the index value of the amount of misalignment between the first X-ray image and the second X-ray image. The second processing in the case of the type (B) may be, for example, in calculating the index value (that is, when the difference between corresponding pixels in two images is squared for each pixel unit, and the sum of such square values is used as the index value), setting a coefficient k for the square value of each pixel difference corresponding to the device area to be in the range of $0<k<1$. If the sum of absolute values of the differences is adopted as the index value, a coefficient k for each of the absolute values corresponding to the device area may be set to the range of $0<k<1$. The coefficient k may be a single value, or may be varied according to the device area scores $Sc(t)$'s corresponding to the respective pixels. The terms "coefficient" and "second processing" can each be replaced with other terms, as discussed above. Note that, if this second processing of the type (B) is modified to use the coefficient k=0, i.e., to minimize the contribution of the device area, the resultant effect will be equivalent to that obtained from the first processing of the type (B) where the device area is excluded from the calculation materials. That is, the second processing of the type (B) may be modified to cover the first processing. The position alignment function 946 is another example of the position alignment processor.

The display control function 947, for example, performs control for causing the display 92 to present display data such as the medical image data stored in the memory 91. For example, the control, etc. performed by the display control function 947 include reading signals from the input interface 93, acquiring desired medical image data from the memory 91, and displaying the medical image data through the display 92. The display control function 947 is another example of the display controller.

The network interface 96 is circuitry for connecting the medical image processing apparatus 90 to the network Nw for communications with other entities or apparatuses such as the X-ray diagnostic apparatus 1. As the network interface 96, for example, a network interface card (NIC) may be adopted. In the following disclosure, such a description as the network interface 96 being involved in the communications with other entities or apparatuses will be omitted.

Note that the image processing function 944, the area specifying function 945, the position alignment function 946, and the display control function 947 in the medical image processing apparatus 90 are functions equivalent to the image processing function 744, the area specifying function 745, the position alignment function 746, and the display control function 747 in the X-ray diagnostic apparatus 1. In other words, the medical image processing system as a whole may make use of the operations of any of the functions in the medical image processing apparatus 90 or the functions in the X-ray diagnostic apparatus 1.

Figure 8:
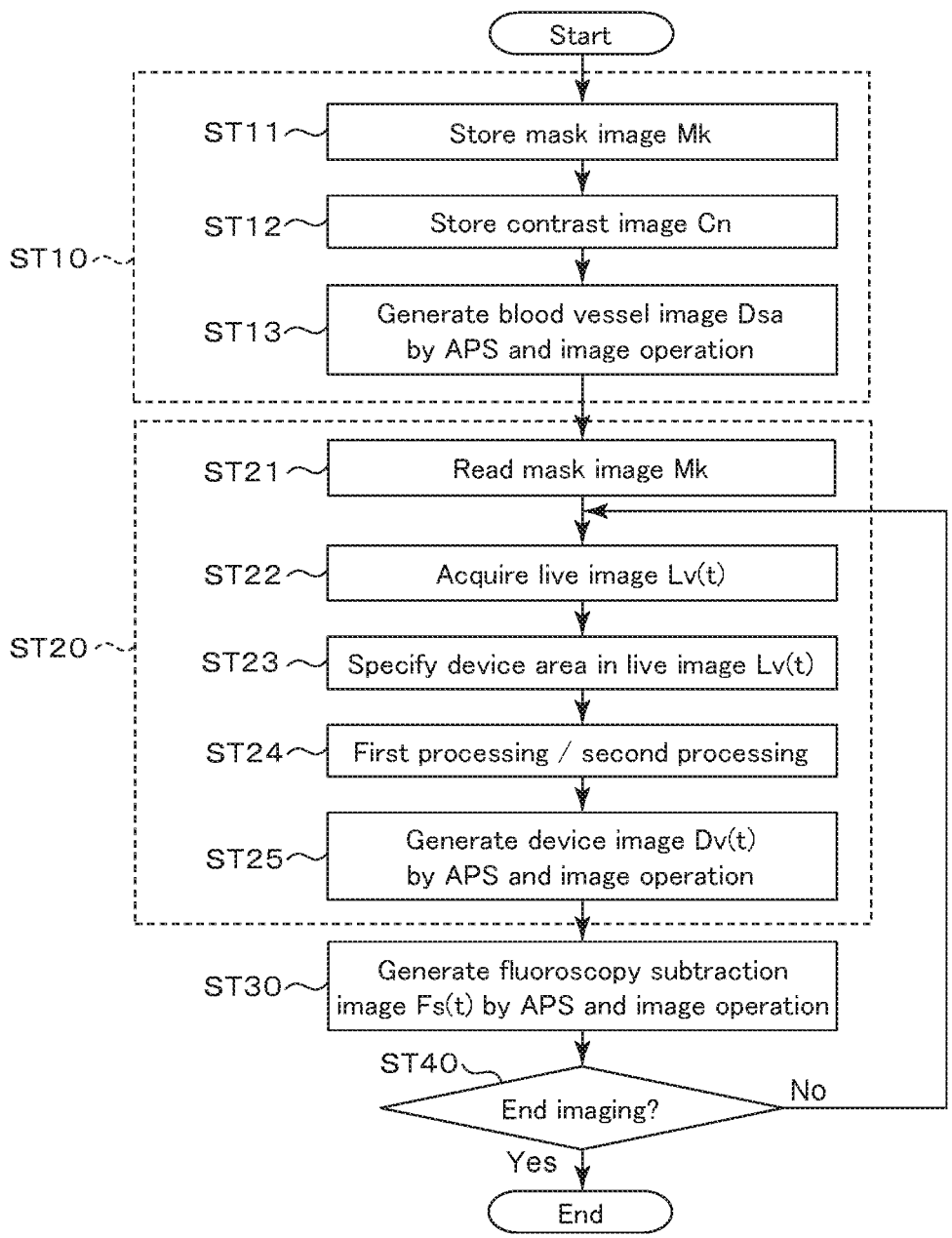
FIG. 8 is a flowchart for explaining operations in the first embodiment.
Figure 9:
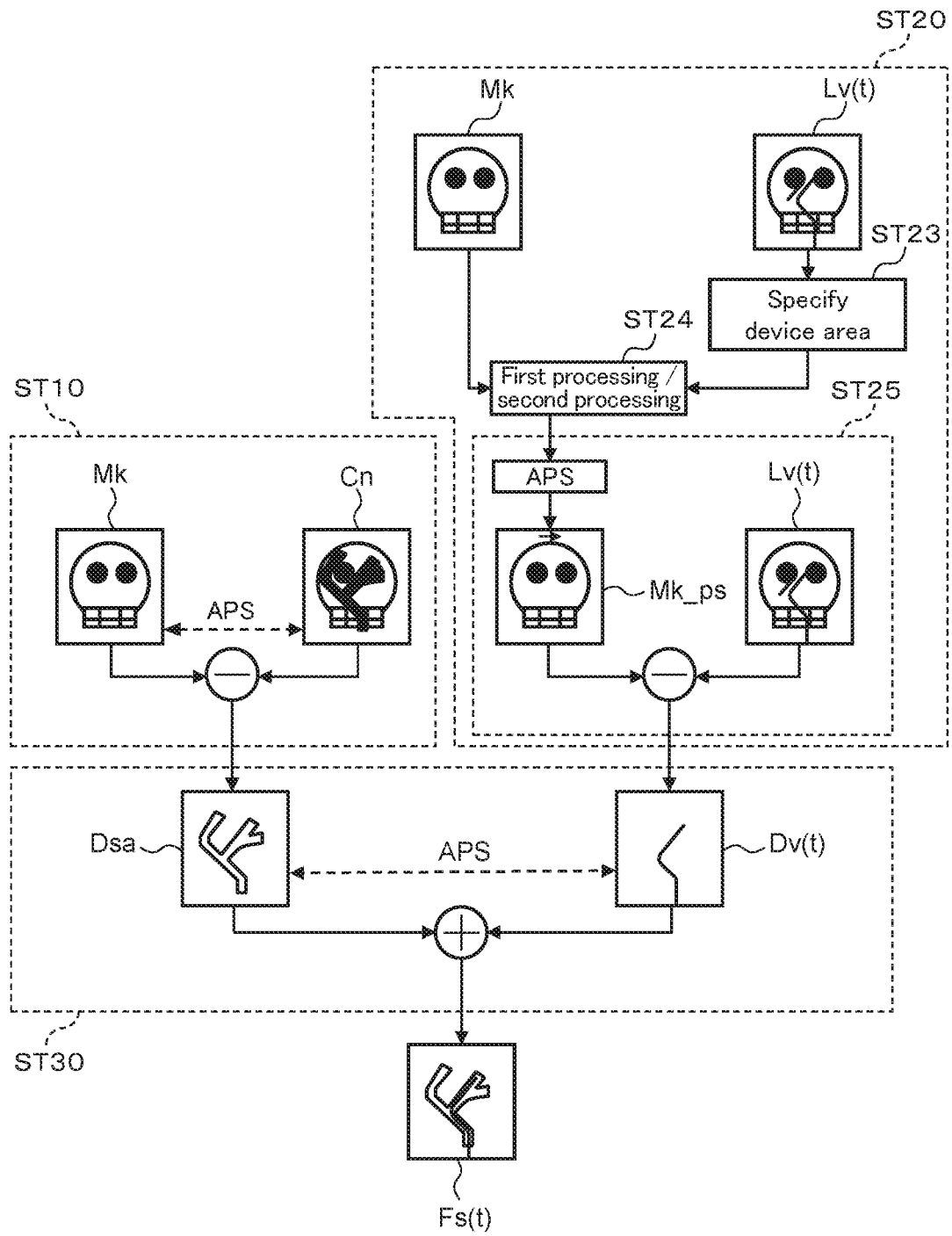
FIG. 9 is a schematic diagram for explaining a process of generating a fluoroscopy subtraction image in the first embodiment.

Now, how the medical image processing system configured as above operates will be described with reference to the flowchart in FIG. 8 and the schematic diagram in FIG. 9. Note that the processing circuitry 74 of the X-ray diagnostic apparatus 1 and the processing circuitry 94 of the medical image processing apparatus 90 are to perform substantially the same operations for the image processing function, the area specifying function, the position alignment function, and the display control function. Thus, in order to avoid redundant expressions and facilitate the understanding, the following description about the operations of the respective functions will assume, as a representative example, the case with the processing circuitry 94 of the medical image processing apparatus 90. The description of the representative example as such can be applied to the operations of the processing circuitry 74 of the X-ray diagnostic apparatus 1, if the apparatus name, reference symbols, etc. are appropriately replaced. This is also true of each embodiment and modification set forth below. The description will also assume the instance where the memory 91 in the medical image processing apparatus 90 already stores the trained model Md which has been trained to have a function of specifying, based on an X-ray image acquired with a device inserted, a device area on this X-ray image and outputting the specifying result.

In step ST10, the medical image processing apparatus 90 acquires a mask image Mk, a contrast image Cn, and a blood vessel image Dsa, and stores the mask image Mk, the contrast image Cn, and the blood vessel image Dsa in the memory 91. This step ST10 includes, for example, performing processing steps ST11 to ST13.

In step ST11, the processing circuitry 74 of the X-ray diagnostic apparatus 1 controls the imaging unit 10 to start X-ray fluoroscopic imaging, in response to an operator operating the input interface 73. Accordingly, an X-ray image of, for example, the head portion of a subject P is acquired as a moving image. The X-ray image corresponds to the live image Lv(t) which is ongoingly transmitted from the X-ray diagnostic apparatus 1 to the medical image processing apparatus 90 during the X-ray fluoroscopic imaging. Note that, at this point, a device has not been inserted into the subject P yet, and the live image Lv(t) does not show the device. The processing circuitry 94 of the medical image processing apparatus 90 stores the received live image Lv(t) in the memory 91 while causing the display 92 to display the same. The processing circuitry 74 of the X-ray diagnostic apparatus 1 here controls the imaging unit 10 according to the operator's operation on the input interface 73 so that the mask image Mk is acquired without a contrast medium flowing in the blood vessels. This mask image Mk is transmitted from the X-ray diagnostic apparatus 1 to the medical image processing apparatus 90. The processing circuitry 94 of the medical image processing apparatus 90 stores the received mask image Mk in the memory 91.

After step ST11, step ST12 is performed where the contrast medium is injected into the blood vessels through a catheter from the injector 40, and the contrast image Cn is acquired in this state. This contrast image Cn is transmitted from the X-ray diagnostic apparatus 1 to the medical image processing apparatus 90. The processing circuitry 94 of the medical image processing apparatus 90 stores the received contrast image Cn in the memory 91. Steps ST11 and ST12 may be performed in reverse order.

After step ST12, step ST13 is performed where the processing circuitry 94 performs the position alignment (APS) and the image operation (subtraction) between the mask image Mk and the contrast image Cn to generate the blood vessel image Dsa. This blood vessel image Dsa is stored in the memory 91. Step ST10 is complete upon performing such steps ST11 to ST13.

After step ST10, the device is inserted into the blood vessel of the subject P to start treatment procedures. Accordingly, in step ST20, the medical image processing apparatus 90 generates a device image Dv(t) from the mask image Mk and the live image Lv(t), and stores the device image Lv(t) in the memory 91. This step ST20 includes, for example, performing processing steps ST21 to ST25.

In step ST21, the processing circuitry 94 reads the mask image Mk from the memory 91.

After step ST21, step ST22 is performed where the processing circuitry 94 acquires from the X-ray diagnostic apparatus 1 the live image Lv(t) that has been obtained with the device inserted, and stores this live image Lv(t) in the memory 91 while causing the display 92 to display the same. Here, the live image Lv(t) is assumed to be, for example, as shown in the upper-right portion of FIG. 9, i.e., the one obtained in the state where the device inserted into the blood vessel overlaps the edge of the bone.

After step ST22, step ST23 is performed where the processing circuitry 94 specifies in the live image Lv(t) the device area where the device is included, in advance of the position alignment between the mask image Mk and the live image Lv(t). For example, the processing circuitry 94 may specify the device area in the live image Lv(t), based on the live image Lv(t) as the latest image out of the mask image Mk and the live image Lv(t) and using the trained model Md. Alternatively or additionally, the processing circuitry 94 may specify the device area by detecting the device from the live image Lv(t) based on a dilated blood vessel region in the blood vessel image Dsa read from the memory 91, where the blood vessel region is expanded in its width direction. Also, as still another alternative or additional option, the processing circuitry 94 may specify the device area by detecting the device from the live image Lv(t) based on a blood vessel region wider than a reference width among blood vessel regions or widthwise-expanded blood vessel regions in the blood vessel image Dsa. The processing circuitry 94 here may use, in lieu of the blood vessel region wider than a reference width, a blood vessel region of a designated range. The processing circuitry 94 may instead use, in lieu of the blood vessel region wider than a reference width, a blood vessel region serving as a route to a treatment site such as an aneurysm. As yet another alternative or additional option, the processing circuitry 94 may specify the area having a given value equal to or below the threshold in the live image Lv(t), as the device area. The device area in the live image Lv(t) is thus specified in any manner.

After step ST23, steps ST24 to ST25 are performed where the processing circuitry 94 uses the first processing of removing the specified device area or the second processing of reducing a contribution of the device area for performing the position alignment (APS or altered APS). The description here will assume an exemplary case of performing the position alignment according to the first scheme to modify the image.

In step ST24, for example, the processing circuitry 94 subjects the device area-specified X-ray image out of the mask image Mk and the live image Lv(t), to the first processing or the second processing. The first processing is image processing to erase the device appearing in the device area from the X-ray image, and the second processing is image processing to blur the device appearing in the device area in the X-ray image.

In step ST25 after step ST24, the processing circuitry 94 calculates the index value of the amount of misalignment between the device area-removed, or the device area-reduced live image Lv(t) and the mask image Mk, and performs the processing (APS) of shifting the live image Lv(t) and/or the mask image Mk to minimize the calculated index value. Then, the processing circuitry 94 performs the image operation (subtraction) between, for example, the mask image Mk_ps obtained after the shift and the live image Lv(t) to generate the device image Dv(t). Upon performing such steps ST21 to ST25, step ST20 is complete.

After step ST20, step ST30 is performed where the processing circuitry 94 performs the position alignment (APS) and the image operation (addition) between the blood vessel image Dsa generated in step ST10 and the device image Dv(t) generated in step ST20. The processing circuitry 94 thereby generates a fluoroscopy subtraction image Fs(t), and causes the display 92 to display this fluoroscopy subtraction image Fs(t). This enables a doctor, etc. to advance the device while viewing the fluoroscopy subtraction image Fs(t) and the live image Lv(t) displayed in real time, and to treat the intended treatment site in the blood vessels. Note that the real-time display here does not indicate the processing of displaying images strictly at each moment of their imaging, but it is indicative of the processing where the medical image processing apparatus 90 sequentially displays live images Lv(t)'s as well as the fluoroscopy subtraction images Fs(t)'s generated from the respective live images Lv(t)'s, in parallel with the X-ray diagnostic apparatus 1 sequentially acquiring these live images Lv(t)'s.

After step ST30, step ST40 is performed where the processing circuitry 94 determines whether or not an instruction for ending the imaging operation is input. If it is determined that the instruction for ending the imaging operation is not input, the processing returns to step ST22 and continues with steps ST22 to ST40. If it is determined that the instruction for ending the imaging operation is input, the processing is terminated.

According to the first embodiment as described above, in advance of the position alignment between the first X-ray image (mask image Mk) and the second X-ray image (live image Lv(t)) which is acquired with a device inserted, the device area where the device is included is specified in the second X-ray image. Also, the position alignment including the first processing of removing the specified device area or the second processing of reducing a contribution of the device area is performed. With the configuration in this manner of removing the device area or reducing the contribution of the device area for performing the position alignment, the first embodiment can suppress the errors in the position alignment between the images, which can occur due to the movement of the device during the fluoroscopic imaging. Moreover, the first embodiment can suppress the errors in the position alignment between the images, which can occur also due to the edge of bone, etc. in the mask image Mk interfering the device and the edge of bone, etc. in the live image Lv(t).

According to the first embodiment, the first processing is image processing to erase, from the X-ray image including a specified device area out of the first X-ray image and the second X-ray image, the device that appears in this device area. The second processing is image processing to blur, in the X-ray image including a specified device area out of the first X-ray image and the second X-ray image, the device that appears in this device area. The position alignment includes performing the first processing or the second processing on the X-ray image including the specified device area, calculating an index value of the amount of misalignment between the first X-ray image and the second X-ray image based on the X-ray image having been subjected to the first processing or the second processing, and shifting the first X-ray image or the second X-ray image based on the calculated index value. With this configuration, the first embodiment can make use of the existing APS technique upon modifying the X-ray image by the first processing or the second processing.

Note that, in the context of the first embodiment, use of such a first scheme of subjecting the X-ray image to the first processing or the second processing may be replaced with use of the second scheme of altering the calculation of the index value. According to the second scheme, the first processing is excluding the pixel values of the specified device area from the materials for calculating the index value of the amount of misalignment between the first X-ray image and the second X-ray image. The second processing is reducing the contribution of the pixel values of the specified device area in the calculation of the index value. The position alignment includes calculating the index value of the amount of misalignment between the first X-ray image and the second X-ray image using the first processing or the second processing, and shifting the first X-ray image or the second X-ray image based on the calculated index value. As per the alteration in the index value calculation, the term "APS" in step ST25 in FIGS. 8 and 9 is replaced with "altered APS". The position alignment according to the second scheme in this manner can likewise provide, aside from the capability of making use of the existing APS technique according to the first scheme, the advantages of suppressing the errors in the position alignment as described above.

According to the first embodiment, further, the trained model Md may be stored, which has been trained to have a function of specifying, based on an X-ray image acquired with a device inserted, the device area in the X-ray image where the device is included, and outputting the specifying result. Also, the device area in the latest X-ray image out of the first X-ray image and the second X-ray image may be specified based on the latest X-ray image and using the trained model Md. With this configuration, use of the trained model allows the device area to be easily specified.

According to the first embodiment, a blood vessel image that can be superimposed on each of the first X-ray image (mask image Mk) and the second X-ray image (live image Lv(t)) may be stored. The device area may be specified by detecting a device from the latest X-ray image based on a dilated blood vessel region in this blood vessel image, where the blood vessel region is expanded in its width direction. With this configuration, the device area can be specified based on the dilated blood vessel region expanded in the width direction, even when the position of the blood vessel is varied to some extent due to the inserted device.

According to the first embodiment, a blood vessel image that can be superimposed on each of the first X-ray image and the second X-ray image may be stored. The device area may be specified by detecting a device from the latest X-ray image based on a blood vessel region wider than a reference width among blood vessel regions or widthwise-expanded blood vessel regions in this blood vessel image. With this configuration, the device can be detected based on the blood vessel region showing a width greater than the reference width, while excluding the blood vessel regions equal to or narrower than the reference width (unrelated blood vessel regions) such as peripheral blood vessels, and therefore, the burden of the processing of specifying the device area can be mitigated.

Also, according to the first embodiment here, a blood vessel region of a designated range may be used in lieu of the blood vessel region wider than a reference width. With this configuration, the device can be detected based on the blood vessel region falling within the designated range, while excluding the blood vessel regions of the non-designated range (unrelated blood vessel regions), and therefore, the burden of the processing of specifying the device area can be mitigated.

Further, according to the first embodiment here, a blood vessel region serving as a route to a treatment site may be used in lieu of the blood vessel region wider than a reference width. With this configuration, the device can be detected based on the blood vessel region as a route to the treatment site, while excluding the blood vessel regions deviating from the route to the treatment site (unrelated blood vessel regions), and therefore, the burden of the processing of specifying the device area can be further mitigated.

According to the first embodiment, an area having a given value equal to or below the threshold in the X-ray image may be specified as the device area. With this configuration, the device area can be specified through the simple determination of whether or not the value for the area is equal to or below the threshold.

According to the first embodiment, a fluoroscopy roadmap image (fluoroscopy subtraction image Fs(t)) based on the second X-ray image (live image Lv(t)) may be generated by performing the position alignment and the image operation upon specifying the device area. This configuration utilizes the position alignment that reduces or does not involve the errors discussed earlier, and therefore, the first embodiment enables the generation of fluoroscopy roadmap images while suppressing the occurrence of artifacts.

(Modification)

A modification of the first embodiment will be described. The description will use same reference symbols for the components or operational features of the same, or substantially the same, contents that appear in the already discussed drawings. The description will in principle omit the details of such components, etc., and concentrate on the portions differing from the foregoing embodiment. Each of the following embodiments and modifications will be described in the same manner.

The first embodiment has been described as generating the fluoroscopy subtraction image Fs(t) as the fluoroscopy roadmap image. The modification of the first embodiment is the case of generating a fluoroscopy landmark image Lm(t) as the fluoroscopy roadmap image, as shown in FIGS. 10 and 11.

Accordingly, the processing circuitry 94 with the image processing function 944 does not generate the above-described device image Dv(t). The processing circuitry 94 instead subjects a blood vessel image Dsa_ps, obtained through the pixel-shift processing of a blood vessel image Dsa, and a live image Lv(t) to the image operation (addition). The fluoroscopy landmark image Lm(t) is thus generated.

The remaining aspects are the same as the first embodiment.

Figure 10:
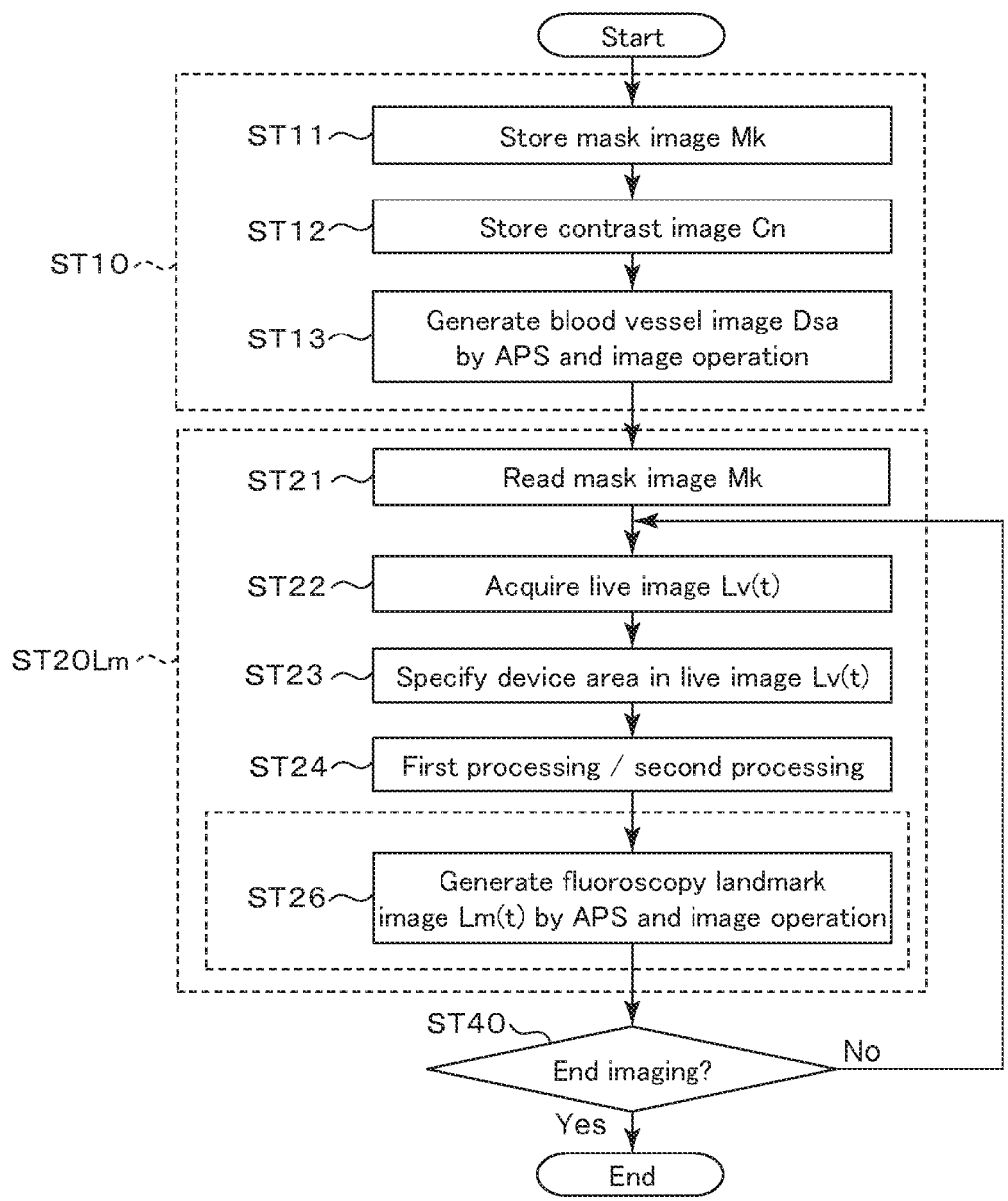
FIG. 10 is a flowchart for explaining operations in a modification of the first embodiment.
Figure 11:
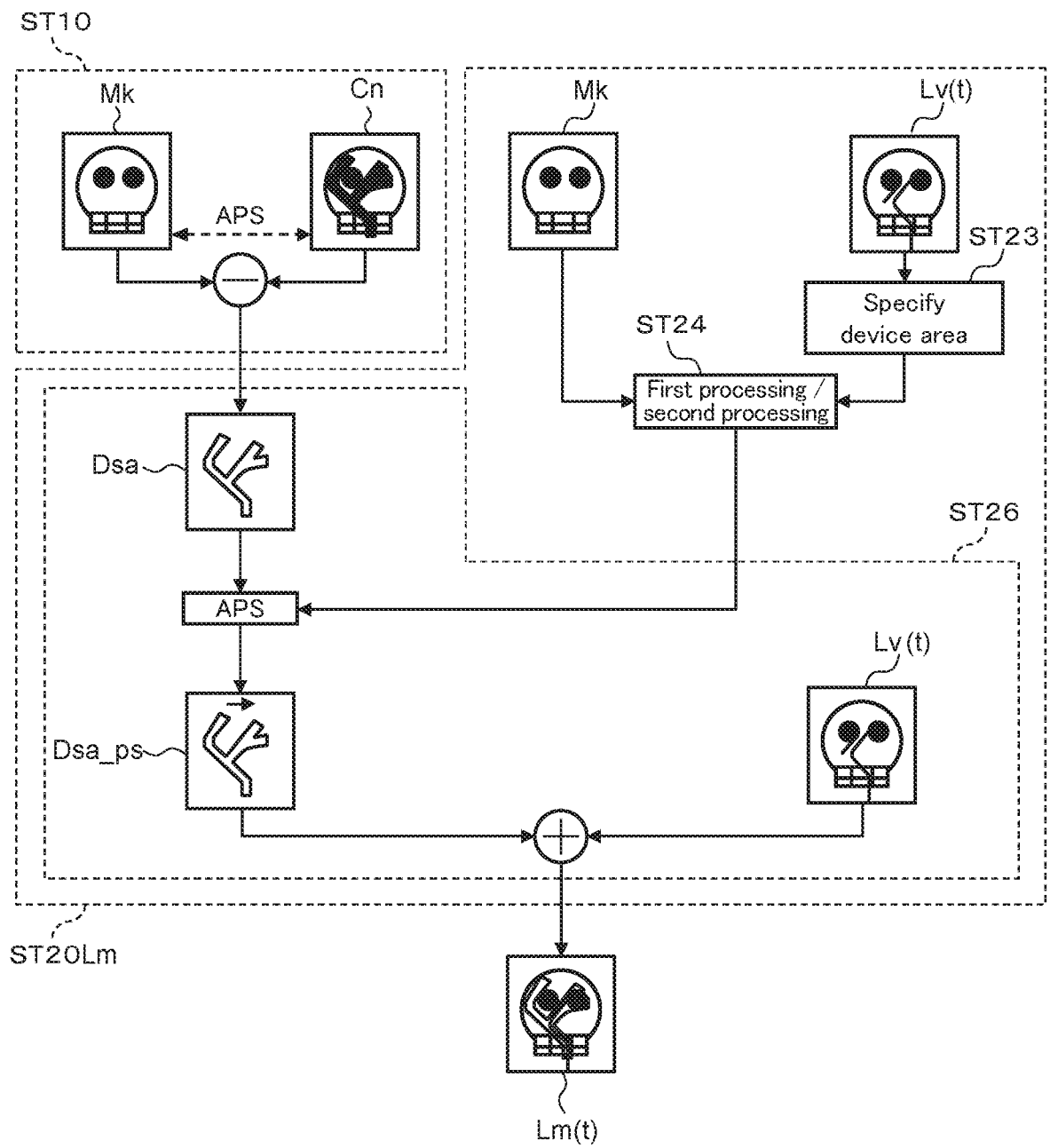
FIG. 11 is a schematic diagram for explaining a process of generating a fluoroscopy landmark image in the modification of the first embodiment.

According to this configuration, as shown in FIGS. 10 and 11, step ST10 is performed to generate the blood vessel image Dsa as previously discussed.

After step ST10, step ST20Lm for generating the fluoroscopy landmark image Lm(t) is performed instead of above-described steps ST20 and ST30. Specifically, in this step ST20Lm, steps ST21 to ST24 are performed as described above, and then step ST26 is performed in substitution for steps ST25 and ST30. In step ST26, the processing circuitry 94 generates the fluoroscopy roadmap image based on the live image Lv(t), by performing the position alignment (APS) and the image operation. More concretely, and for example, the processing circuitry 94 in step ST26 calculates the index value of the amount of misalignment between the live image Lv(t), having been subjected to the first processing or the second processing in step ST24, and the mask image Mk, and performs the position alignment (APS) of shifting the live image Lv(t) and/or the blood vessel image Dsa generated in step ST13 to minimize the calculated index value. The processing circuitry 94 also performs the image operation (addition) between, for example, the blood vessel image Dsa_ps obtained after the shift and the live image Lv(t) to generate the fluoroscopy landmark image Lm(t).

The processing circuitry 94 then causes the display 92 to display this fluoroscopy landmark image Lm(t). A doctor, etc. can therefore advance the device while viewing the fluoroscopy landmark image Lm(t) and the live image Lv(t) displayed in real time, and treat the intended treatment site in the blood vessels. Note that the real-time display here does not indicate the processing of displaying images strictly at each moment of their imaging, but it is indicative of the processing where the medical image processing apparatus 90 sequentially displays live images Lv(t)'s as well as the fluoroscopy landmark images Lm(t)'s generated from the respective live images Lv(t)'s, in parallel with the X-ray diagnostic apparatus 1 sequentially acquiring these live images Lv(t)'s.

Step ST20Lm is complete upon performing such steps ST21 to ST24 and ST26.

After step ST20Lm, step ST40 is performed where the processing circuitry 94 determines whether or not an instruction for ending the imaging operation is input. If it is determined that the instruction for ending the imaging operation is not input, the processing returns to step ST22 and continues with steps ST22 to ST40. If it is determined that the instruction for ending the imaging operation is input, the processing is terminated.

According to the modification of the first embodiment, therefore, a fluoroscopy roadmap image (fluoroscopy landmark image Lm(t)) based on the second X-ray image (live image Lv(t)) can be generated by performing the position alignment of the first scheme and the image operation. Also, since the modification proceeds with steps ST10 and ST21 to ST24 in the same manner as the first embodiment, the modification can realize the same effects and advantages as those of the first embodiment.

Note that, as in the case of the first embodiment, this modification can also adopt the position alignment of the second scheme in place of the position alignment of the first scheme. When such a form is adopted, the term "APS" in step ST26 in FIGS. 10 and 11 is replaced with "altered APS", as in the foregoing description. The position alignment of the second scheme can also provide, aside from the capability of making use of the existing APS technique according to the first scheme, the same advantages as those of the described modification.

Second Embodiment

The second embodiment relates to the instances of updating the mask image Mk to be subjected to the position alignment with the live image Lv(t). The second embodiment is suitable in the events where, for example, a body motion of a subject P, etc., which occurred after generation of the blood vessel image Dsa using the mask image Mk, has made it impossible for the background in the mask image Mk to cancel out the background in the live image Lv(t). The updated mask image Mk_dv here is the same as the live image Lv(t) at the time of the update, and it shows the device. Note that the succeeding live images Lv(t)'s will involve changes from the mask image Mk_dv in accordance with the movement of the device.

The area specifying function 945 of the processing circuitry 94 accordingly specifies the device area, where the device is included, in also the mask image Mk_dv acquired with this device inserted, in addition to specifying the device area in the live image Lv(t) in the manner as discussed.

The position alignment function 946 performs position alignment in cooperation with the image processing function 944, using the above-described first processing or second processing for the two device areas specified by the area specifying function 945.

The remaining aspects are the same as the first embodiment.

Figure 12:
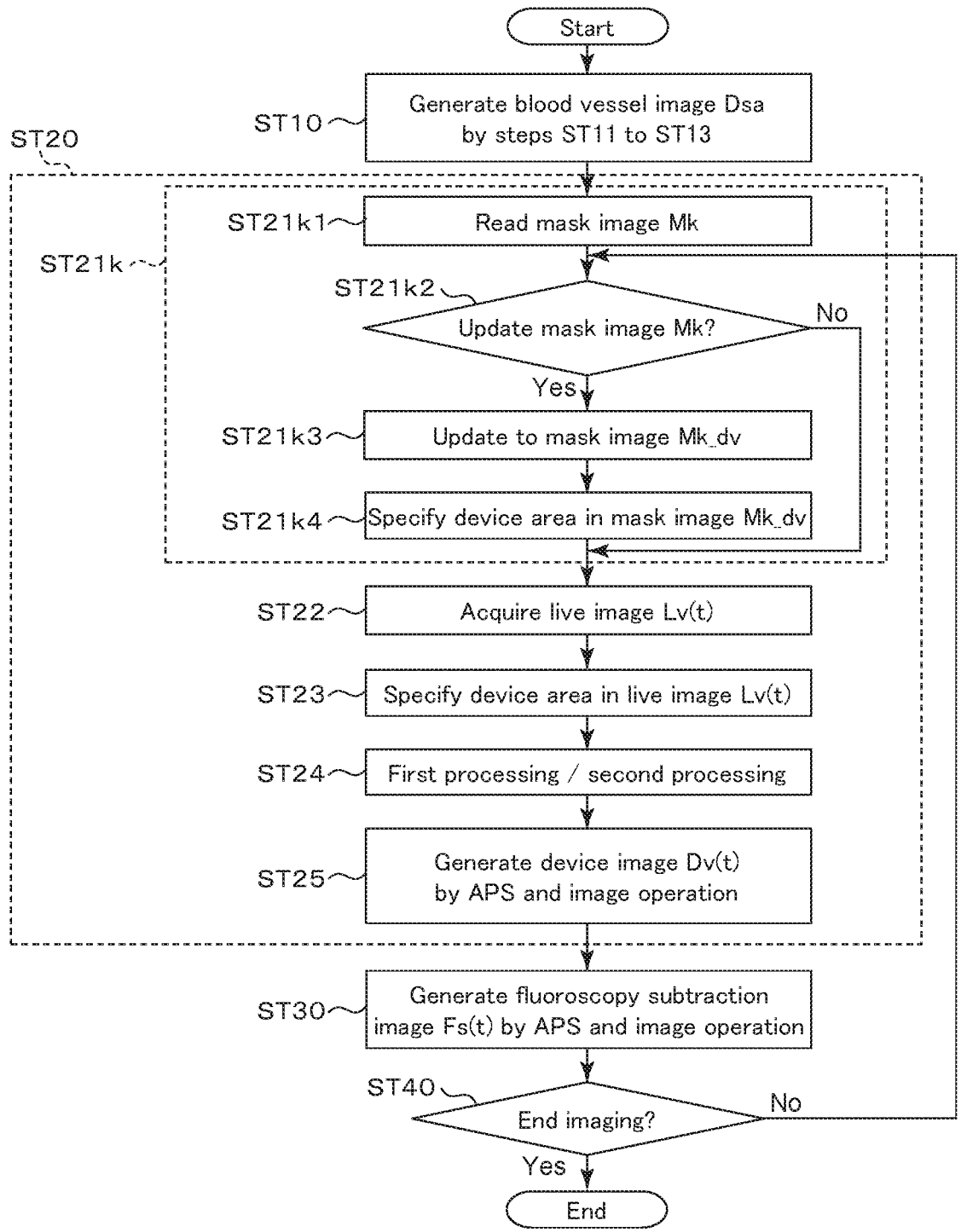
FIG. 12 is a flowchart for explaining operations in a second embodiment.
Figure 13:
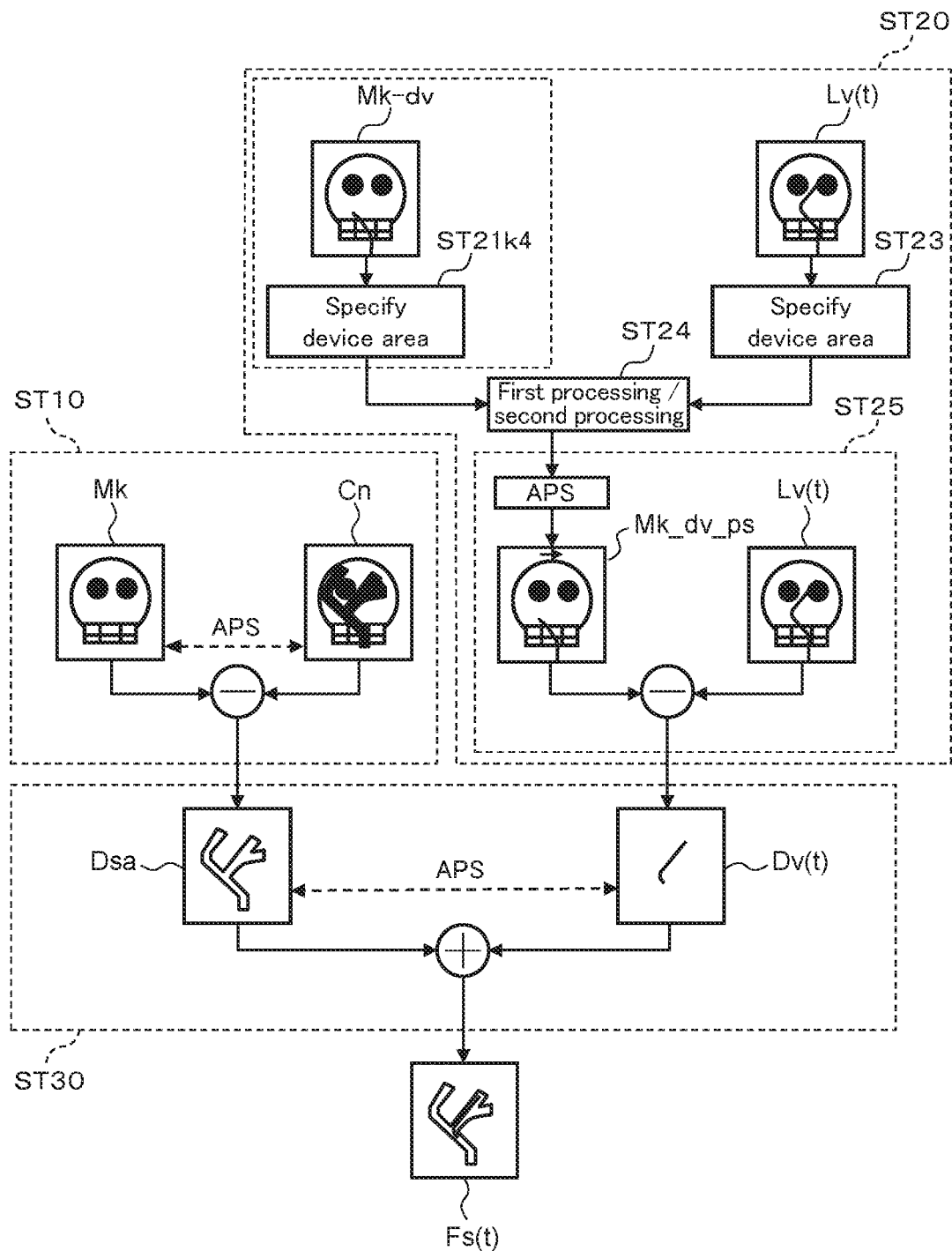
FIG. 13 is a schematic diagram for explaining a process of generating a fluoroscopy subtraction image in the second embodiment.

Next, operations according to the second embodiment will be described with reference to the flowchart in FIG. 12 and the schematic diagram in FIG. 13.

Suppose that step ST10 has now been performed in the manner as discussed, and the blood vessel image Dsa has been produced therefrom.

After step ST10, step ST20 including the process of updating the mask image Mk is performed. In step ST20 of this embodiment, step ST21k different from step ST21 described for the foregoing embodiment, and steps ST22 to ST25 similar to those described for the foregoing embodiment are performed. Step ST21k includes steps ST21k1 to ST21k4.

In step ST21k1, the processing circuitry 94 reads the mask image Mk from the memory 91. After step ST21k1, step ST21k2 is performed where the processing circuitry 94 determines whether or not the mask image Mk should be updated. (Note that, if the update determination is performed again after the mask image Mk has been updated to the mask image Mk_dv, the determination is made based on the updated mask image Mk_dv.) This determination corresponds to whether or not the mask image Mk can erase the background in the live image Lv(t). As such, the determination in step ST21k2 may employ one or more judgments as appropriate, including, for example: (a) judging whether or not the index value based on the difference between the images, used in step ST24 in the last round, is equal to or greater than a threshold; (b) judging whether or not a body motion of the subject P is detected by a sensor (not illustrated); and (c) judging whether or not the device image Dv(t) generated in step ST25 in the last round, or the fluoroscopy subtraction image Fs(t) generated in step ST30 in the last round, shows an artifact. In any case, if it is determined in step ST21*k*2 that the update of the mask image Mk is not necessary, the processing transitions to step ST22. If it is determined that the mask image Mk should be updated, the processing transitions to step ST21*k*3. The description will be given of the case of performing the update.

In step ST21*k*3 after step ST21*k*2, the processing circuitry 94 updates the mask image Mk. Specifically, the processing circuitry 74 of the X-ray diagnostic apparatus 1 controls the imaging unit 10 according to the operator's operation on the input interface 73 so that the mask image Mk_dv is acquired in the state where the device is inserted. This mask image Mk_dv is transmitted from the X-ray diagnostic apparatus 1 to the medical image processing apparatus 90. The processing circuitry 94 of the medical image processing apparatus 90 stores the received mask image Mk_dv in the memory 91. The current mask image Mk is thus updated to the new mask image Mk_dv. In the mask image Mk_dv obtained by this update, the device appears. The same processing may take place also in the next round and onward when the updated mask image Mk_dv is further updated to another, new mask image Mk_dv.

After step ST21*k*3, step ST21*k*4 is performed where the processing circuitry 94 specifies in the mask image Mk_dv the device area where the device is included, in advance of the position alignment between the mask image Mk_dv and the live image Lv(t). Specifying the device area here may adopt various techniques as discussed for step ST23 above. For example, the processing circuitry 94 may specify the device area in the mask image Mk_dv, based on this mask image Mk_dv as the latest image out of the mask image Mk_dv and the live image Lv(t) and using the trained model Md. Note that the expression "latest" may be replaced with "just updated". The device area may be specified using another technique sa discussed for step ST23. In any case, step ST21*k* is complete upon performing steps ST21*k*1 to ST21*k*4 as above.

After step ST21*k*, steps ST22 to ST25 are performed in the manner as discussed. Note, however, that in steps ST24 to ST25 the processing circuitry 94 uses, for the specified two device areas, the above-described first processing or second processing to perform the position alignment (APS). In step ST24, for example, the processing circuitry 94 subjects both the mask image Mk_dv and the live image Lv(t) to the first processing or the second processing. In step ST25, the processing circuitry 94 calculates the index value of the amount of misalignment between the mask image Mk_dv and the live image Lv(t), having been subjected to the first processing or the second processing, and performs the processing (APS) of shifting the live image Lv(t) and/or the mask image Mk_dv to minimize the calculated index value. Then, the processing circuitry 94 performs the image operation (subtraction) between, for example, the mask image Mk_dv_ps obtained after the shift and the live image Lv(t) to generate the device image Dv(t). Upon performing such steps ST21*k* to ST25, step ST20 is complete.

After step ST20, steps ST30 to ST40 are performed in the manner as discussed. In step ST40, the processing circuitry 94 determines whether or not an instruction for ending the imaging operation is input. If it is determined that the instruction for ending the imaging operation is not input, the processing returns to step ST21*k*2 and continues with steps ST21*k*2 to ST40. If it is determined in step ST40 that the instruction for ending the imaging operation is input, the processing is terminated.

According to the second embodiment as described above, the device area where the device is included is specified also in the first X-ray image acquired with the device inserted (mask image Mk_dv). Also, the above-described first processing or second processing is applied to the specified two device areas, whereby performing the position alignment. The second embodiment with this configuration can provide the same advantages as those of the first embodiment, and can further secure such advantages even when the mask image Mk_dv acquired with the device inserted is used for the position alignment with the live image Lv(t). For example, it is possible to suppress the errors in the position alignment between the images, which can occur due to the interference between the device at a given location in the mask image Mk_dv and the device at another location (e.g., location where the device has reached after forward movement from said given location) in the live image Lv(t). Since the second embodiment proceeds with steps ST10 and ST22 to ST24 in the same manner as the first embodiment, the second embodiment can realize the same effects and advantages as those of the first embodiment.

Note that, as in the case of the first embodiment, the second embodiment may also adopt the position alignment of the second scheme in place of the position alignment of the first scheme. When such a form is adopted, the term "APS" in step ST25 in FIGS. 12 and 13 is replaced with "altered APS", as in the foregoing description. The position alignment of the second scheme can also provide, aside from the capability of making use of the existing APS technique according to the first scheme, the same advantages as those of the first embodiment.

(Modification)

A modification of the second embodiment will be described. The second embodiment has been described as generating the fluoroscopy subtraction image Fs(t) as the fluoroscopy roadmap image. The modification of the second embodiment is the case of generating a fluoroscopy landmark image Lm(t) as the fluoroscopy roadmap image, as shown in FIGS. 14 and 15.

Accordingly, the processing circuitry 94 with the image processing function 944 does not generate the above-described device image Dv(t). The processing circuitry 94 instead subjects a blood vessel image Dsa_ps, obtained through the pixel-shift processing of a blood vessel image Dsa, and a live image Lv(t) to the image operation (addition). The fluoroscopy landmark image Lm(t) is thus generated.

The remaining aspects are the same as the second embodiment.

Figure 15:
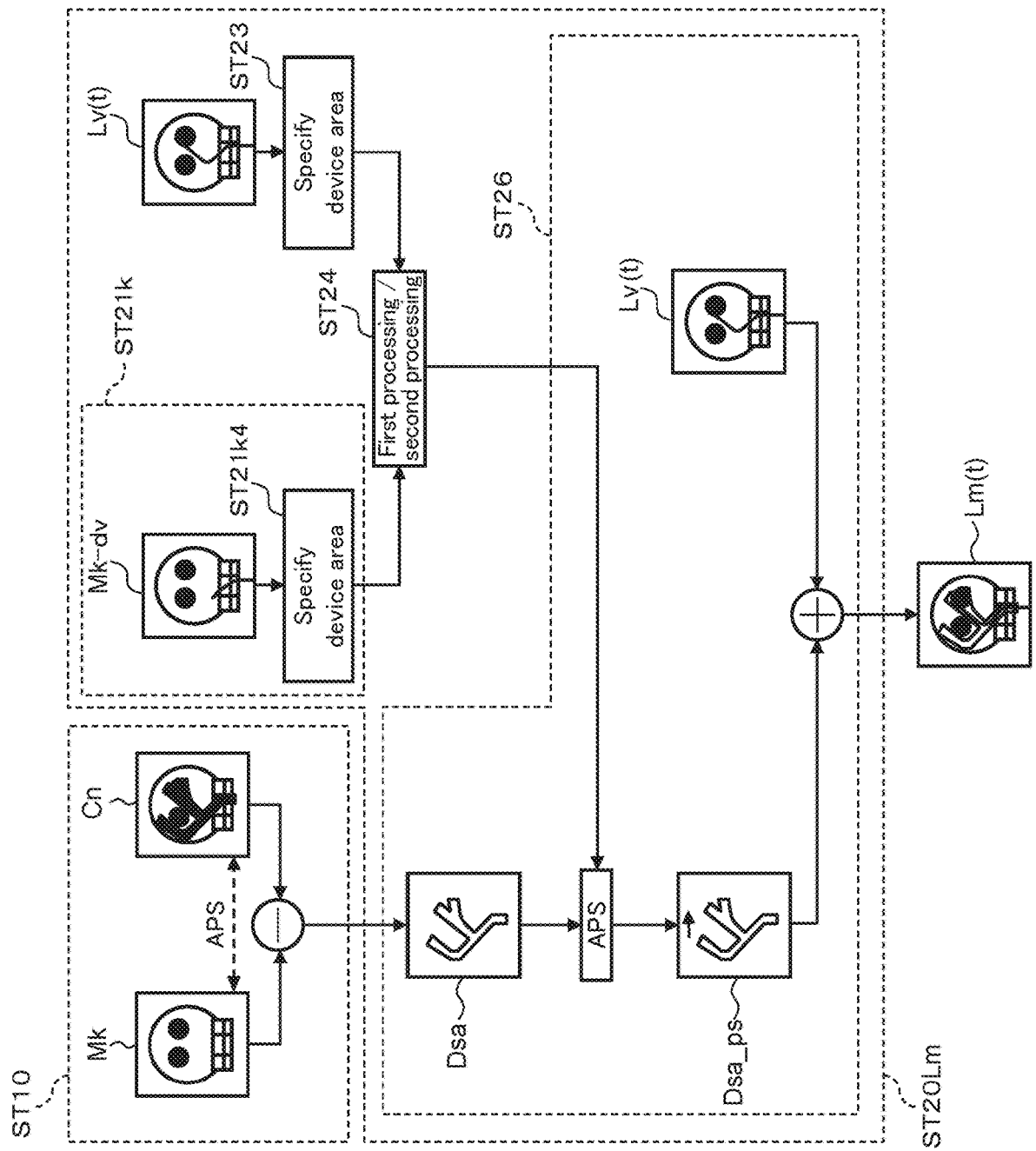
FIG. 15 is a schematic diagram for explaining a process of generating a fluoroscopy landmark image in the modification of the second embodiment.

According to this configuration, as shown in FIGS. 14 and 15, step ST10 is performed to generate the blood vessel image Dsa as previously discussed.

After step ST10, step ST20Lm for generating the fluoroscopy landmark image Lm(t) is performed instead of above-described steps ST20 and ST30. Specifically, in this step ST20Lm, steps ST21*k* to ST24 are performed as described above, and then step ST26 is performed in substitution for steps ST25 and ST30. In step ST26, the processing circuitry 94 generates the fluoroscopy roadmap image based on the live image Lv(t), by performing the position alignment (APS) and the image operation. More concretely, and for example, the processing circuitry 94 in step ST26 calculates the index value of the amount of misalignment between the live image Lv(t), having been subjected to the first processing or the second processing in step ST24, and the mask image, and performs the position alignment (APS) of shifting the live image Lv(t) and/or the blood vessel image Dsa generated in step ST13 to minimize this index value. The processing circuitry 94 also performs the image operation (addition) between, for example, the blood vessel image Dsa_ps obtained after the shift and the live image Lv(t) to generate the fluoroscopy landmark image Lm(t).

The processing circuitry 94 then causes the display 92 to display this fluoroscopy landmark image Lm(t). A doctor, etc. can therefore advance the device while viewing the fluoroscopy landmark image Lm(t) and the live image Lv(t) displayed in real time, and treat the intended treatment site in the blood vessels. Note that, as in the foregoing description, the real-time display here is indicative of the processing where the medical image processing apparatus 90 sequentially displays live images Lv(t)'s as well as the fluoroscopy landmark images Lm(t)'s generated from the respective live images Lv(t)'s.

Step ST20Lm is complete upon performing such steps ST21*k* to ST24 and ST26.

After step ST20Lm, step ST40 is performed in the manner as discussed.

According to the modification of the second embodiment, therefore, a fluoroscopy roadmap image (fluoroscopy landmark image Lm(t)) based on the second X-ray image (live image Lv(t)) can be generated by performing the position alignment of the first scheme and the image operation. Also, since the modification proceeds with steps ST10 and ST21*k* to ST24 in the same manner as the second embodiment, the modification can realize the same effects and advantages as those of the second embodiment.

Note that, as in the above cases, this modification can also adopt the position alignment of the second scheme in place of the position alignment of the first scheme. When such a form is adopted, the term "APS" in step ST26 in FIGS. 14 and 15 is replaced with "altered APS", as in the foregoing description. The position alignment of the second scheme can also provide, aside from the capability of making use of the existing APS technique according to the first scheme, the same advantages as those of the described modification.

The above embodiments and modifications may each adopt a configuration of using, in lieu of the device area, a device area candidate as a candidate of the area where the device image appears. The device area candidate here can be an area that likely includes the device, and it may be the device area itself. Accordingly, the processing circuitry 74 and the processing circuitry 94 with their respective area specifying functions 745 and 945 may each specify, before the position alignment between a first X-ray image and a second X-ray image acquired with the device inserted, the device area candidate in the second X-ray image as a candidate of the area where the device appears. Also, the processing circuitry 74 and the processing circuitry 94 with their respective position alignment functions 746 and 946 may each perform the position alignment including the first processing of removing the specified device area candidate or the second processing of reducing a contribution of the device area candidate. In the course of such processing, the processing circuitry 74 and the processing circuitry 94 with their respective area specifying functions 745 and 945 may each detect the device area showing the device from the second X-ray image, and set the detected device area as the device area candidate. Similarly, the program to be executed by a computer's processor may include a first program code which causes the processor to specify, before position alignment between a first X-ray image and a second X-ray image acquired with a device inserted, the device area candidate in the second X-ray image as a candidate of the area where the device appears, and a second program code which causes the processor to perform the position alignment using the first processing of removing the specified device area candidate or the second processing of reducing a contribution of the device area candidate. Each of the embodiments and modifications below also utilizes such a device area candidate as will be discussed.

Third Embodiment

The third embodiment relates to the instances of specifying the device area candidate based on information about a motion between frames of live image Lv(t) as the second X-ray image. The third embodiment is suitable in the events where the device area candidate is updated in accordance with the advancement of a device.

Figure 16:
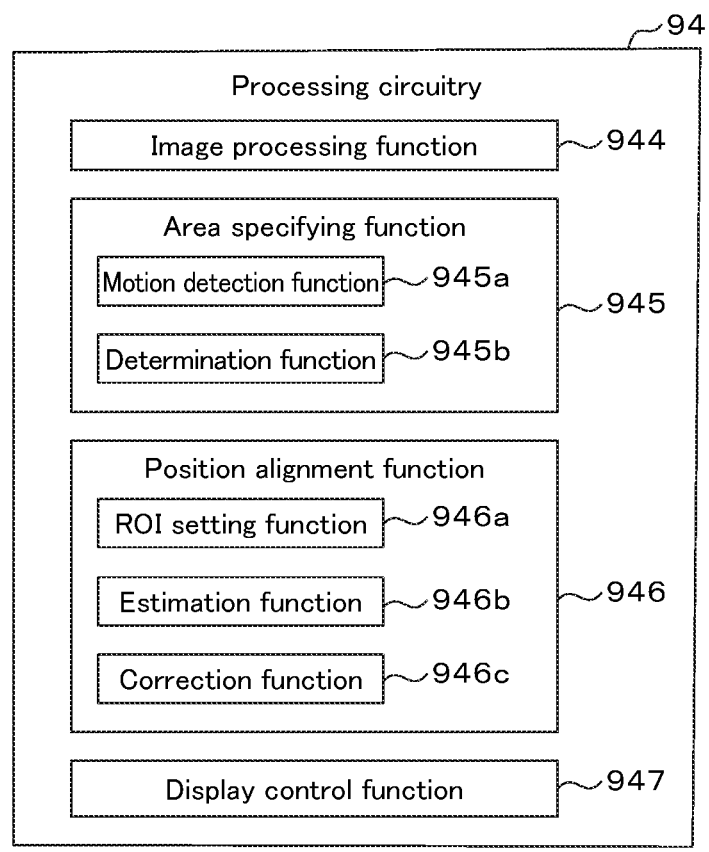
FIG. 16 is a block diagram showing a configuration of processing circuitry of a medical image processing apparatus according to a third embodiment.

The area specifying function 945 of the processing circuitry 94, accordingly, includes a motion detection function 945*a* and a determination function 945*b* as shown in FIG. 16.

The processing circuitry 94 with the motion detection function 945*a* detects information about an inter-frame motion in the second X-ray image. It is not a requisite for the motion detection function 945*a* here to perform motion detection/judgment for each frame of the second X-ray image. The motion detection/judgment may be performed at fixed timings or variable timings. For the timings of motion detection/judgment, a table showing association with imaging/fluoroscopy conditions may be provided. For example, the table may associate the imaging/fluoroscopy conditions of 15 [fps] with the timing of every n frames. In this case, the motion detection function 945*a* can refer to this table so that the motion detection/judgment at timings according to the imaging/fluoroscopy conditions is enabled. The motion detection function 945*a* may perform this motion detection/judgment as post-processing after completion of the data acquisition for all frames. In other words, the motion detection function 945*a* may be exerted when it has not been applied in real time, or when a new device area candidate is specified and computation is required again after completing the data acquisition for all frames.

The motion detection function 945*a* may employ any motion-image analyzing technique for motion detection, and examples of such techniques include template matching, block matching, difference analysis, optical-flow technique, background estimation, and so on.

The motion information may be an amount of movement, or it may be a combination of the movement amount and a multi-dimensional vector defined with directions x, y, θ, etc. Note that the motion information may be subject to discard when, for example, the detected movement amount is equal to or lower than a lower limit value or equal to or greater than an upper limit value, in order to avoid error determinations.

The motion detection function 945*a* may store the motion information (movement amount, vector, etc.) detected based on the current frame (input image) in the memory 91. The motion information may be accumulated in the memory 91, etc., so that the accumulated information is used by the determination function 945*b* for the subsequent frame and onward.

The processing circuitry 94 with the determination function 945*b* specifies (determines) a device area candidate based on the motion information. The determination function 945*b* may specify (determine) the device area candidate based on, for example, spatial distribution of the inter-frame motion in the second X-ray image. In this example, also, the determination function 945*b* may specify (determine) the device area candidate based on, among such spatial distribution of the motion, information about the motion that is locally distributed in concordance with the device.

Note that conditions for determining the device area candidate here may be varied according to an FOV, imaging conditions, etc. The abbreviation "FOV" stands for field of view. The conditions for determining the device area candidate may adopt, for example, one or more of the following conditions (i) to (iii) as appropriate. The term "determination subject area" appearing in the below explanation will mean a partial area (local area) in the second X-ray image.

(i) Movement Amount

Condition that the movement amount of a determination subject area exceeds the average movement amount of the entire image. With the movement of the device, the image involves a local kinetic change. If the entire image is moved, a body motion or a couch movement is occurring.

(ii) Vector Analysis

Condition that there is distribution of an alien component differing from the vector of the entire image, determined based on the distribution of vectors including movement amounts and directions. The vector of the entire image here contains a vector component from a body motion of a subject, if any, as the device is present in the subject body. The device is likely present in the area where the component differing from the vector of the entire image is distributed. Accordingly, the vector analysis may employ principal component analysis, multi-variable analysis, statistical analysis or other statistical techniques, etc. as appropriate.

Also, information about past motions (vector distribution tendency, etc.) may be accumulated for use in determination (to differentiate from body motions). For example, information about a body motion (which is mainly of a single vector) when corresponding to breathing or heartbeats shows a periodic tendency. Meanwhile, information about the movement of a device (multi-vectorial) does not show a periodic tendency, as the device moves in various directions.

As a further option, for example, periodicity may be analyzed based on vital signals (from breathing, heartbeats, etc.), and based on this periodicity, motion information and a device area candidate once acquired for the past frame of the same phase may be read from the memory 91 for use in the determination.

(iii) Pixel Values

Condition that the average pixel value of a determination subject area is equal to or below a threshold.

Condition that the contrast between a determination subject area and its surrounding area is equal to or greater than a threshold.

Condition that the dispersion of pixel values in a determination subject area is equal to or greater than a threshold. (If an area has dispersion below the threshold, the area is homogeneous and likely corresponds to a background portion.)

In addition to the above, the number of pixels may be limited for the device area candidate specified (determined) using any of the above conditions (i) to (iii). This is because, as the proportion of the device area candidate in the second X-ray image increases, the number of pixels available for the position alignment becomes relatively small, which could deteriorate the accuracy of the position alignment.

The position alignment function 946 of the processing circuitry 94 includes an ROI setting function 946a, an estimation function 946b, and a correction function 946c.

The processing circuitry 94 with the ROI setting function 946a removes the specified device area candidate so as to set a region of interest (ROI) for the position alignment, or lowers the weight of the device area candidate, namely, reduces the contribution of the device area candidate, for calculating the index value of the amount of misalignment within a region of interest. The region of interest here may be either a part or the entire portion of the second X-ray image. Also, the weight may be assigned according to the ratio of components of the movement amount (x, y, θ) from the motion detection.

Similar to the above, as the proportion of the device area candidate in the region of interest increases, the number of pixels available for the position alignment becomes relatively small. Since this could deteriorate the accuracy of the position alignment, a limitation may be set for the number of pixels of the device area candidate in the region of interest.

The processing circuitry 94 with the estimation function 946b calculates (estimates) the index value of the amount of misalignment between the first X-ray image and the second X-ray image within the region of interest.

The processing circuitry 94 with the correction function 946c shifts (corrects) the first X-ray image and/or the second X-ray image based on the calculated index value.

Figure 17:
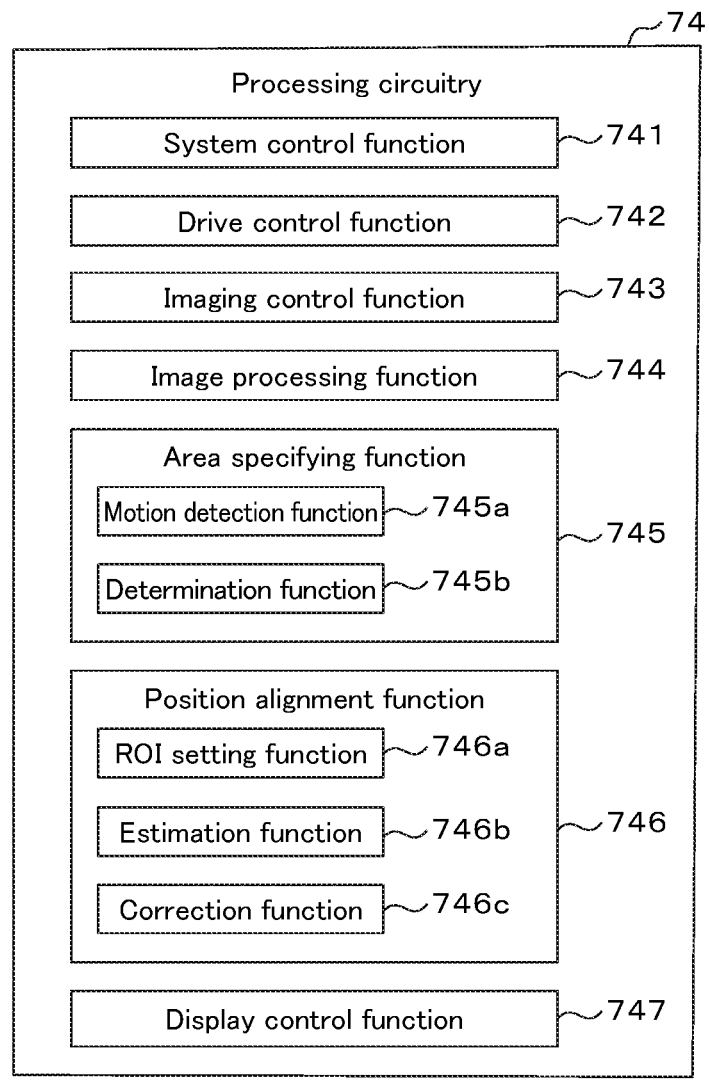
FIG. 17 is a block diagram showing a configuration of processing circuitry of an X-ray diagnostic apparatus according to the third embodiment.

Note that, as in the cases of the foregoing embodiments, etc., the motion detection function 945a, the determination function 945b, the ROI setting function 946a, the estimation function 946b, and the correction function 946c as the functions of the processing circuitry 94 in the medical image processing apparatus 90 are functions equivalent to a motion detection function 745a, a determination function 745b, an ROI setting function 746a, an estimation function 746b, and a correction function 746c as the functions of the processing circuitry 74 in the X-ray diagnostic apparatus 1 as shown in FIG. 17. In other words, the medical image processing system as a whole may make use of the operations of any of the functions in the medical image processing apparatus 90 or the functions in the X-ray diagnostic apparatus 1. In the manner similar to the foregoing description, the description about the operations will assume, as an example, the case with the processing circuitry 94 of the medical image processing apparatus 90.

The remaining aspects are the same as the first or the second embodiment.

Figure 18:
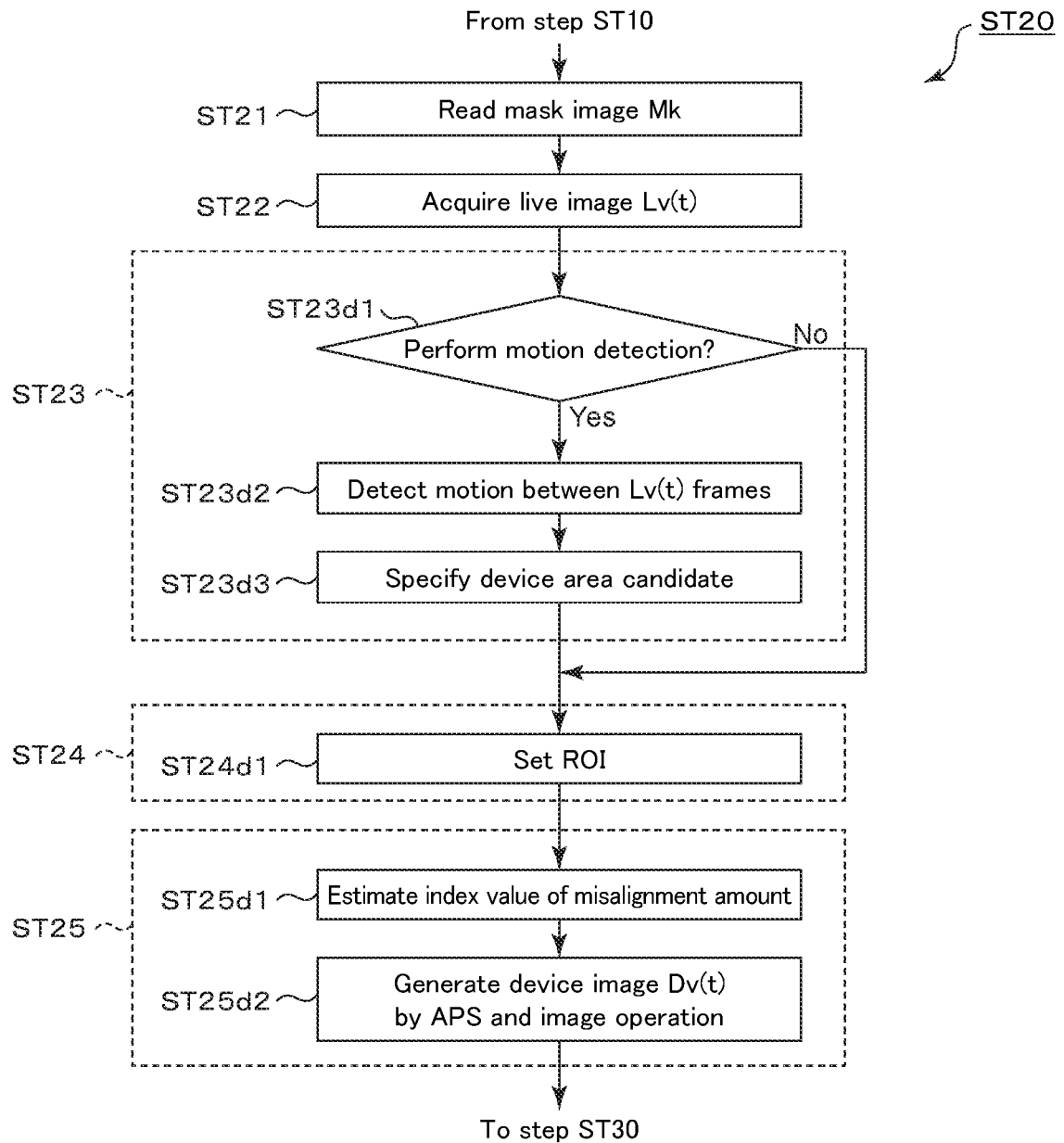
FIG. 18 is a flowchart for explaining operations in the third embodiment.
Figure 19:
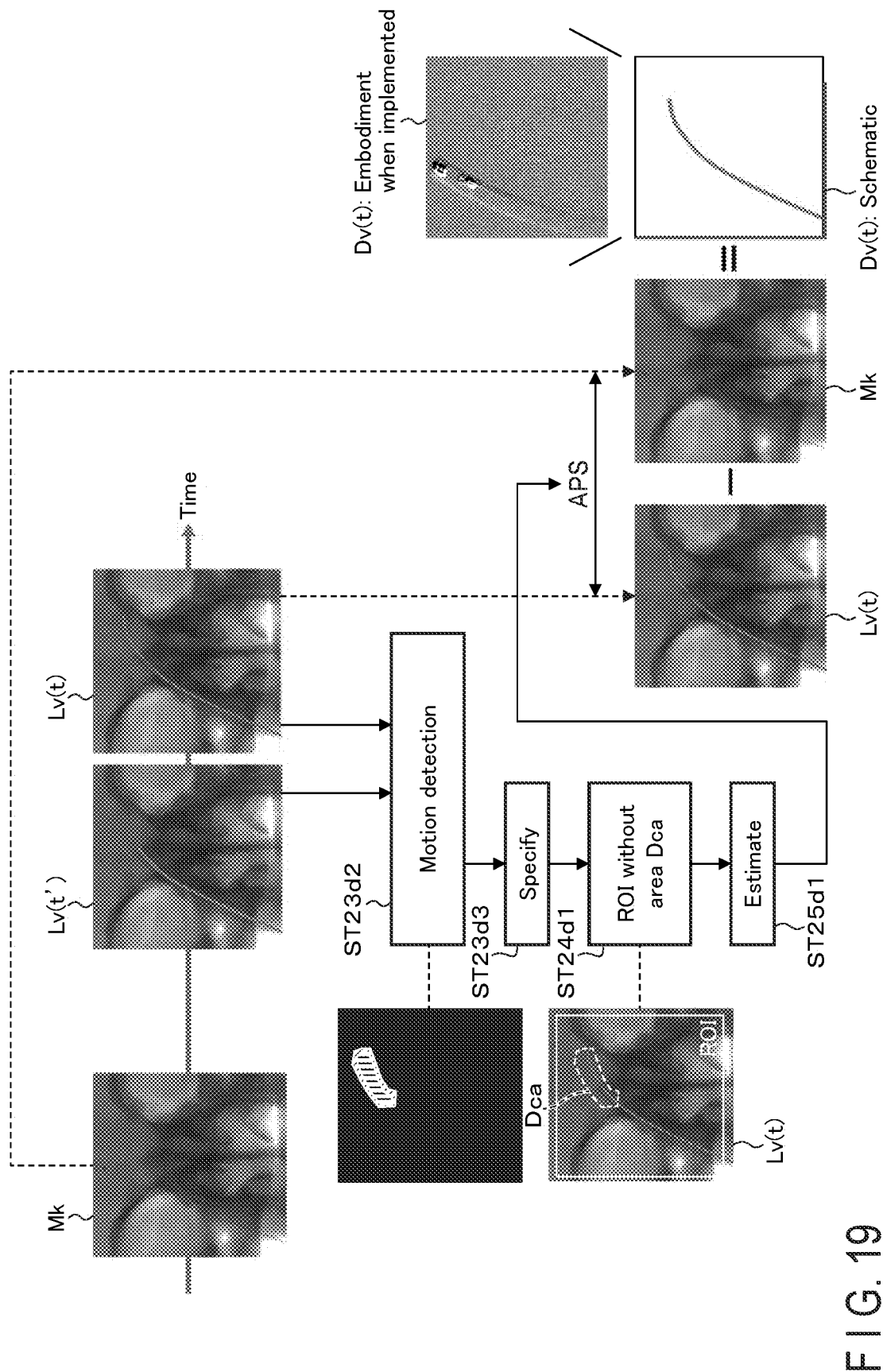
FIG. 19 is a schematic diagram for explaining an effect of the third embodiment.
Figure 20:
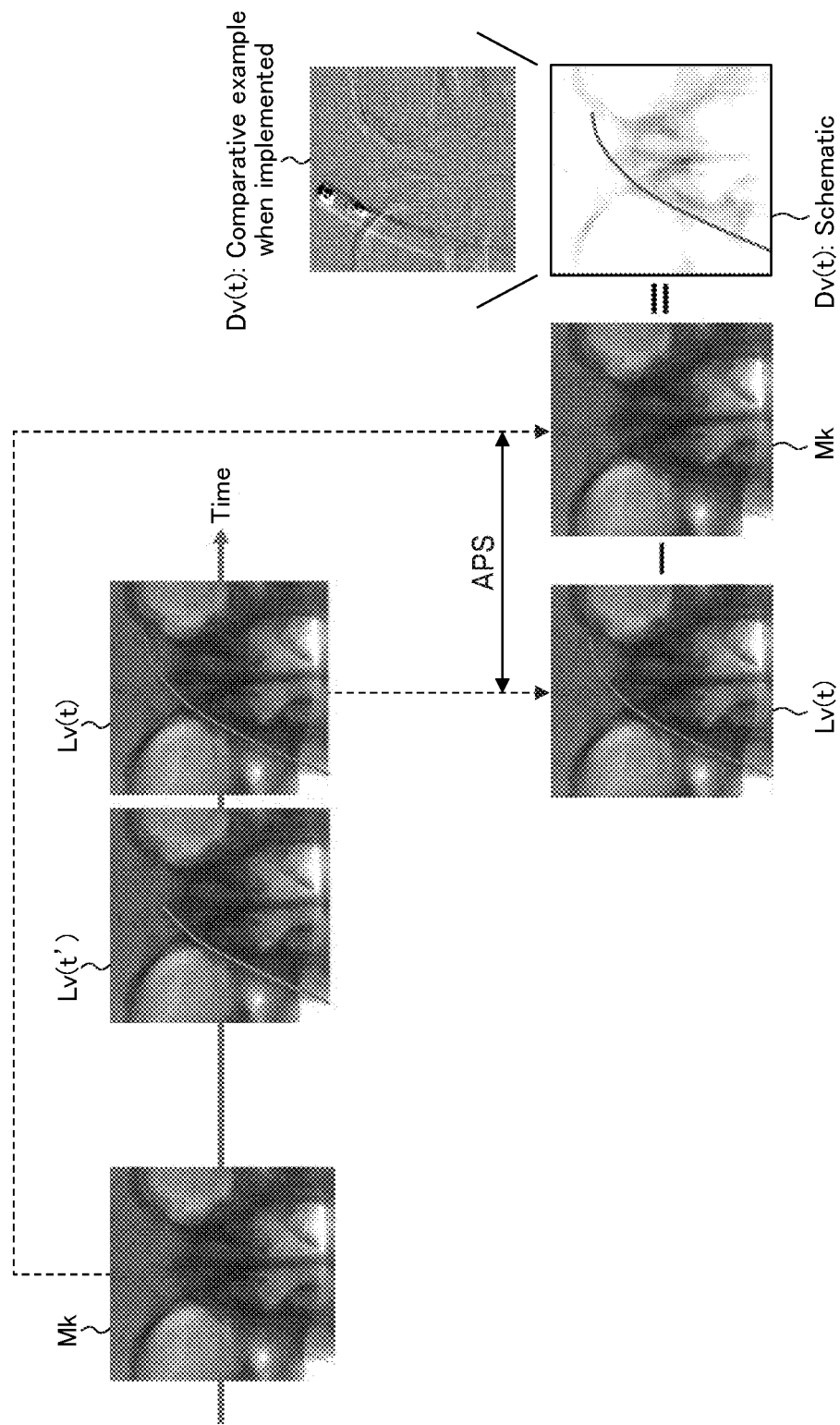
FIG. 20 is a schematic diagram for explaining an effect of a comparative example to the third embodiment.

The operations according to the third embodiment will be described with reference to the flowchart in FIG. 18 and the schematic diagrams in FIGS. 19 and 20.

Suppose that steps ST10, ST21, and ST22 have now been performed in the manner as discussed, and the mask image Mk has been read and the live image Lv(t) has been acquired.

After step ST22, step ST23 with the motion detection is performed. In this step ST23, steps ST23d1 to ST23d3 are performed as one concrete processing example.

In step ST23d1, the processing circuitry 94 determines whether or not to perform the motion detection, and if it is determined that the motion detection is not to be performed, the processing transitions to step ST24. If it is determined that the motion detection is to be performed, the processing transitions to step ST23d2. This determination is enabled by, for example, setting a flag indicative of whether or not to perform the motion detection in the memory 91 in accordance with an operator's operation via the input interface 93, and configuring the processing circuitry 94 to refer to this flag.

In step ST23d2 after step ST23d1, the processing circuitry 94 performs the motion detection between frames of the live image Lv(t) to obtain information about the motion.

After step ST23d2, step ST23d3 is performed where the processing circuitry 94 specifies the device area candidate based on this motion information. For example, the processing circuitry 94 may specify the device area candidate based on spatial distribution of the motion between the frames of the live image Lv(t). For example, further, the processing circuitry 94 may specify the device area candidate based on, among the spatial distribution of the motion, information about the motion that is locally distributed in concordance with the device. Upon performing such steps ST23d1 to ST23d3, step ST23 with the motion detection is complete.

After step ST23, step ST24d1 is performed as one concrete example of step ST24. In step ST24d1, the processing circuitry 94 removes the specified device area candidate to set a region of interest (ROI) for the position alignment. In another implementation, the processing circuitry 94 may lower the weight of the device area candidate for calculating the index value of the amount of misalignment within a region of interest. Upon performing such step ST24d1, step ST24 is complete.

After step ST24, steps ST25d1 and ST25d2 are performed as one concrete example of step ST25.

In step ST25d1, the processing circuitry 94 estimates the index value of the amount of misalignment between the mask image Mk and the live image Lv(t) within the region of interest.

In step ST25d2 after step ST25d1, the processing circuitry 94 performs the processing (APS) of shifting the mask image Mk and/or the live image Lv(t) based on the estimated index value so that the index value is minimized. Then, the processing circuitry 94 performs the image operation (subtraction) between, for example, the shifted mask image Mk and the live image Lv(t) to generate the device image Dv(t). Upon performing such steps ST25d1 and ST25d2, step ST25 is complete.

After step ST25, steps ST30 to ST40 are performed in the manner as discussed.

According to the third embodiment as described, a device area candidate is specified based on the information about a motion between frames of the second X-ray image. With this configuration, the device area candidate is specified as a device area candidate Dca as shown in FIG. 19 that encloses the portion having experienced the movement of the device, not as a device area candidate enclosing the whole of the device. Thus, only the device area candidate Dca, that is, a smaller area, can be subjected to the removal or contribution-reduction processing in advance of the position alignment. Accordingly, the third embodiment can improve the accuracy of the position alignment in addition to realizing the same advantages as those of the first or the second embodiment. Note that the advantages of the first or the second embodiment include, for example, the following (3a) to (3c). (3a) Errors in APS can be suppressed since the displacement of a mask image Mk which would occur following the position of a moving device can be prevented. (3b) Degradation of image quality or viewability attributable to the misalignment (misregistration) in the APS prior to computation of a subtraction image can be prevented, and therefore, treatment procedures can be safely conducted. Here, a device image Dv(t) computed under the misaligned state is given in FIG. 20 as a comparative example. This device image Dv(t) as a comparative example has poor viewability as compared to the device image Dv(t) given in FIG. 19. (3C) Stresses that could hamper smooth treatment procedures can be mitigated, since the viewability does not degrade.

According to the third embodiment, moreover, a device area candidate may be specified based on the spatial distribution of a motion between frames of the second X-ray image. For example, information from a body motion or a couch movement that is spatially distributed over a wide range can be differentiated from information from a device movement that is spatially distributed within a narrow range. As such, the device area candidate can be specified based on the information about a narrowly-distributed motion.

Yet further, according to the third embodiment, a device area candidate may be specified based on, among such spatial distribution of a motion, information about the motion that is locally distributed in concordance with the device. For example, the device area candidate can be specified based on information from the motion distributed within a local area corresponding to the device. The local area corresponding to the device may be used as, for example, a preset device area candidate. This will be described in detail as the following modification example.

(Modification)

A modification of the third embodiment will be described. The third embodiment has been described, assuming the instances of specifying a device area candidate based on information about a motion between frames of the second X-ray image. According to this modification of the third embodiment, a device area candidate is specified based on motion information and a preset device area candidate.

Specifically, the processing circuitry 94 with the determination function 945b specifies, where there is a preset device area candidate, a device area candidate by comparing information about the motion detected by the motion detection function 945a with the preset device area candidate. If the result of this comparison indicates that their respective positions are largely apart from each other, the determination function 945b may exclude the motion information from specifying a device area candidate, or may lower the weight of the pixel values corresponding to the motion information in the subsequent ROI setting processing.

As a method for presetting a device area candidate, for example, a method of referring to, for example, extending or curvilinear shadows, image levels, etc. for area setting may be elected in advance.

Also, for a fluoroscopy roadmap image, which utilizes a previously-generated blood vessel image Dsa, it is possible to adopt the blood vessel region in this blood vessel image Dsa as a device area candidate.

A desired device area candidate may be set by a user, etc. in advance, as well.

In any case, the set device area candidate may have a size larger than the width of a blood vessel, and may include corresponding margins. For example, the device area candidate set based on a blood vessel preferably has a width that covers deformation of the blood vessel caused by the device.

Also, for adopting a blood vessel region as a device area candidate while assuming a locally-located device, it is possible to set a threshold for determining whether or not the device is present within the device area candidate, based on how much of the blood vessel region the device is accounting for.

When processing according to the fluoroscopy roadmap technique is conducted using the same mask image Mk or the same geometric positions (i.e., geometric information including couch coordinates, an imaging angle, etc.), the device area candidates collected in the past may be referred to.

On condition that the device is present only in the blood vessel region, only the device area candidate that is obtained based on a selected blood vessel image Dsa may be specified as an object to be reflected on the region of interest.

Figure 21:
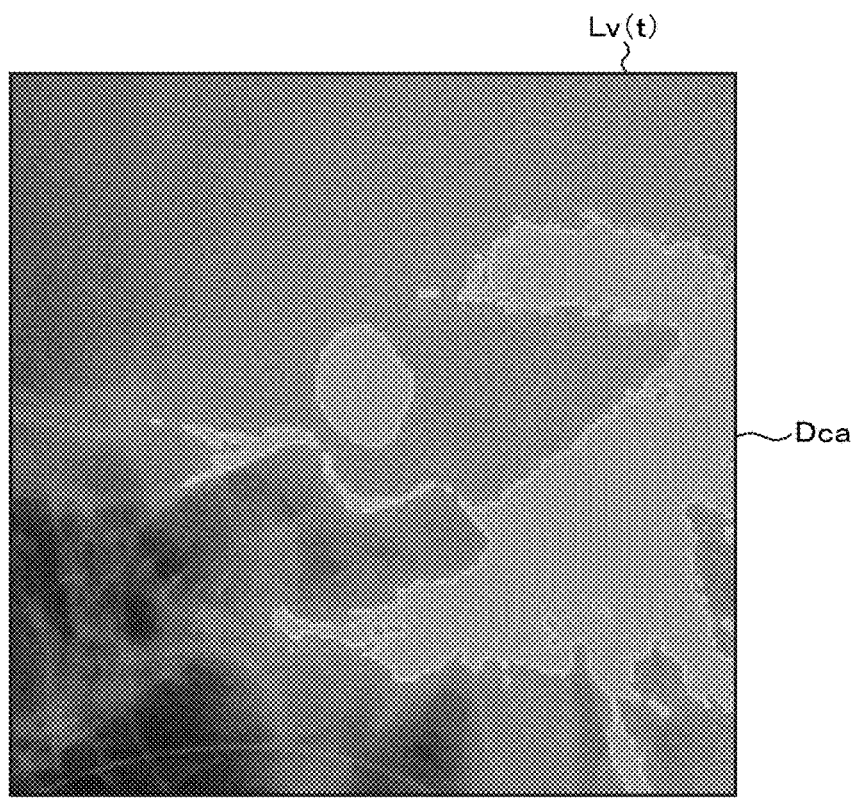
FIG. 21 is a schematic diagram for explaining exemplary setting of a device area candidate in a modification of the third embodiment.
Figure 22:
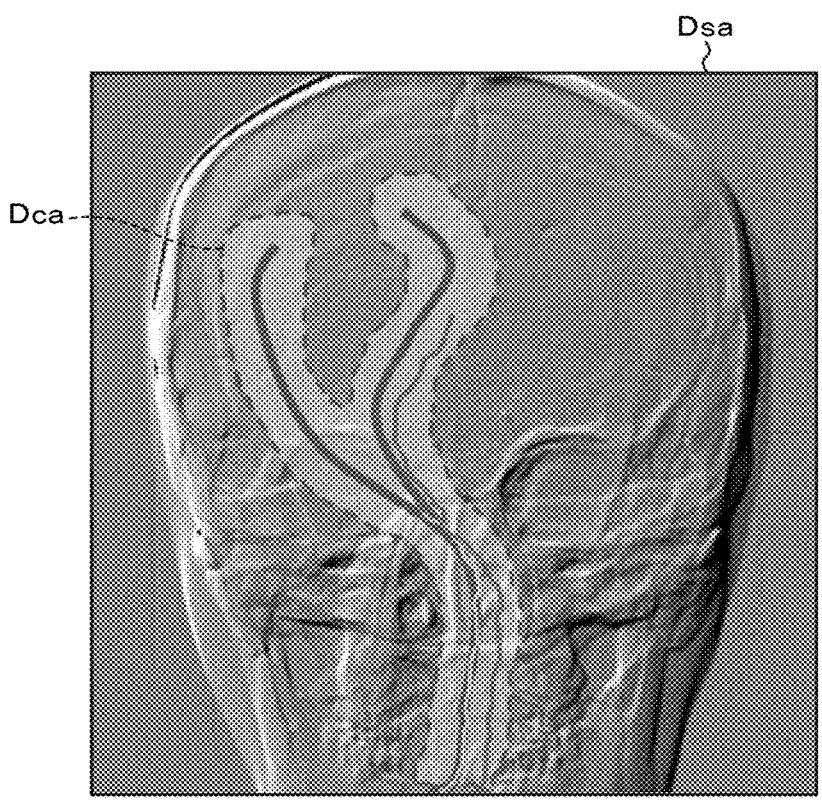
FIG. 22 is a schematic diagram for explaining another exemplary setting of the device area candidate in the modification of the third embodiment.

Accordingly, the image processing function 944 of the processing circuitry 94 manually or automatically sets a device area candidate on an X-ray image beforehand, and stores the X-ray image having been set with this device area candidate in the memory 91. For example, the image processing function 944 may set an area including a portion showing a local movement as the device area candidate. As another example, the image processing function 944 may set, as shown in FIG. 21, an area having a value equal to or below the threshold in a live image Lv(t), as the device area candidate Dca. As yet another example, the image processing function 944 may set, as shown in FIG. 22, an extending or curvilinear area that is superimposed on the blood vessel in a blood vessel image Dsa and wider than this blood vessel, as the device area candidate Dca.

The remaining aspects are the same as the third embodiment.

Figure 23:
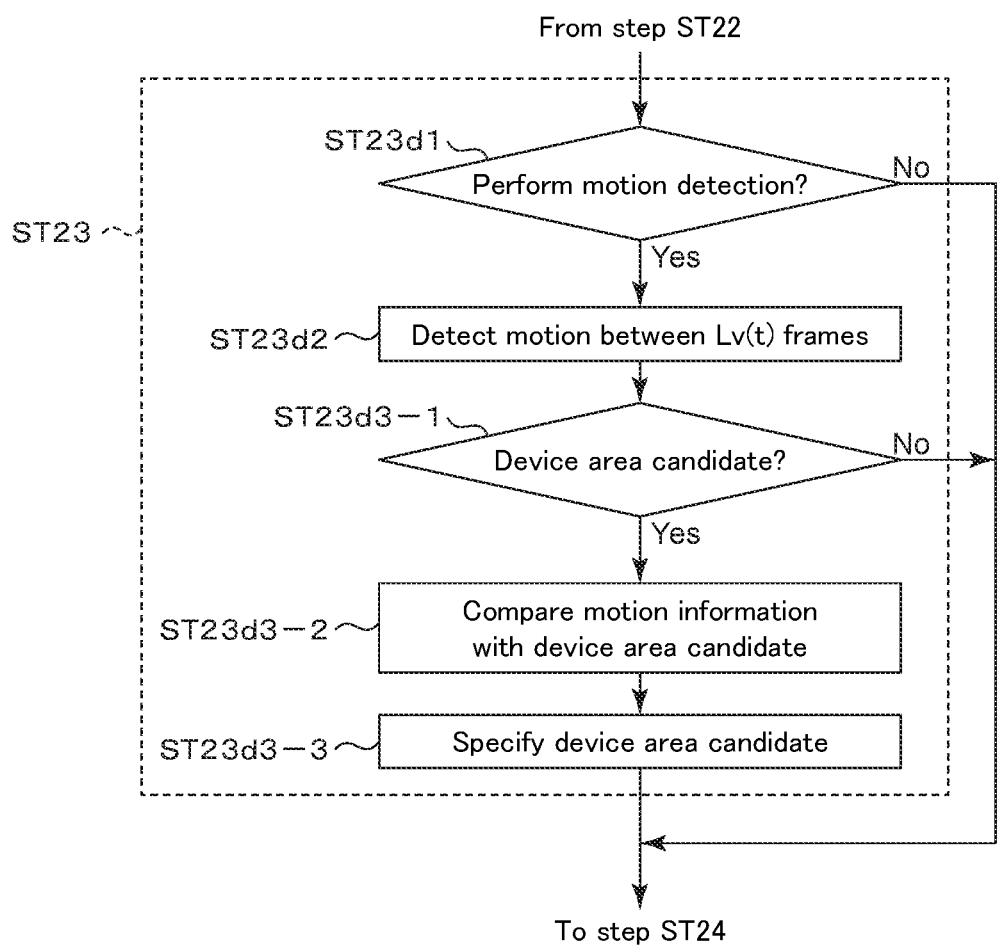
FIG. 23 is a flowchart for explaining operations in the modification of the third embodiment.

According to this configuration, as shown in FIG. 23, steps ST10 to ST23d2 are performed in the manner as discussed above, whereby information about a motion between frames of the live image Lv(t) is acquired.

After step ST23d2, step ST23d3-1 is performed where the processing circuitry 94 refers to a preset device area candidate and determines whether or not the live image Lv(t) includes this device area candidate. If it is determined that the device area candidate is not included, the processing transitions to step ST24. If it is determined that the live image Lv(t) includes the device area candidate, the processing transitions to step ST23d3-2.

In Step ST23d3-2, the processing circuitry 94 compares the detected motion information and the preset device area candidate.

After step ST23d3-2, step ST23d3-3 is performed where the processing circuitry 94 specifies this preset device area candidate as a device area candidate for the position alignment, if the detected motion information is indicative of an inter-frame local movement and also the position indicated by the motion information overlaps the preset device area candidate. Step ST23 employing the motion detection and the preset device area candidate is thus complete.

After step ST23, processing continues with steps ST24 and onward in the manner as discussed.

As described above, according to the modification of the third embodiment, a device area candidate is specified based on, among spatial distribution of a motion between frames of the second X-ray image, information about the motion that is locally distributed in concordance with the device. More specifically, and for example, the device area candidate is specified based on motion information and a preset device area candidate. Therefore, as the preset device area candidate is utilized, the modification allows for specifying a device area candidate while ignoring local movements other than the movement caused by the device.

According to the modification of the third embodiment, further, an area including a portion showing a local movement may be used as a preset device area candidate. With this configuration, the modification allows for specifying a device area candidate with more accuracy.

Fourth Embodiment

The fourth embodiment relates to the instances where the processing of specifying a device area candidate is replaced with image processing, for removing or reducing the influence of a device at the position alignment. The fourth embodiment is preferred in the respect that it does not require the processing of specifying a device area candidate.

The processing circuitry 94, accordingly, omits the area specifying function 945 as shown in FIG. 24. The image processing function 944 includes a conversion function 944a.

The processing circuitry 94 with the conversion function 944a performs, before the position alignment between the first X-ray image and the second X-ray image acquired with a device inserted, image processing on the first X-ray image and the second X-ray image so that a curvilinear or extending image component is erased or attenuated. The curvilinear image component here embraces an image corresponding to the device. The image processing of erasing or attenuating a curvilinear image component may adopt, for example, morphology conversion. As the morphology conversion, for example, a processing technique called erosion may be used, which applies a maximum value filter to an image to reduce the area having a pixel value smaller than the maximum value. Note that the morphology conversion here is not limited to it. Also, the morphology conversion may use other image processing after the erosion. The conversion function 944a may control the image processing according to a field of view of the second X-ray image. For example, the conversion function 944a may change the filter size in the morphology conversion according to the field of view of the second X-ray image. Alternatively or additionally, the changed of the filter size by the conversion function 944a may be based on conditions for the imaging (e.g., SID, FOV, pixel size, etc.). The abbreviation "SID" stands for source image distance. The pixel size is a size of one pixel in X-ray images. As a further exemplary configuration, the conversion function 944a may increase the filter size value in response to the device in an X-ray image having been magnified according to the conditions for imaging. The conversion function 944a is one example of an image processor.

The processing circuitry 94 with the position alignment function 946 performs the position alignment based on the first X-ray image and the second X-ray image which have undergone the image processing. For example, the position alignment function 946 uses the index value of the amount of misalignment between the first X-ray image and the second X-ray image, obtained after the image processing, to perform the position alignment between the first X-ray image and the second X-ray image before the image processing.

Figure 25:
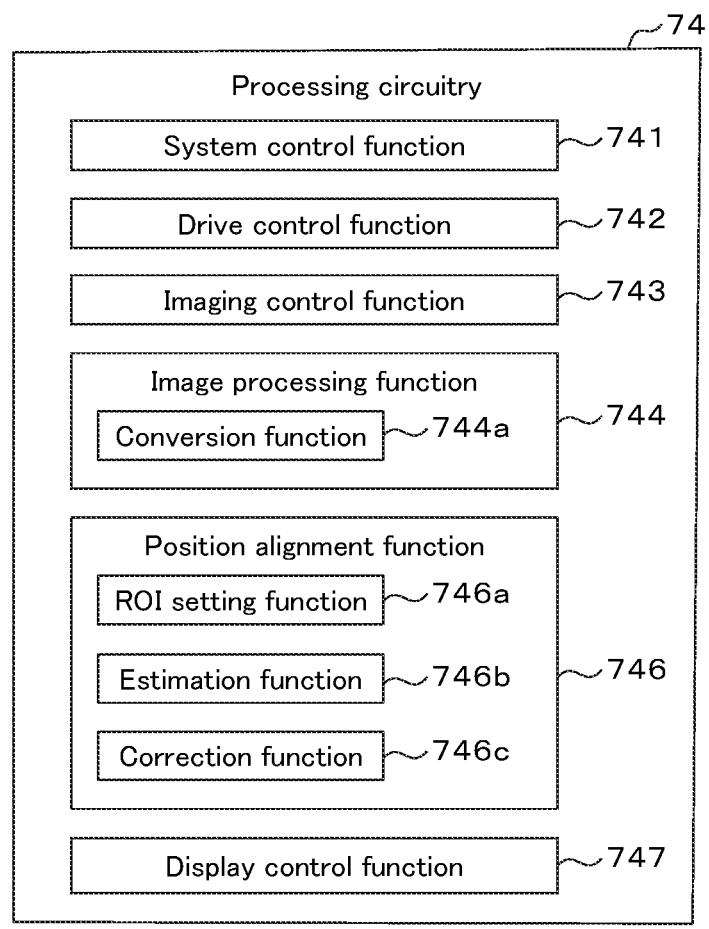
FIG. 25 is a block diagram showing a configuration of processing circuitry of an X-ray diagnostic apparatus according to the fourth embodiment.

As in the cases of the foregoing embodiments, etc., the conversion function 944a, the ROI setting function 946a, the estimation function 946b, and the correction function 946c as the functions of the processing circuitry 94 in the medical image processing apparatus 90 are functions equivalent to a conversion function 744a, the ROI setting function 746a, the estimation function 746b, and the correction function 746c as the functions of the processing circuitry 74 in the X-ray diagnostic apparatus 1 as shown in FIG. 25. In other words, the medical image processing system as a whole may make use of the operations of any of the functions in the medical image processing apparatus 90 or the functions in the X-ray diagnostic apparatus 1. Also, in the manner similar to the foregoing description, the description about the operations will assume, as an example, the case with the processing circuitry 94 of the medical image processing apparatus 90. Furthermore, the program to be executed by a computer's processor may similarly include a first program code which causes the processor to perform, before position alignment between a first X-ray image and a second X-ray image acquired with a device inserted, image processing on the first X-ray image and the second X-ray image so that a curvilinear image component is erased or attenuated, and a second program code which causes the processor to perform the position alignment based on the first X-ray image and the second x-ray image which have undergone the image processing.

The remaining aspects are the same as the third embodiment.

Figure 28:
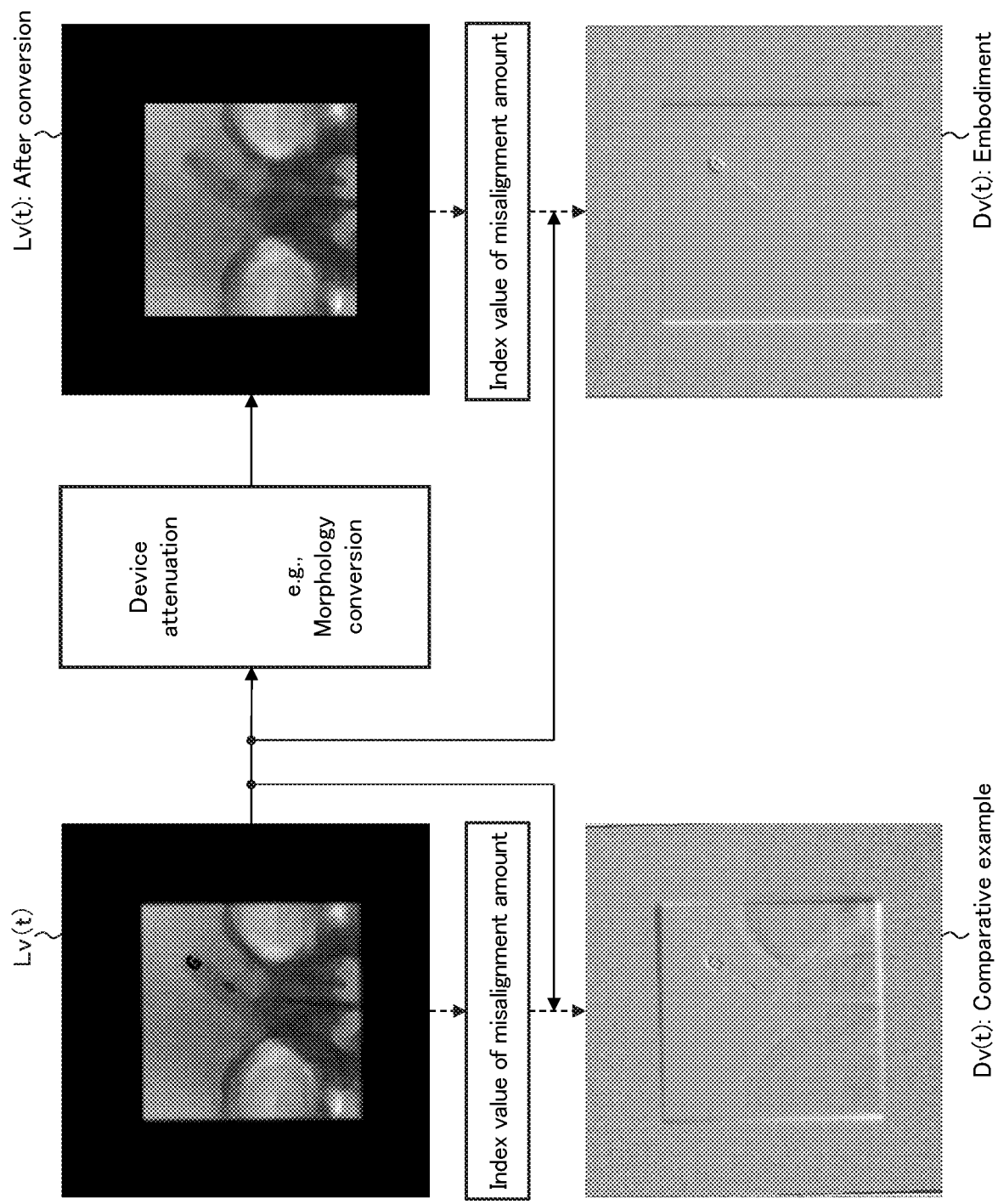
FIG. 28 is a schematic diagram for explaining an effect of the fourth embodiment.

Next, the operations according to the fourth embodiment will be described with reference to the flowchart in FIG. 26 and the schematic diagrams in FIGS. 27 and 28.

Suppose that steps ST10, ST21, and ST22 have now been performed in the manner as discussed, and the mask image Mk has been read and the live image Lv(t) has been acquired.

After step ST22, step ST_mp employing the morphology conversion as the image processing is performed. This step ST_mp includes steps ST_mp1 and ST_mp2.

In step ST_mp1, the processing circuitry 94 determines whether or not to perform the morphology conversion, and if it is determined that the morphology conversion is not to be performed, the processing transitions to step ST_r. If it is determined that the morphology conversion is to be performed, the processing transitions to step ST_mp2. This determination is enabled by, for example, setting a flag indicative of whether or not to perform the morphology conversion in the memory 91 in accordance with an operator's operation via the input interface 93, and configuring the processing circuitry 94 to refer to this flag.

In step ST_mp2 after step ST_mp1, the processing circuitry 94 performs the morphology conversion on the mask image Mk_dv and the live image Lv(t). By this morphology conversion, a curvilinear image component is erased or attenuated from each of the mask image Mk_dv and the live image Lv(t). This corresponds to the "Device attenuation" processing indicated in FIGS. 27 and 28. Upon performing such steps ST_mp1 to ST_mp2, step ST_mp with the morphology conversion as the image processing is complete.

In step ST_r after step ST_mp, the processing circuitry 94 sets a region of interest (ROI) for the position alignment in the live image Lv(t) after the morphology conversion. At this time, the processing circuitry 94 may likewise set a region of interest (ROI) in also the mask image Mk_dv, as well as in the live image Lv(t). According to this embodiment, the processing circuitry 94 sets a region of interest (ROI) for the position alignment in also the mask image Mk_dv after the morphology conversion.

After step ST_r, step ST25 including steps ST25d1 and ST25d2 is performed in the manner as discussed.

In step ST25d1, the processing circuitry 94 estimates the index value of the amount of misalignment between the mask image Mk and the live image Lv(t), which have undergone the morphology conversion, within the region of interest. According to this embodiment, the index value of the misalignment amount is estimated (calculated) based on both the images in the respective regions of interest (ROI's) of the mask image Mk_dv and the live image Lv(t). This corresponds to the "PS calculation" indicated in FIG. 27. The abbreviation "PS" stands for pixel shift.

In step ST25d2 after step ST25d1, the processing circuitry 94 performs the processing (PS processing) of shifting the mask image Mk_dv and/or the live image Lv(t) based on the estimated index value so that the index value is minimized. Note that the subject of this PS processing is the images before the morphology conversion. The series of processing from the PS calculation to the PS processing may be called "APS". The abbreviation "APS" stands for auto pixel shift.

Then, the processing circuitry 94 performs the image operation (subtraction) between, for example, the mask image Mk_dv_ps and the live image Lv(t)_ps obtained after the shift to generate the device image Dv(t). This device image Dv(t) according to the present embodiment is an image that allows for easy visual recognition of the device as understood from the lower-right part of FIG. 28, since the background therein has been canceled out. In contrast, the device image Dv(t) without the morphology conversion is an image that involves artifacts and does not allow for easy visual recognition of the device, as seen from the lower-left part of FIG. 28. Upon performing these steps ST25d1 and ST25d2, step ST25 is complete.

After step ST25, steps ST30 to ST40 are performed in the manner as discussed.

According to the fourth embodiment as described above, in advance of the position alignment between the first X-ray image and the second X-ray image acquired with a device inserted, image processing is performed on the first X-ray image and the second X-ray image so that a curvilinear or extending image component is erased or attenuated. The position alignment is performed based on the first X-ray image and the second X-ray image which have undergone this image processing. Therefore, the fourth embodiment provides the same advantages as those of the first to third embodiments without necessitating specifying a device area candidate. In addition, performing the image processing of erasing or attenuating a curvilinear or extending image component according to the fourth embodiment can reduce errors in the position alignment between images, which can occur due to the movement of the device during fluoroscopic imaging.

Moreover, according to the fourth embodiment, the image processing may be controlled according to a field of view of the second X-ray image. With this configuration, the filter size may be increased or decreased according to the field of view of the second X-ray image, so that the curvilinear or extending image component which could be magnified or minified can be erased or attenuated. That is, errors in the position alignment between images, which could occur due to the movement of a device during fluoroscopic imaging, can be suppressed even when the field of view of the second X-ray image is changed.

(Modification)

A modification of the fourth embodiment will be described. The fourth embodiment has been described, assuming the instances of performing the image processing of erasing or attenuating a curvilinear or extending image component before the inter-image position alignment. Also, the fourth embodiment has assumed a configuration capable of controlling the image processing of erasing or attenuating a curvilinear or extending image component, according to a field of view of the second X-ray image. According to this modification of the fourth embodiment, the image processing of erasing or attenuating a curvilinear or extending image component is controlled according to an operator's operation.

The processing circuitry 94 with the conversion function 944a accordingly controls the image processing on the first X-ray image and the second X-ray image for erasing or attenuating a curvilinear or extending image component, in response to an operation via the input interface 93. The operation via the input interface 93 here may be, for example, an operation with a GUI such as a slide bar, etc. on the screen, or an operation with hardware devices such as a keyboard, a mouse, etc. The control of the image processing includes, for example, a control to change the filter size for the morphology conversion.

The display 92 is adapted to display a live image Lv(t) both before the image processing is performed and after the image processing is performed. Note, however, that the modification of the fourth embodiment is not limited to the use of the live image Lv(t), and it is also applicable to the use of past still images or moving images, etc. Also, as in the cases of the foregoing embodiments, etc., the description using the components of the medical image processing apparatus 90, namely, the processing circuitry 94, the display 92, and so on, can be applied to the processing circuitry 74, the display 72, and so on of the X-ray diagnostic apparatus 1 as appropriate.

The remaining aspects are the same as the fourth embodiment.

Figure 29:
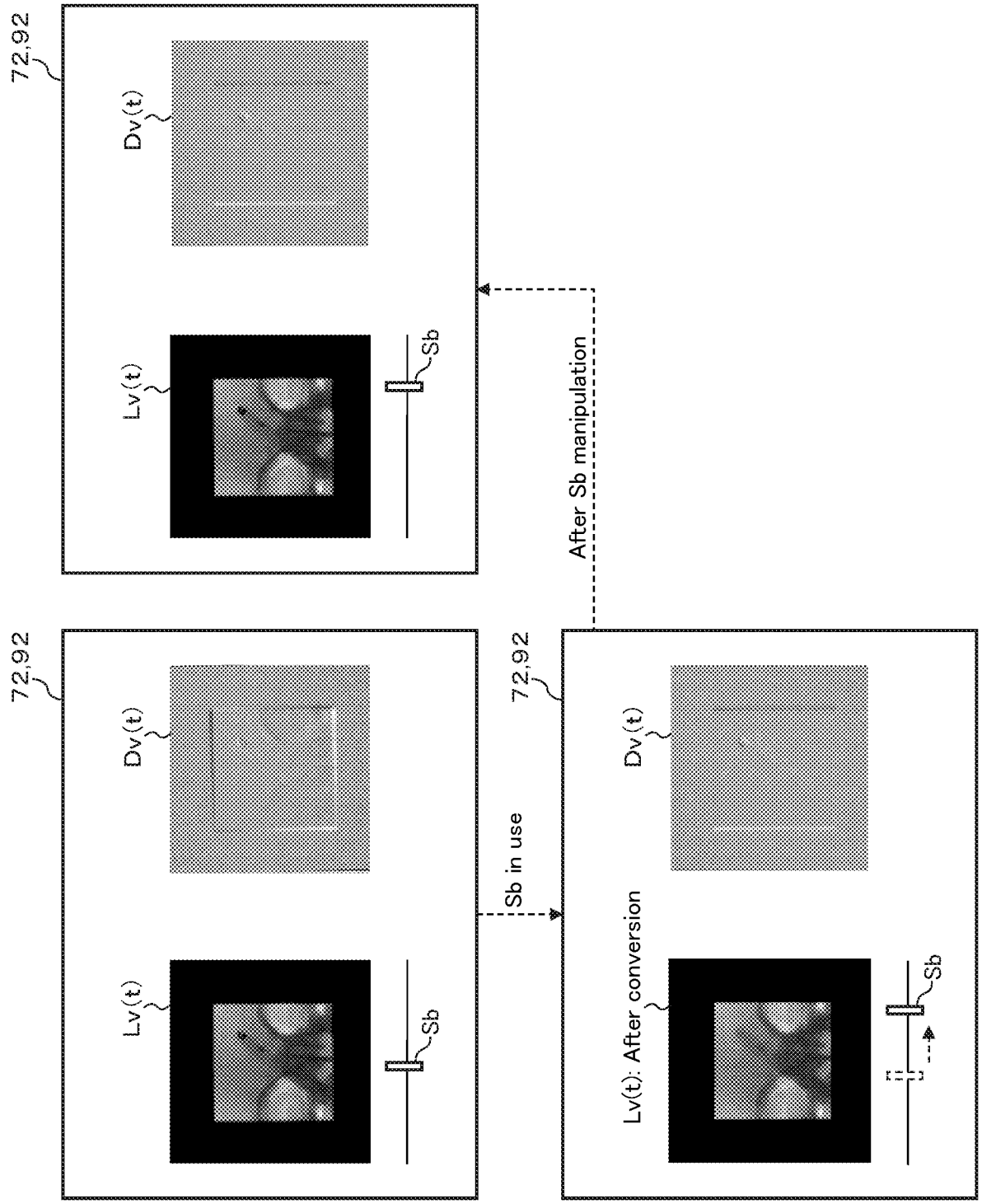
FIG. 29 is a schematic diagram for explaining operations in a modification of the fourth embodiment.

Suppose that, with the above configuration, the display 92 is now presenting a display as shown in the upper-left part of FIG. 29, where a live image Lv(t) before the morphology conversion, a device image Dv(t) involving a positional misalignment (misregistration), and a slide bar sb for controlling the morphology conversion are given.

In this state, the input interface 93 is operated such that the slide bar sb is moved rightward as shown in the lower-left part of FIG. 29 by holding a mouse (not illustrated). The mode selected here is a filter-size change mode. During this change mode, the display 92 displays, in place of the live image Lv(t) before the image processing, a live image Lv(t) having undergone the morphology conversion with a filter size according to the position of the slide bar sb. The operator controls the filter size for the morphology conversion by adjusting the slide bar sb, while checking the morphology-converted live image Lv(t). Along with this manipulation, the misalignment of the device image Dv(t) is resolved, and the device image Dv(t) turns an image with improved viewability.

The input interface 93 is then operated such that the slide bar sb is stopped as shown in the upper-right part of FIG. 29 by releasing the mouse (not illustrated). The filter-size change mode is thus released. The display 92 accordingly returns from the display of the live image Lv(t) after the morphology conversion, to the display of the live image Lv(t) before the morphology conversion. The device image Dv(t), which is currently displayed, remains a viewable image as discussed above.

In other words, the display 92 normally displays the live image Lv(t) before the morphology conversion, and displays the morphology-converted live image Lv(t) during the manipulation of the slide bar sb. With this configuration, the morphology conversion is controlled and adjusted using one display 92.

According to the modification of the fourth embodiment as discussed, the image processing of erasing or attenuating a curvilinear or extending image component is controlled according to an operator's operation. Therefore, errors that occur in the inter-image position alignment can be suppressed with fine adjustment according to the operator's operation.

Figure 30:
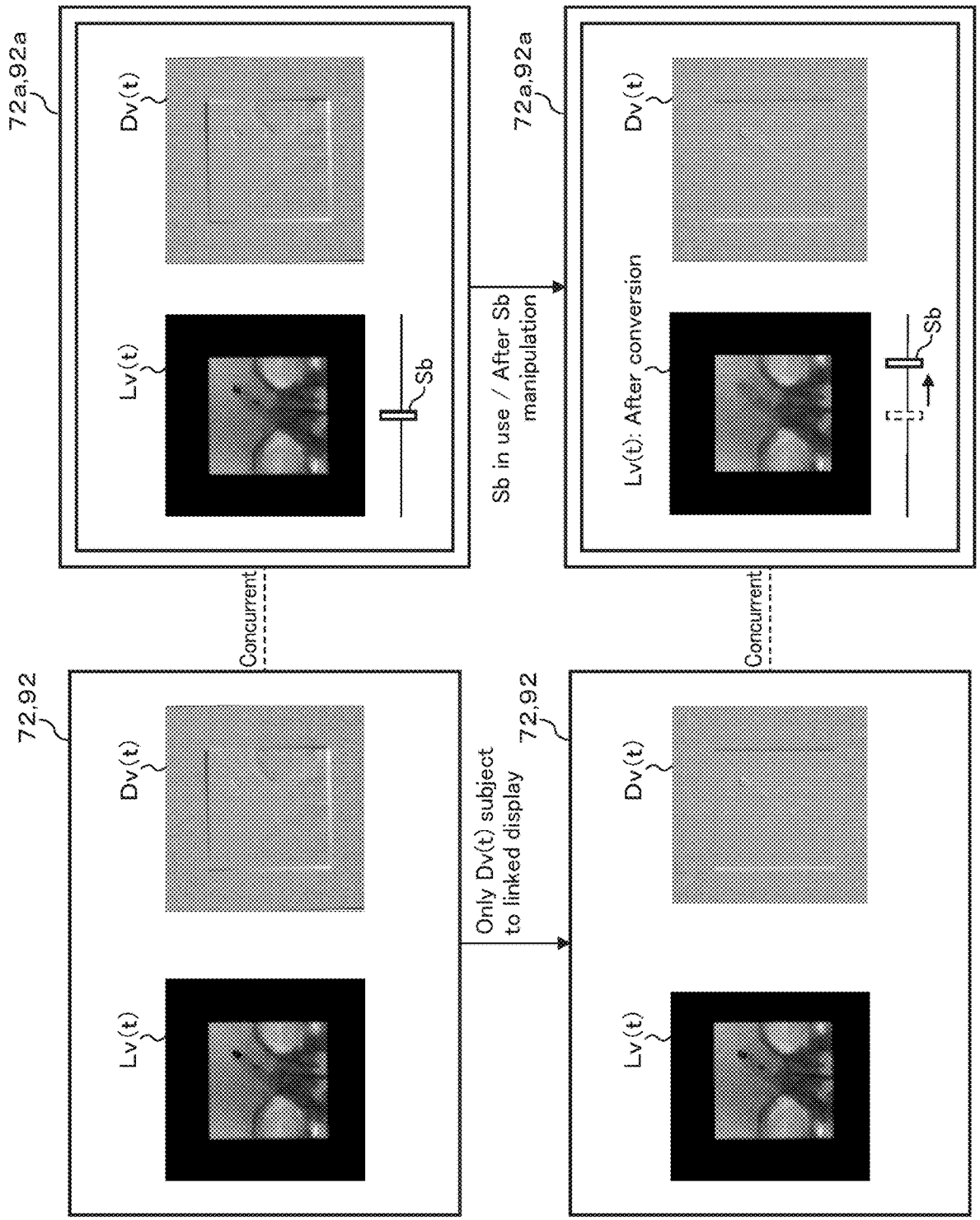
FIG. 30 is a schematic diagram for explaining operations in another modification of the fourth embodiment.

Note that the modification of the fourth embodiment has assumed the use of the single display 92 for switchover display between the live image Lv(t) during the normal time and the live image Lv(t) during the operation time. However, the modification of the fourth embodiment is not limited to this, but it may employ multiple displays 92's. For example, as shown in FIG. 30, the modification may configure the display 92 to be used for reference during the normal time including the time of treatment procedures, etc., while employing another display 92a for reference during the adjustment of the morphology conversion. Here, the display 92 always displays, for example, the live image Lv(t) before the morphology conversion, and the device image Dv(t). The separate display 92a always displays, for example, the live image Lv(t) after the morphology conversion, the device image Dv(t), and the slide bar sb. The device image Dv(t) on the display 92 and the device image Dv(t) on the display 92a are the same as each other.

Suppose that, with such a configuration, the display 92 is now presenting a display as shown in the upper-left part of FIG. 30, where a live image Lv(t) before the morphology conversion and a device image Dv(t) involving a positional misalignment (misregistration) are given. Also, the separate display 92a is supposed to be presenting a display as shown in the upper-right part of FIG. 30, where a live image Lv(t) before the morphology conversion and a device image Dv(t) involving a positional misalignment are similarly given together with a slide bar sb.

In this state, the input interface 93 is operated such that the slide bar sb is moved rightward as shown in the lower-right part of FIG. 30 by holding a mouse (not illustrated). At this time, the separate display 92a displays the live image Lv(t) having undergone the morphology conversion with a filter size according to the position of the slide bar sb. The operator controls the filter size for the morphology conversion by adjusting the slide bar sb, while checking the morphology-converted live image Lv(t). Along with this manipulation, the misalignment of the device image Dv(t) is resolved, and the device image Dv(t) turns an image with improved viewability. On the other hand, the live image Lv(t) displayed on the display 92 is given in the same manner without conversion, while the device image Dv(t) displayed on the display 92 is changed in the manner linked with the display on the separate display 92a, as shown in the lower-left part of FIG. 30.

That is, the display 92 may be dedicated to displaying the live image Lv(t) that is before the morphology conversion. The separate display 92a may be dedicated to displaying the morphology-converted live image Lv(t). As such, the modification of the fourth embodiment allows for the adjustment of the morphology conversion with the use of multiple displays such as the two displays 92 and 92a.

Fifth Embodiment

The fifth embodiment relates to the instances of specifying a device area candidate based on a blood vessel image corresponding to the second X-ray image.

Figure 31:
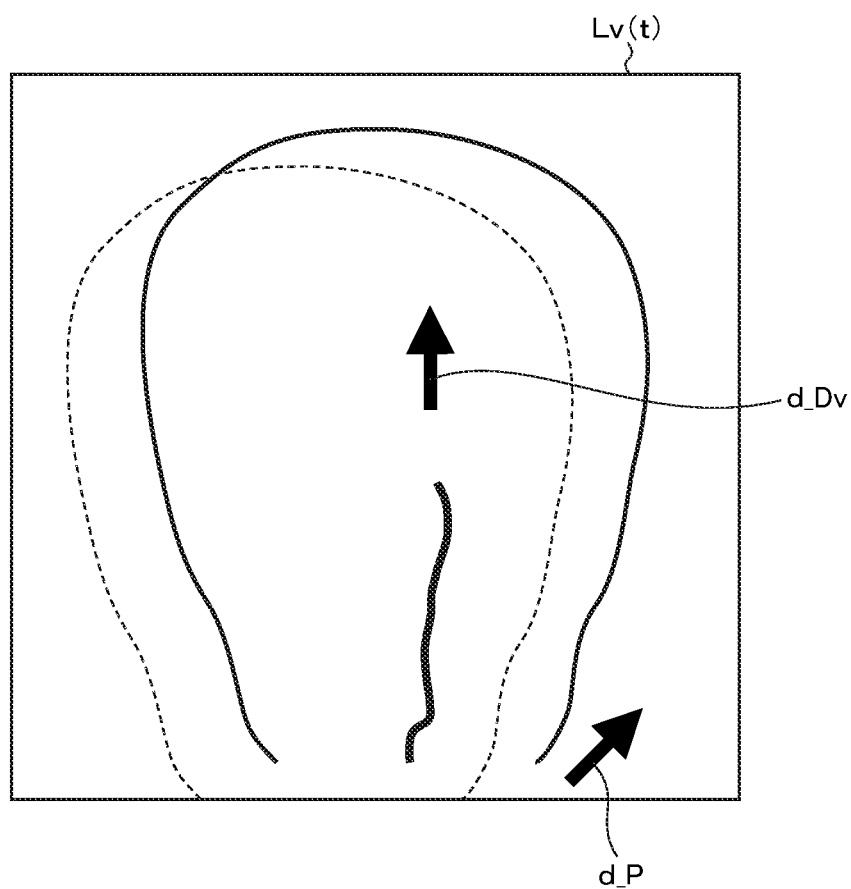
FIG. 31 is a schematic diagram for explaining multiple movement directions in the context of a fifth embodiment.

It is often the case during fluoroscopic imaging that, as shown in FIG. 31, a live image Lv(t) involves a direction d_p of the body motion of a subject P that differs from a direction d_dv of the movement of a device inserted into the subject P. This could result in errors in the position alignment between the live image Lv(t) and the mask image Mk_dv. Note that, when the position alignment is good, a device and a contrast-enhanced blood vessel in the fluoroscopy subtraction image Fs(t) overlap with each other as shown in FIG. 32(a). However, when the position alignment is not good, a device and a contrast-enhanced blood vessel in the fluoroscopy subtraction image Fs(t) are displaced from each other, and even artifacts appear in the image as shown in FIG. 32(b).

Figure 33:
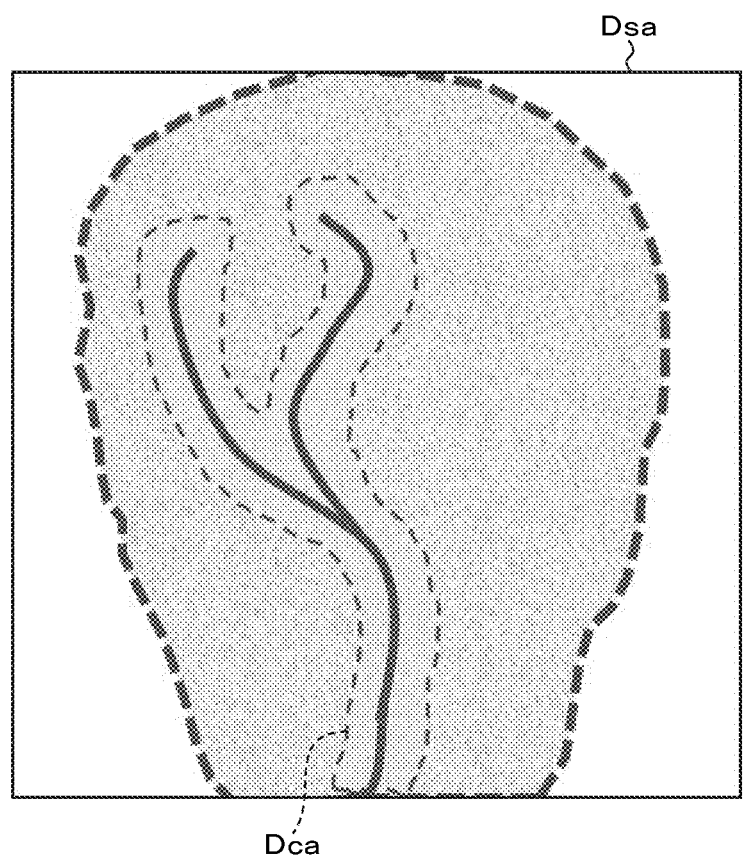
FIG. 33 is a schematic diagram for explaining one example of a device area candidate according to the fifth embodiment.
Figure 34:
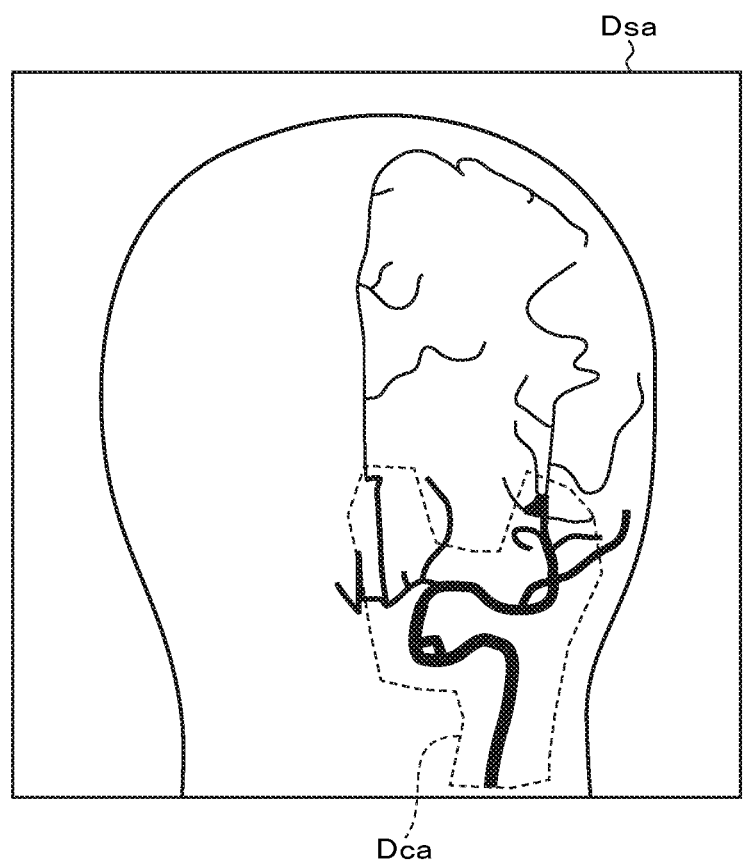
FIG. 34 is a schematic diagram for explaining another example of the device area candidate according to the fifth embodiment.

To this issue, the fifth embodiment uses a configuration in which the processing circuitry 94 with the area specifying function 945 specifies a device area candidate based on a blood vessel image corresponding to the second X-ray image. More specifically, and for example, the area specifying function 945 specifies an area in the blood vessel image Dsa, where at least part of a blood vessel region is expanded or dilated in its width direction, as the device area candidate Dca. One exemplary device area candidate Dca thus specified is an area as shown in FIG. 33, in which the whole of the blood vessel region is expanded in the width direction. Another exemplary device area candidate Dca may be an area as shown in FIG. 34, in which part of the blood vessel region is expanded in the width direction. Such widthwise expansion may be introduced by dilation processing using morphology conversion, etc. The size or degree of expansion may be set to any of values including a fixed value, a manually-adjusted value, and a value associated with the body size or vessel diameter. Also, setting a too large device area candidate Dca could deteriorate the accuracy of the position alignment, and therefore, the basis, i.e., the reference blood vessel region, may be limited as shown in FIG. 34. Limiting the blood vessel region is intended to focus on a range where the device is present, so its method may adopt, for example, one or more of the following (i) to (iv) or the like as appropriate.

(i) Method of limiting the reference blood vessel region to only a portion within a certain region of interest (any given region, or rectangular region, circular region, etc.).

(ii) Method of limiting the reference blood vessel region to only a portion falling within a range of a certain vessel diameter. According to this method, the reference blood vessel region can be limited to the range where the device passes.

(iii) Method of limiting the reference blood vessel region to only a portion falling within a range of a certain arrival time of the contrast medium. This method may use, for example, parameters in parametric imaging (PI), including a time to peak (TTP), a time to arrival (TTA), and so on. The PI technique calculates values of parameters such as a time of arrival or an average time of passage of a contrast medium from the pixel-based time-concentration curve obtained from angiography, and puts these parameter values in a pictorial representation for display using a color scale or gray scale. The time-concentration curve indicates a time by its horizontal axis and a concentration of a contrast medium by its vertical axis so that the temporal change of the concentration of the contrast medium (pixel value) is shown. Here, TTP indicates how long the concentration of the contrast medium takes to reach the peak. TTA indicates a time phase (time point) at which the concentration of the contrast medium has first exceeded a threshold TH in the time-concentration curve, namely, the arrival time of the contrast medium. The threshold TH may be any value discretionarily selected from the range of, for example, from 30 to 60% of the peak value. According to this method, it is possible to preclude capillary regions which are of later time phases.

(iv) Method of extracting a core line of a contrast-enhanced blood vessel, and based on the same, limiting the reference blood vessel region to only a portion falling within a range of a certain distance from the initial position in the image.

The position alignment function 946 performs, in the manner similar to the foregoing embodiments, etc., the position alignment including the first processing of removing the specified device area candidate Dca or the second processing of reducing a contribution of the device area candidate Dsa.

Figure 35:
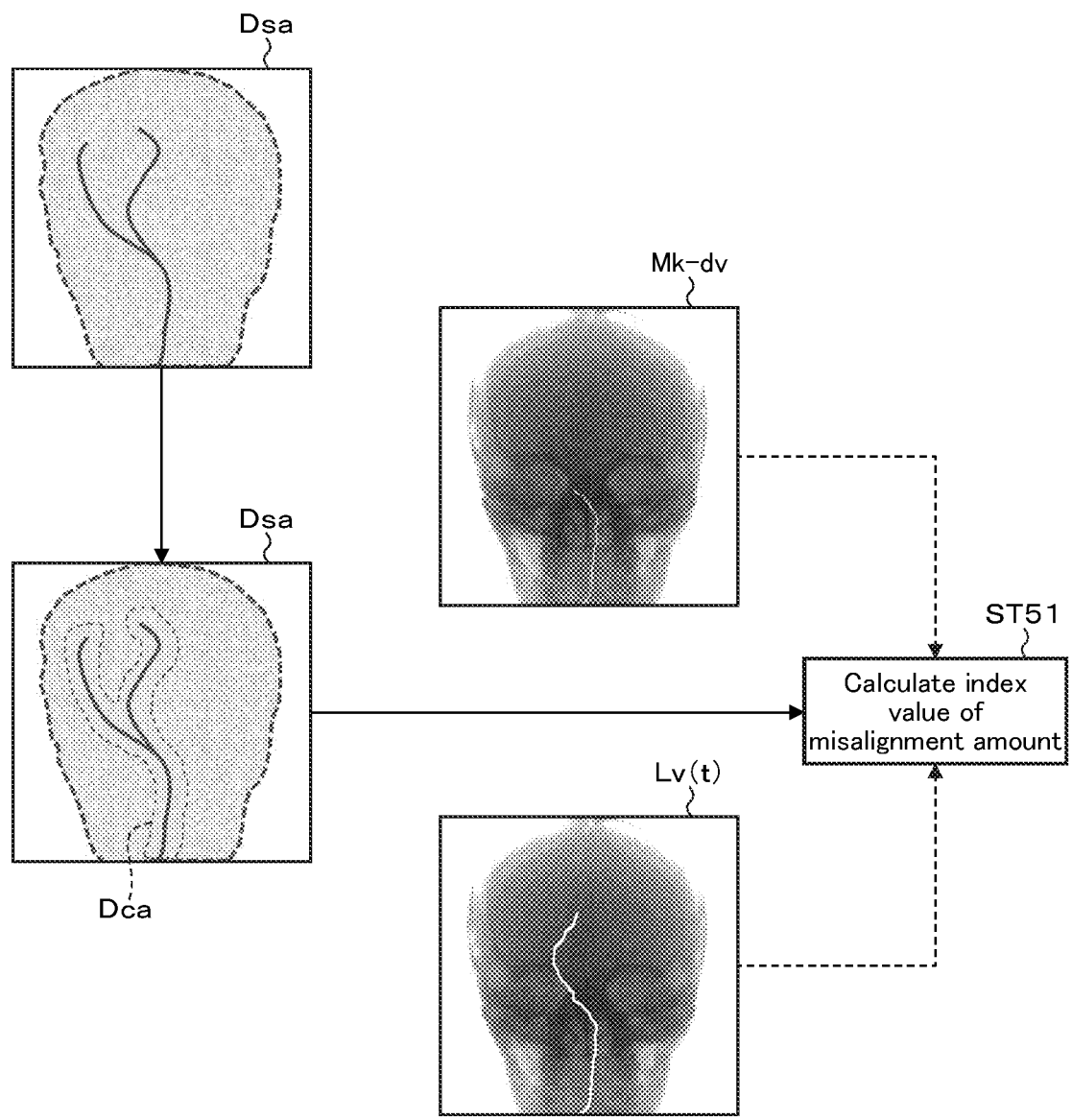
FIG. 35 is a schematic diagram for explaining a certain operation in the fifth embodiment.

According to the above configuration, the processing circuitry 94 specifies the device area candidate Dca based on the blood vessel image Dsa corresponding to the live image Lv(t), as shown in FIG. 35. More specifically, and for example, the processing circuitry 94 specifies an area in the blood vessel image Dsa, where at least part of a blood vessel region is expanded in its width direction, as the device area candidate Dca.

In light of the specified device area candidate Dca, the processing circuitry 94 subsequently applies the first processing or the second processing to the corresponding areas in the mask image Mk_dv and the live image Lv(t). As described, the first processing is processing of excluding the pixel values in the area. Also as described, the second processing is processing of reducing the contribution of the pixel values in the area.

Then, in step ST51, the processing circuitry 94 calculates the index value of the amount of misalignment between the mask image Mk_dv and the live image Lv(t), which have undergone the first processing or the second processing.

Figure 36:
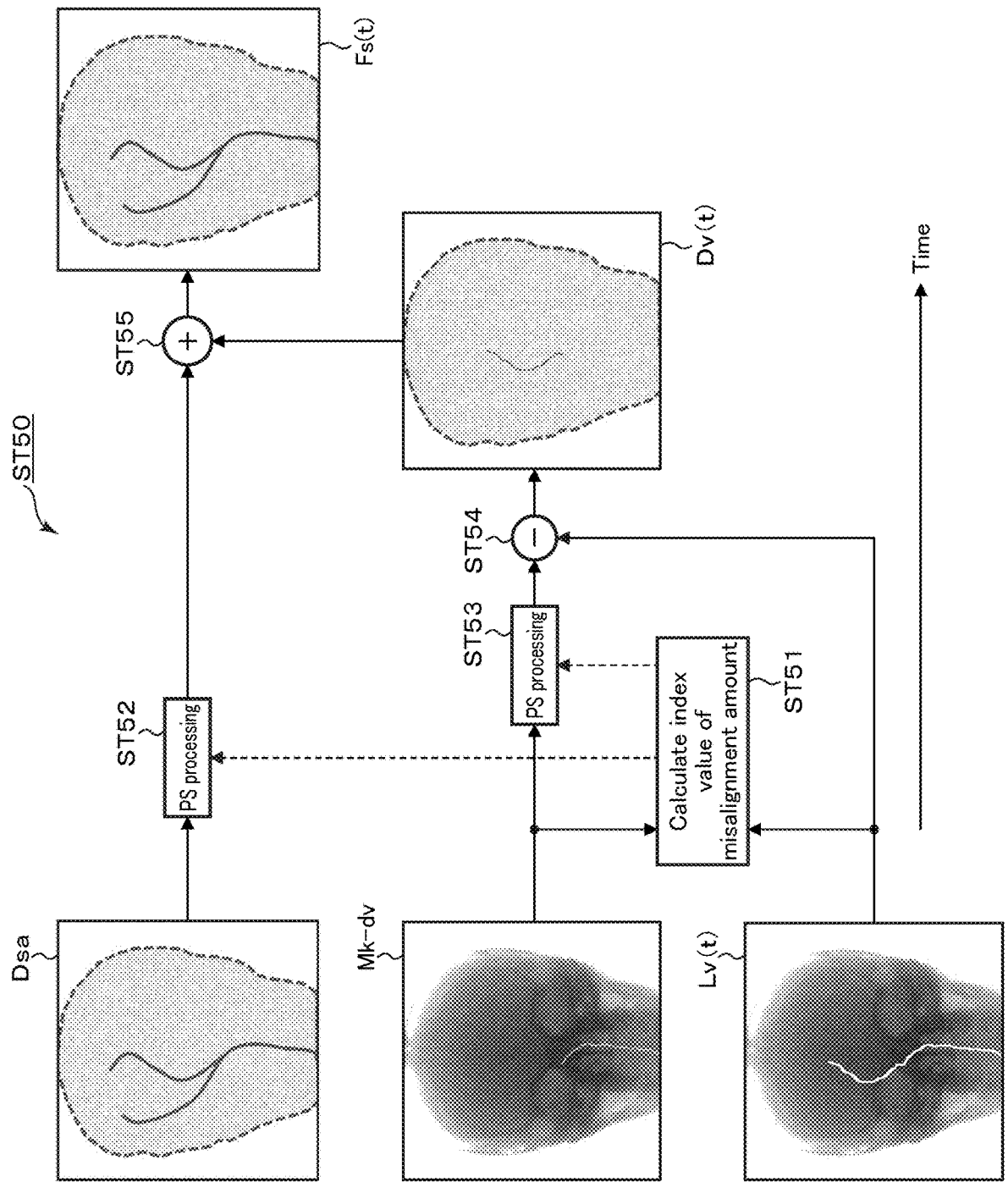
FIG. 36 is a schematic diagram for explaining operations in the fifth embodiment.

In step ST52 after step ST51, the processing circuitry 94 performs the position alignment of shifting the blood vessel image Dsa based on the calculated index value, as shown in FIG. 36.

In step ST53 after step ST52, the processing circuitry 94 performs the position alignment of shifting, for example, the mask image Mk_dv based on the calculated index value.

In step ST54 after step ST53, the processing circuitry 94 performs the image operation (subtraction) between the shifted mask image Mk_dv and the live image Lv(t) to generate the device image Dv(t).

In step ST55 after step ST54, the processing circuitry 94 performs the image operation (addition) between the shifted blood vessel image Dsa and the generated device image Dv(t) to generate the fluoroscopy subtraction image Fs(t). Upon performing these steps ST51 to ST55, step ST50 for image generation based on the live image Lv(t) is complete.

According to the fifth embodiment as discussed, a device area candidate is specified based on a blood vessel image corresponding to the second X-ray image. The blood vessel image shows a blood vessel region where the device is inserted, and as such, the device area candidate can be specified with high accuracy.

According also to the fifth embodiment, an area in this blood vessel image, where at least part of the blood vessel region is expanded in the width direction, may be specified as the device area candidate. This allows for further adopting a configuration of specifying the area that more likely includes the device among the areas of large widths as represented by blood vessel regions, as the device area candidate. Therefore, the device area candidate can be specified with even higher accuracy.

(First Modification)

The first modification of the fifth embodiment, as shown in FIG. 37, omits above-described steps ST53 and ST54. According to this first modification, the processing circuitry 94 performs the image operation (addition) between the blood vessel image Dsa shifted in step ST52 and the live image Lv(t) to generate the fluoroscopy roadmap (landmark) image Lm(t). Upon performing steps ST51, ST52, and ST55 in this manner, step ST50 for image generation based on the live image Lv(t) is complete.

The processing according to the first modification as such proceeds in the same manner as the fifth embodiment up to step ST51 of calculating the index value of misalignment amount, and therefore, the first modification can realize the same effects and advantages as those of the fifth embodiment.

(Second Modification)

Figure 38:
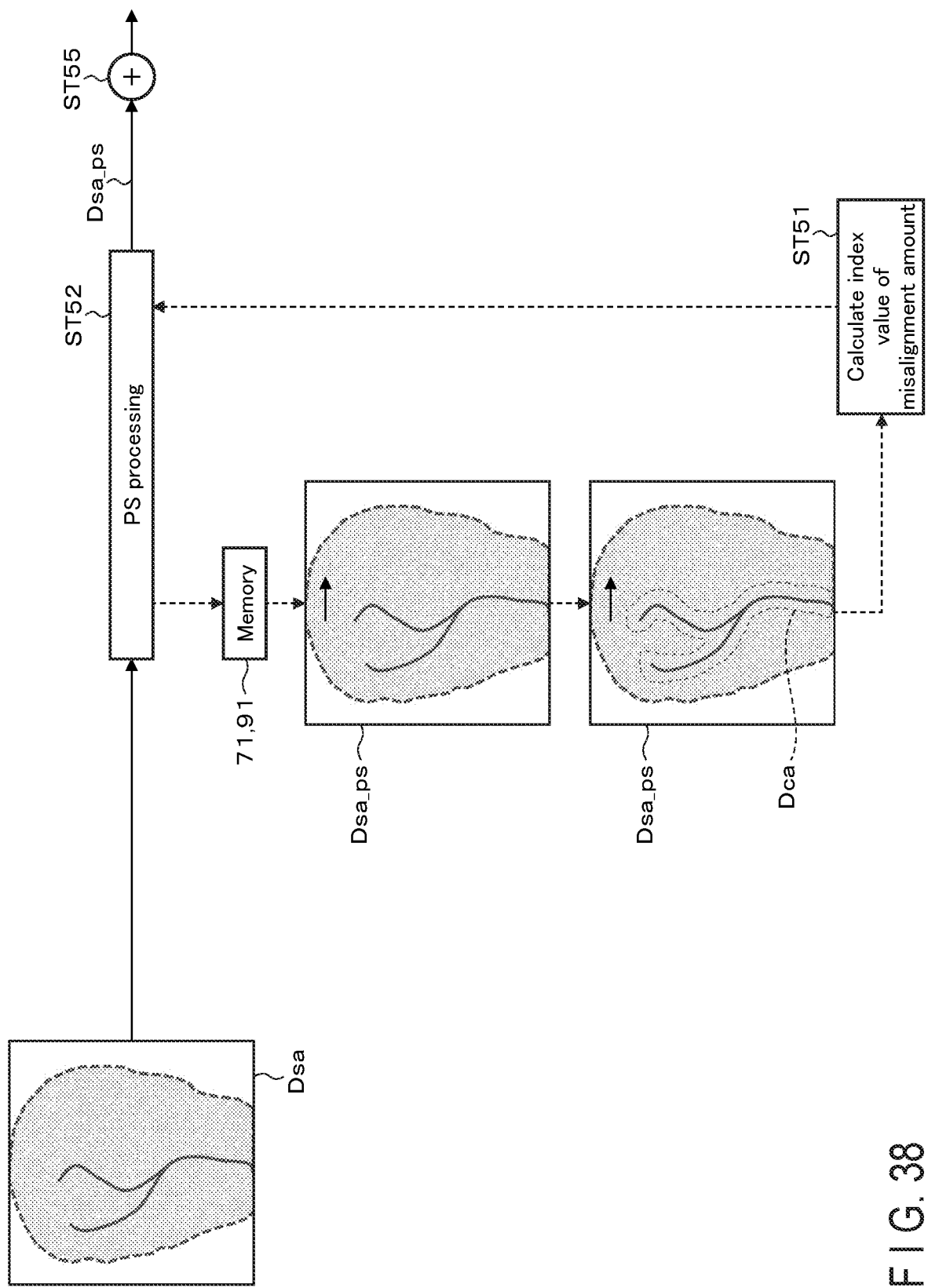
FIG. 38 is a schematic diagram for explaining a second modification of the operations in the fifth embodiment.

The second modification of the fifth embodiment, as shown in FIG. 38, stores in the memory 91 the blood vessel image Dsa_ps obtained by the shift process in step ST52, and specifies the device area candidate Dca afresh based on this blood vessel image Dsa_ps. According to this second modification, the device area candidate Dca is specified again according to the movement involved in the blood vessel image Dsa_ps, and therefore, occurrence of an event where the device crosses the boundary of the device area candidate Dca can be prevented.

Sixth Embodiment

The sixth embodiment relates to the instances of calculating an amount of deviation, etc. outside the device area candidate Dca of a dilated blood vessel region Bv, and this calculation takes advantage of a device Dv being present within the device area candidate Dca as shown in FIG. 39. The deviation amount outside the device area candidate Dca may be used as an index for evaluating the position alignment, because the smaller the deviation amount, the better the position alignment. Alternatively, or additionally, the deviation amount outside the device area candidate Dca may be used in the control for shifting images in the position alignment, as the preferred deviation amount is be equal to or below a threshold value.

The processing circuitry 94 with the position alignment function 946 accordingly calculates the amount of deviation between an external area in the second X-ray image that is outside the device area candidate and a partial area in the first X-ray image that corresponds to this external area in the second X-ray image, and performs the position alignment so that the deviation amount falls to or below the threshold value.

The remaining aspects are the same as the fifth embodiment.

Figure 40:
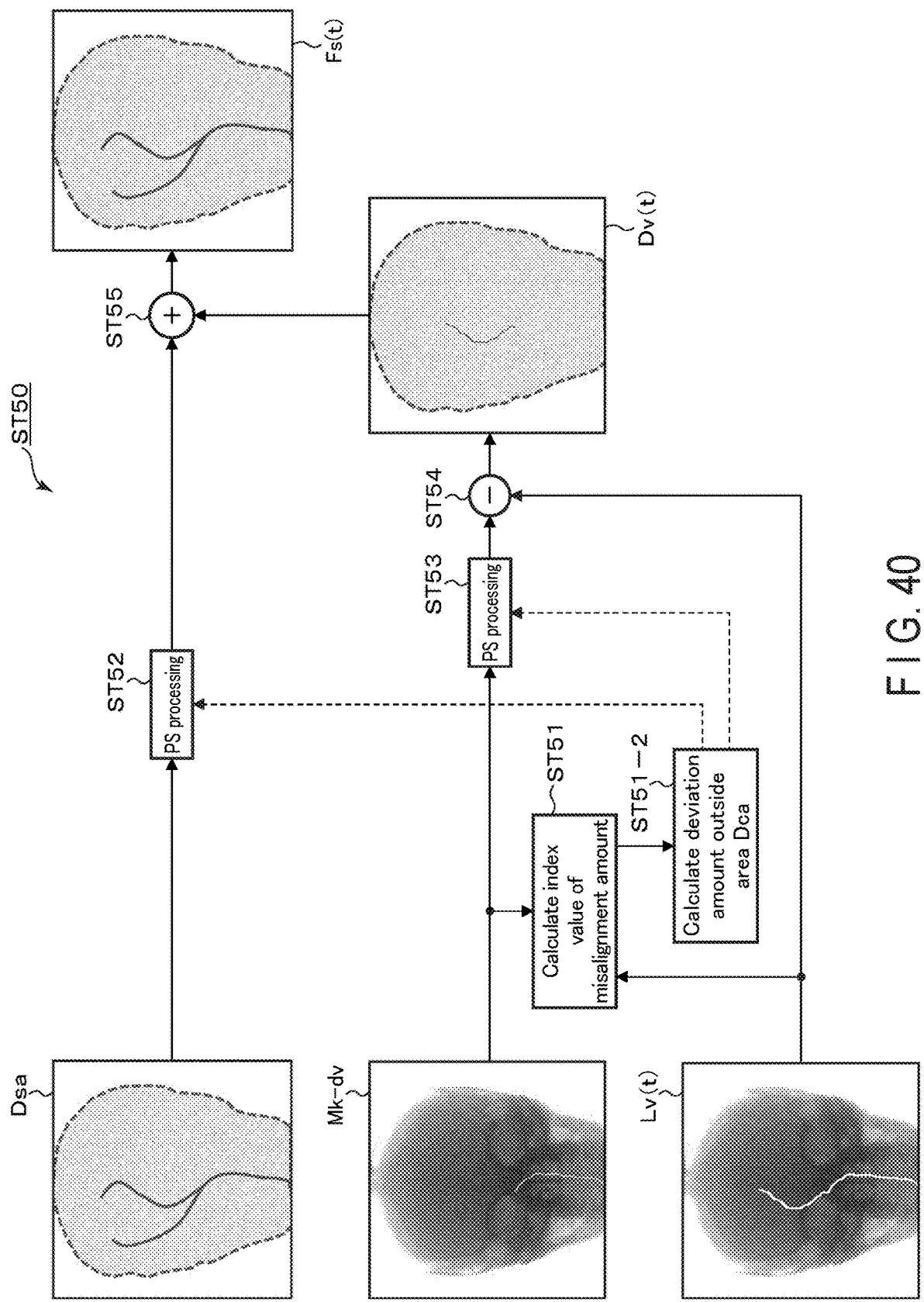
FIG. 40 is a schematic diagram for explaining operations in the sixth embodiment.

Referring to FIG. 40, the processing circuitry 94 according to this configuration applies, in light of the specified device area candidate Dca, the first processing or the second processing to the corresponding areas in the mask image Mk_dv and the live image Lv(t) in the manner as previously discussed.

Then, step ST51 is performed in the similar manner so that the index value of the amount of misalignment between the mask image Mk_dv and the live image Lv(t), which have undergone the first processing or the second processing, is calculated.

After step ST51, step ST51-2 is performed where the processing circuitry 94 calculates the amount of deviation between an external area outside the device area candidate Dca in the live image Lv(t) and a partial area in the mask image Mk_dv that corresponds to the external area.

In step ST52 after step ST51-2, the processing circuitry 94 performs the position alignment of shifting the blood vessel image Dsa to decrease this deviation amount to or below a threshold value, as well as to minimize the index value. The deviation amount is not limited to such use in the shift control, but it may be converted into an evaluation index and output. To prepare such an evaluation index, for example, deviation amounts may be marked for every given range and a range of small deviation amounts may be adopted as an index indicating a high, preferred quality. Adopting the deviation amount as an index in this manner may be applicable to also subsequent step ST53.

In step ST53 after step ST52, the processing circuitry 94 performs the position alignment of shifting the mask image Mk_dv to decrease the deviation amount to or below a threshold value and also to minimize the index value.

After step ST53, steps ST54 and ST55 are performed in the manner as discussed, whereby the device image Dv(t) and the fluoroscopy subtraction image Fs(t) are sequentially generated. Upon performing these steps ST51 to ST55, step ST50 for image generation based on the live image Lv(t) is complete.

According to the sixth embodiment as described, the amount of deviation between an external area outside the device area candidate in the second X-ray image and a partial area in the first X-ray image that corresponds to the external area in the second X-ray image is calculated, and the position alignment is performed so that the deviation amount falls to or below the threshold value. Therefore, the sixth embodiment can suppress the errors in the position alignment by performing the position alignment in such a manner as to keep the device from being positioned outside the device area candidate.

Seventh Embodiment

The seventh embodiment assumes a situation where the device area candidate is magnified along with a zoom action, and due to this, the area outside the device area candidate becomes relatively small and the position alignment becomes difficult. The seventh embodiment thus relates to the instances of performing the position alignment by a different method when the size of a field of view is small.

Figure 41:
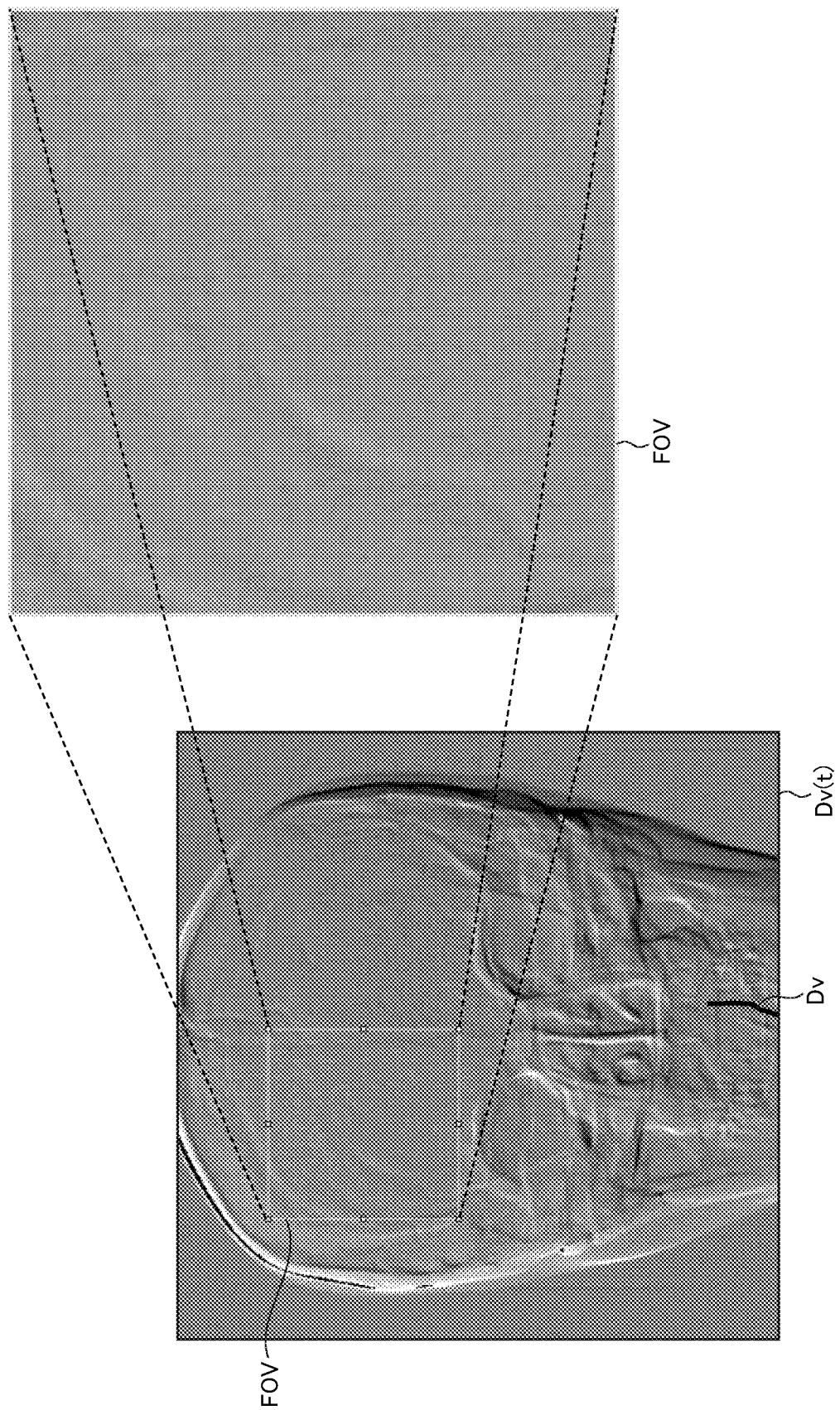
FIG. 41 is a schematic diagram for explaining a field of view (FOV) in the context of a seventh embodiment.

As a presupposition, an exemplary case without a device area candidate will be discussed. Suppose that a small FOV area is magnified according to a zoom action on the device image Dv(t) as shown in FIG. 41, some areas will give only a tiny index for misalignment, and the processing for the position alignment would be difficult with such areas. Also, as the area of small FOV is magnified, a variation attributable to a misalignment would be significant.

Figure 42:
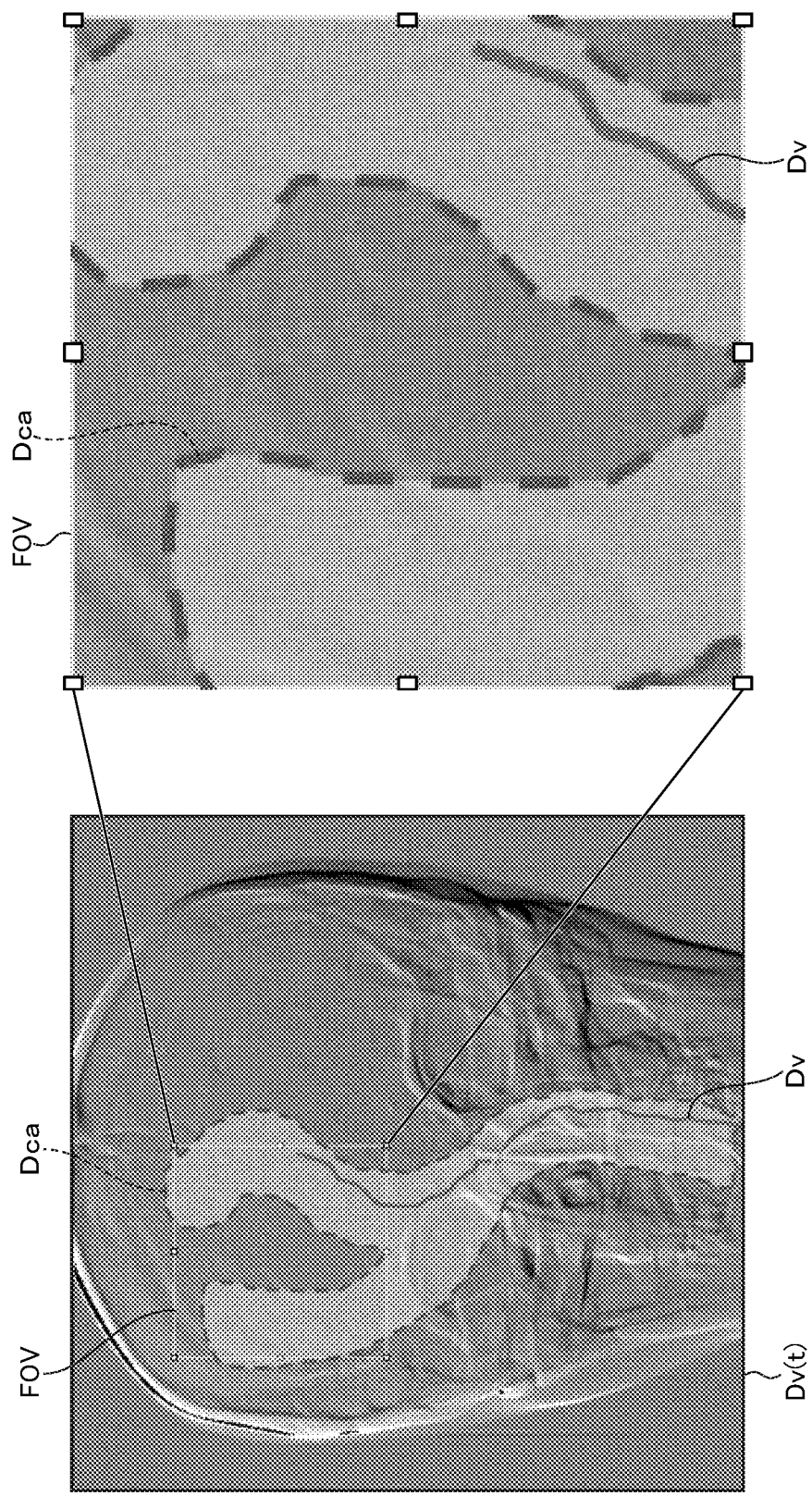
FIG. 42 is a schematic diagram for explaining a device area candidate within the FOV in the seventh embodiment.

Also, a case with a device area candidate will be discussed. For example, when the device area candidate Dca is magnified according to a zoom action on the device image Dv(t) as shown in FIG. 42, the area outside the device area candidate Dca becomes relatively small. That is, in the figure, while the area outside the device area candidate Dca accounts for eight-tenths or more of the image before magnification of the device area candidate Dca, it accounts for five-tenths or less of the image after the magnification of the device area candidate Dca. As such, after the magnification as shown in the right part of FIG. 42, performing the position alignment utilizing the area outside the device area candidate Dca is difficult.

The seventh embodiment, accordingly, performs the position alignment by a method different from employing the above-described first processing and second processing, when the size of a field of view is small.

Figure 43:
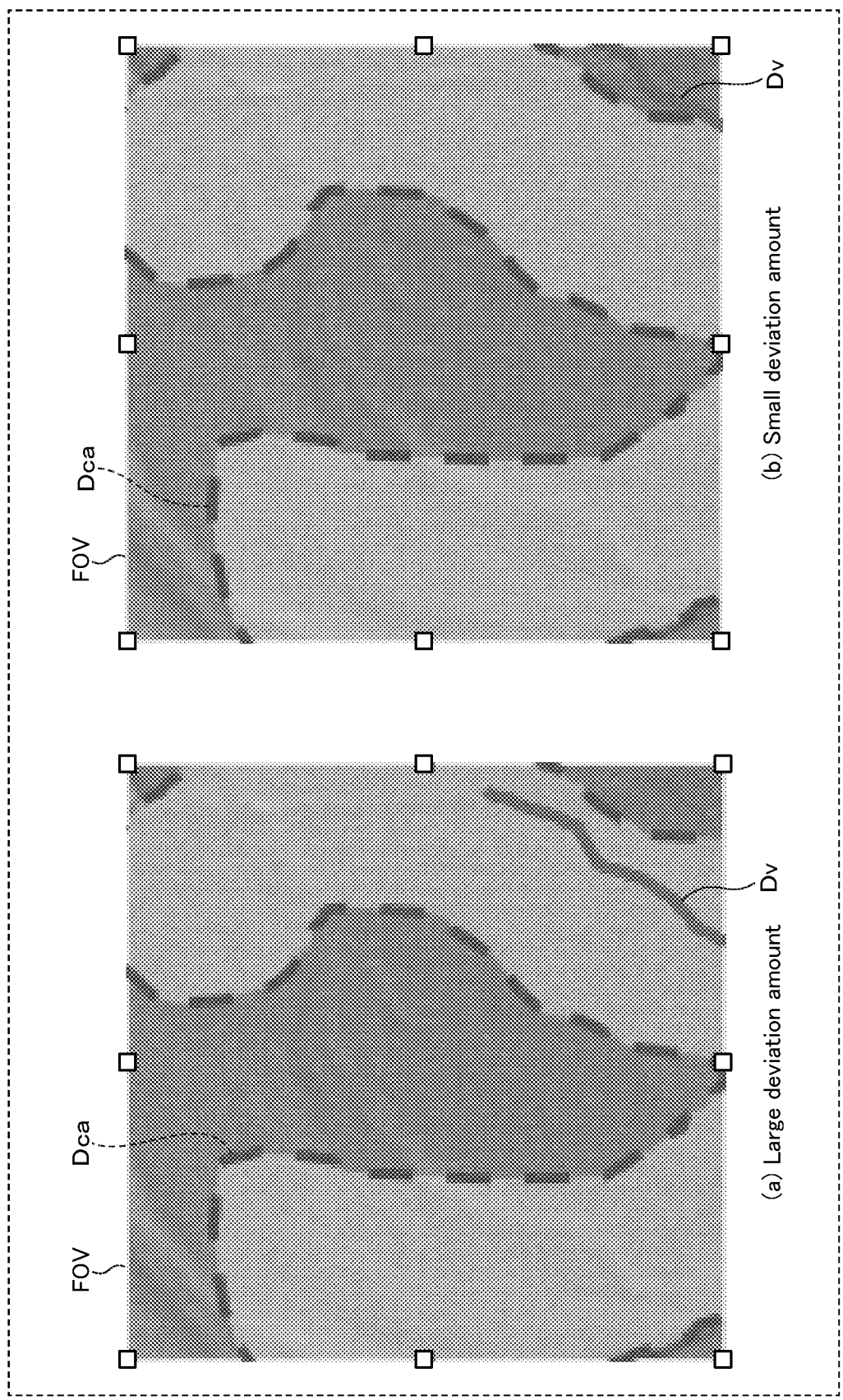
FIG. 43 is a schematic diagram for explaining an amount of deviation inside the device area candidate, according to the seventh embodiment.

More specifically, the processing circuitry 94 with the position alignment function 946 calculates, if the field of view of the second X-ray image has a size equal to or below a threshold, the amount of deviation between the device area candidate within the field of view of the second X-ray image and a partial area in the first X-ray image that corresponds to this device area candidate within the field of view without using the first processing or the second processing, and performs the position alignment so that the deviation amount is maximized. Note that, a large deviation amount here indicates that the device Dv is located in the device area candidate Dca as shown in FIG. 43(a). On the other hand, a small deviation amount indicates that the device Dv partly comes out from the device area candidate Dca as shown in FIG. 43(b). Therefore, the position alignment function 946 performs the position alignment so that the deviation amount is maximized and accordingly the device Dv is enclosed in the device area candidate Dca.

The remaining aspects are the same as the fifth embodiment.

Referring to FIG. 44, the processing circuitry 94 according to this configuration performs, when the field of view has a size larger than a threshold, step ST51 using the first processing or the second processing in the manner as discussed above. Then, the processing circuitry 94 performs steps ST52 to ST55 to generate the fluoroscopy subtraction image Fs(t).

On the other hand, if the field of view has a size equal to or below the threshold, the processing circuitry 94 performs step ST51-3 instead of performing the first processing, the second processing, or step ST51 as shown in FIG. 45. In step ST51-3, the processing circuitry 94 calculates the amount of deviation between the device area candidate Dca within the field of view of the live image Lv(t) and a partial area in the mask image Mk that corresponds to this device area candidate Dca within the field of view.

In step ST52 after step ST51-3, the processing circuitry 94 performs the position alignment of shifting the blood vessel image Dsa to maximize the deviation amount.

In step ST53 after step ST52, the processing circuitry 94 performs the position alignment of shifting the mask image Mk to maximize the deviation amount.

After step ST53, steps ST54 and ST55 are performed in the manner as discussed, whereby the device image Dv(t) and the fluoroscopy subtraction image Fs(t) are sequentially generated. Upon performing these steps ST51 to ST55, step ST50 for image generation based on the live image Lv(t) of the small field of view is complete.

According to the seventh embodiment as described, if the field of view of the second X-ray image has a size equal to or below a threshold, the amount of deviation between the device area candidate within the field of view of the second X-ray image and a partial area in the first X-ray image that corresponds to this device area candidate within the field of view is calculated without using the first processing or the second processing, and the position alignment is performed so that the deviation amount is maximized. Therefore, the seventh embodiment can suppress errors in the position alignment even with the field of view having a size equal to or below the threshold.

According to at least one of the foregoing embodiments, etc., the processing circuitry specifies, before position alignment between a first X-ray image and a second X-ray image, a device area candidate in the second X-ray image as a candidate of an area where the device appears. The second X-ray image is acquired with a device inserted. The processing circuitry performs the position alignment using first processing of removing the specified device area candidate or second processing of reducing a contribution of the device area candidate. Therefore, errors in the position alignment between the images, which can occur due to the movement of the device during fluoroscopic imaging, can be reduced.

The term "processor" used herein refers to, for example, a central processing unit (CPU) or a graphics processing unit (GPU), or various types of circuitry which may be an application-specific integrated circuit (ASIC), a programmable logic device (such as a simple programmable logic device (SPLD), a complex programmable logic device (CPLD), or a field programmable gate array (EPGA)), and so on. The processor reads programs stored in the storage circuitry and executes them to realize the respective functions. The programs may be incorporated directly in circuits of the processor, instead of being stored in the storage circuitry. According to such implementation, the processor reads the programs incorporated in its circuits and executes them to realize the functions. The embodiments, etc. do not limit the processor to a single circuitry-type processor. A plurality of independent circuits may be combined and integrated as one processor having multiple functions. Furthermore, multiple structural elements as given in FIG. 2 or 7 may be integrated as one processor to realize their functions.

While certain embodiments have been described, they have been presented by way of example only, and they are not intended to limit the scope of the inventions. These embodiments may be implemented in a variety of other forms with various omissions, substitutions, and changes without departing from the spirit of the inventions. The embodiments and their modifications are covered by the accompanying claims and their equivalents, as would fall within the scope and the gist of the inventions.

In relation to the foregoing embodiments, etc., following disclosures are additionally given, which set forth some of the various aspects of the inventions and alternative features thereof.

(Note 1a) A medical image processing apparatus includes an area specifier and a position aligner. The area specifier specifies, before position alignment between a first X-ray image and a second X-ray image which is acquired with a device inserted, a device area candidate in the second X-ray image as a candidate of an area where the device appears. The position aligner performs the position alignment using first processing of removing the specified device area candidate or second processing of reducing a contribution of the specified device area candidate.

(Note 1b) The area specifier and the position aligner may be implemented as processing circuitry.

(Note 1c) The area specifier may detect a device area showing the device from the second X-ray image, and may set the detected device area as the device area candidate.

(Note 1d) The area specifier may specify a device area candidate based on a blood vessel image corresponding to the second X-ray image.

(Note 1e) The area specifier may specify the device area candidate based on information about a motion between frames of the second X-ray image.

(Note 2a) The area specifier may specify the device area where the device is included, in also the first X-ray image acquired with the device inserted.

(Note 2b) The position aligner may perform the position alignment by applying the first processing or the second processing to the specified two device areas.

(Note 3a) The first processing may be image processing to erase, from the first X-ray image and/or the second X-ray image having been specified with the device area, the device that appears in this device area.

(Note 3b) The position alignment may include performing the first processing on the X-ray image having been specified with the device area, calculating an index value of the amount of misalignment between the first X-ray image and the second X-ray image based on the X-ray image having been subjected to the first processing, and shifting the first X-ray image or the second X-ray image based on the calculated index value.

(Note 4a) The second processing may be image processing to blur, in the first X-ray image and/or the second X-ray having been specified with the device area, the device that appears in this device area.

(Note 4b) The position alignment may include performing the second processing on the X-ray image having been specified with the device area, calculating an index value of the amount of misalignment between the first X-ray image and the second X-ray image based on the X-ray image having been subjected to the second processing, and shifting the first X-ray image or the second X-ray image based on the calculated index value.

(Note 5a) The first processing may exclude a pixel value of the specified device area from the calculation of the index value of the amount of misalignment between the first X-ray image and the second X-ray image.

(Note 5b) The position alignment may include calculating the index value of the amount of misalignment between the first X-ray image and the second X-ray image using the first processing, and shifting the first X-ray image or the second X-ray image based on the calculated index value.

(Note 6a) The second processing may reduce a contribution of a pixel value of the specified device area in the calculation of the index value of the amount of misalignment between the first X-ray image and the second X-ray image.

(Note 6b) The position alignment may include calculating the index value of the amount of misalignment between the first X-ray image and the second X-ray image using the second processing, and shifting the first X-ray image or the second X-ray image based on the calculated index value.

(Note 7a) A storage storing a trained model may be further provided. The trained model has been trained to have a function of specifying, based on an X-ray image acquired with a device inserted, the device area in the X-ray image where the device is included, and a function of outputting the specifying result.

(Note 7b) The area specifier may specify the device area in the latest X-ray image out of the first X-ray image and the second X-ray image based on the latest X-ray image and using the trained model.

(Note 8a) In this case, a storage adapted to store a blood vessel image that can be superimposed on each of the first X-ray image and the second X-ray image may be further provided.

(Note 8b) The area specifier may specify the device area by detecting the device from the latest X-ray image out of the first X-ray image and the second X-ray image, based on a dilated blood vessel region in the blood vessel image where a blood vessel region is expanded in its width direction.

(Note 9a) In this case, a storage adapted to store a blood vessel image that can be superimposed on each of the first X-ray image and the second X-ray image may be further provided.

(Note 9b) The area specifier may specify the device area by detecting the device from the latest X-ray image out of the first X-ray image and the second X-ray image, based on a blood vessel region wider than a reference width among blood vessel regions or widthwise-expanded blood vessel regions in the blood vessel image.

(Note 10) In lieu of the blood vessel region wider than a reference width, a blood vessel region of a designated range may be used.

(Note 11) In lieu of the blood vessel region wider than a reference width, a blood vessel region serving as a route to a treatment site may be used.

(Note 12) The area specifier may specify, as the device area, an area equal to or below a threshold in the latest X-ray image out of the first X-ray image and the second X-ray image.

(Note 13) The area specifier may specify, as the device area candidate, an area in the blood vessel image where the blood vessel region is expanded in the width direction.

(Note 14) The position aligner may calculate the amount of deviation between an external area outside the device area candidate in the second X-ray image and a partial area in the first X-ray image that corresponds to the external area, and may perform the position alignment so that the amount of deviation falls to or below a threshold value.

(Note 15) The position aligner may calculate, if the field of view of the second X-ray image has a size equal to or below a threshold, the amount of deviation between the device area candidate within the field of view of the second X-ray image and a partial area in the first X-ray image that corresponds to the device area candidate within the field of view, without using the first processing or the second processing, and may perform the position alignment so that the amount of deviation is maximized.

(Note 16) The area specifier may specify the device area candidate based on spatial distribution of a motion between frames of the second X-ray image.

(Note 17) The area specifier may specify the device area candidate based on, among the spatial distribution of the motion, information about a motion that is locally distributed in concordance with the device.

(Note 18) The area specifier may specify, as the device area candidate, an area including a portion showing a local movement.

(Note 19a) An image generator may be further provided for generating a fluoroscopy roadmap image based on the second X-ray image by performing the position alignment and the image operation upon performing the specifying operation.

(Note 19b) The image generator may be implemented as the processing circuitry.

(Note 20a) A medical image processing apparatus includes an image processor and a position aligner. The image processor performs, before position alignment between a first X-ray image and a second X-ray image which is acquired with a device inserted, image processing on the first X-ray image and the second X-ray image so that an extending image component is erased or attenuated. The position aligner performs the position alignment based on the first X-ray image and the second X-ray image after the image processing.

(Note 20b) The image processor and the position aligner may be implemented as processing circuitry.

(Note 20c) The image processor may control the image processing according to a field of view of the second X-ray image.

(Note 21) An X-ray diagnostic apparatus includes each feature of the medical image processing apparatus as above.

(Note 22) A computer-implemented method includes performing each feature of the medical image processing apparatus as above.

(Note 23a) A program causes a computer to perform each feature of the medical image processing apparatus as above.

(Note 23b) A program causes a processor of a computer to perform each feature of the medical image processing apparatus as above.

(Note 24) A non-transitory computer-readable storage medium stores the program.

The invention claimed is:

1. A medical image processing apparatus comprising:
processing circuitry configured to
specify, before position alignment between a first X-ray image and a second X-ray image which is acquired with a device inserted, a device area candidate in the second X-ray image as a candidate of an area where the device appears, and
perform the position alignment using first processing of removing the specified device area candidate or second processing of reducing a contribution of the specified device area candidate, wherein
the first X-ray image is acquired with the device inserted, and
the processing circuitry is configured to
detect a device area showing the device from the second X-ray image, and set the detected device area as the device area candidate,
specify the device area where the device is included, in also the first X-ray image, and
perform the position alignment by applying the first processing or the second processing to the specified two device areas.

2. The medical image processing apparatus according to claim 1, wherein the processing circuitry is configured to specify the device area candidate based on a blood vessel image corresponding to the second X-ray image.

3. The medical image processing apparatus according to claim 1, wherein the processing circuitry is configured to specify the device area candidate based on information about a motion between frames of the second X-ray image.

4. The medical image processing apparatus according to claim 1, wherein
the first processing comprises image processing to erase, from an X-ray image having been specified with the device area out of the first X-ray image and the second X-ray image, the device that appears in the device area, and
the position alignment comprises performing the first processing on the X-ray image having been specified with the device area, calculating an index value of an amount of misalignment between the first X-ray image and the second X-ray image based on the X-ray image having been subjected to the first processing, and shifting the first X-ray image or the second X-ray image based on the calculated index value.

5. The medical image processing apparatus according to claim 1, wherein
the second processing comprises image processing to blur, in an X-ray image having been specified with the device area out of the first X-ray image and the second X-ray image, the device that appears in the device area, and
the position alignment comprises performing the second processing on the X-ray image having been specified with the device area, calculating an index value of an amount of misalignment between the first X-ray image and the second X-ray image based on the X-ray image having been subjected to the second processing, and shifting the first X-ray image or the second X-ray image based on the calculated index value.

6. The medical image processing apparatus according to claim 1, wherein
the first processing comprises excluding a pixel value of the specified device area from calculation of an index value of an amount of misalignment between the first X-ray image and the second X-ray image, and
the position alignment comprises calculating the index value of the amount of misalignment between the first X-ray image and the second X-ray image using the first processing, and shifting the first X-ray image or the second X-ray image based on the calculated index value.

7. The medical image processing apparatus according to claim 1, wherein
the second processing comprises reducing a contribution of a pixel value of the specified device area in calculation of an index value of an amount of misalignment between the first X-ray image and the second X-ray image, and
the position alignment comprises calculating the index value of the amount of misalignment between the first X-ray image and the second X-ray image using the second processing, and shifting the first X-ray image or the second X-ray image based on the calculated index value.

8. The medical image processing apparatus according to claim 1, further comprising a memory storing a trained model, the trained model trained to have a function of specifying, based on an X-ray image acquired with a device inserted, the device area in the X-ray image where the device is included and a function of outputting the specifying result,
wherein the processing circuitry is configured to specify the device area in a latest X-ray image out of the first X-ray image and the second X-ray image based on the latest X-ray image and using the trained model.

9. A medical image processing apparatus,
comprising:
processing circuitry configured to
specify, before position alignment between a first X-ray image and a second X-ray image which is acquired with a device inserted, a device area candidate in the second X-ray image as a candidate of an area where the device appears, and
perform the position alignment using first processing of removing the specified device area candidate or second processing of reducing a contribution of the specified device area candidate,
wherein the processing circuitry is configured to specify the device area candidate based on a blood vessel image corresponding to the second X-ray image, and
wherein the processing circuitry is configured to specify, as the device area candidate, an area in the blood vessel image where a blood vessel region is expanded in a width direction.

10. The medical image processing apparatus according to claim 3, wherein the processing circuitry is configured to specify the device area candidate based on spatial distribution of the motion between frames of the second X-ray image.

11. The medical image processing apparatus according to claim 10, wherein the processing circuitry is configured to specify the device area candidate based on, among the spatial distribution of the motion, information about a motion that is locally distributed in concordance with the device.

12. The medical image processing apparatus according to claim 11, wherein the processing circuitry is configured to specify, as the device area candidate, an area including a portion showing a local movement.

13. The medical image processing apparatus according to claim 1, wherein the processing circuitry is configured to generate a fluoroscopy roadmap image based on the second X-ray image by performing the position alignment and an image operation upon performing said specifying.

14. An X-ray diagnostic apparatus comprising the medical image processing apparatus according to claim 1.

15. A computer-implemented method comprising:
specifying, before position alignment between a first X-ray image and a second X-ray image which is acquired with a device inserted, a device area candidate in the second X-ray image as a candidate of an area where the device appears; and
performing the position alignment using first processing of removing the specified device area candidate or second processing of reducing a contribution of the specified device area candidate
wherein the first X-ray image is acquired with the device inserted, and
the method further comprises:
detecting a device area showing the device from the second X-ray image, and set the detected device area as the device area candidate,
specifying the device area where the device is included, in also the first X-ray image, and
performing the position alignment by applying the first processing or the second processing to the specified two device areas.

16. A medical image processing apparatus comprising:
processing circuitry configured to
perform, before position alignment between a first X-ray image and a second X-ray image which is acquired with a device inserted, image processing on the first X-ray image and the second X-ray image so that an extending image component is erased or attenuated, and
perform the position alignment based on the first X-ray image and the second X-ray image after the image processing, wherein
the first X-ray image is acquired with the device inserted, and
the processing circuitry is further configured to
specify a device area showing the device from the second X-ray image,
specify the device area where the device is included, in also the first X-ray image, and
perform the position alignment by applying image processing to the two specified device areas.

17. The medical image processing apparatus according to claim 16, wherein the processing circuitry is configured to control the image processing according to a field of view of the second X-ray image.

18. An X-ray diagnostic apparatus comprising the medical image processing apparatus according to claim 16.

* * * * *